(12) United States Patent
Zon et al.

(10) Patent No.: US 10,668,039 B2
(45) Date of Patent: Jun. 2, 2020

(54) METHODS FOR TREATMENT OF ADENOID CYSTIC CARCINOMA

(71) Applicant: THE CHILDREN'S MEDICAL CENTER CORPORATION, Boston, MA (US)

(72) Inventors: Leonard I. Zon, Wellesley, MA (US); Joseph Mandelbaum, Boston, MA (US)

(73) Assignee: THE CHILDREN'S MEDICAL CENTER CORPORATION, Boston, MA (US)

(*) Notice: Subject to any disclaimer, the term of this patent is extended or adjusted under 35 U.S.C. 154(b) by 0 days.

(21) Appl. No.: 16/329,827

(22) PCT Filed: Sep. 1, 2017

(86) PCT No.: PCT/US2017/049861
§ 371 (c)(1),
(2) Date: Mar. 1, 2019

(87) PCT Pub. No.: WO2018/045289
PCT Pub. Date: Mar. 8, 2018

(65) Prior Publication Data
US 2019/0192468 A1    Jun. 27, 2019

Related U.S. Application Data

(60) Provisional application No. 62/383,230, filed on Sep. 2, 2016.

(51) Int. Cl.
| | | |
|---|---|---|
| *A61K 31/203* | (2006.01) | |
| *A61K 45/06* | (2006.01) | |
| *A61K 31/192* | (2006.01) | |
| *A61K 31/196* | (2006.01) | |
| *A61K 31/426* | (2006.01) | |
| *G01N 33/68* | (2006.01) | |
| *A61K 31/167* | (2006.01) | |
| *A61P 35/00* | (2006.01) | |
| *A61K 9/00* | (2006.01) | |

(52) U.S. Cl.
CPC .......... *A61K 31/203* (2013.01); *A61K 9/0053* (2013.01); *A61K 31/167* (2013.01); *A61K 31/192* (2013.01); *A61K 31/196* (2013.01); *A61K 31/426* (2013.01); *A61K 45/06* (2013.01); *A61P 35/00* (2018.01); *G01N 33/6875* (2013.01); *G01N 2500/10* (2013.01)

(58) Field of Classification Search
None
See application file for complete search history.

(56) References Cited

U.S. PATENT DOCUMENTS

| | | |
|---|---|---|
| 2004/0122080 A1 | 6/2004 | Vivat-Hannah et al. |
| 2004/0234624 A1 | 11/2004 | McKearn et al. |
| 2007/0292876 A1 | 12/2007 | Chen et al. |
| 2008/0119559 A1 | 5/2008 | Weissbach et al. |
| 2014/0051760 A1 | 2/2014 | Miller et al. |

FOREIGN PATENT DOCUMENTS

| | | |
|---|---|---|
| WO | 2000038730 A3 | 7/2000 |
| WO | 2014123476 A1 | 8/2014 |

OTHER PUBLICATIONS

FDA, "Guidance for Industry Estimating the Maximum Safe Starting Dose", Jul. 2005 https://www.researchgate.net/deref/http%3A%2F%2Fwww.fda.gov%2Fdownloads%2Fdrugs%2Fguidancecomplianceregulatoryinformation%2Fguidances%2Fucm078932.pdf ( Year: 2005).*

Soignet et al., "Initial clinical trial of a high-affinity retinoic acid ligand (LGD1550)". Clinical Cancer Research 6: 1731-1735 (200) 2000.

Chen et al., "Effect of all-trans-retinoic acid on inhibition of human salivary adenoid cystic carcinoma cell proliferation in vitro". International Journal of Oral and Maxillofacial Surgery 29:157 (2000).

Deb et al., "9-cis Retinoic acid inhibits cumulus cell apoptosis during the maturation of bovine cumulus-oocyte-complexes". Journal of Animal Science 09(6):1798-1806 (2012).

* cited by examiner

*Primary Examiner* — James D. Anderson
*Assistant Examiner* — Stephanie K Springer
(74) *Attorney, Agent, or Firm* — Nixon Peabody LLP

(57) ABSTRACT

The present invention is directed to compositions and methods for treating Adenoid Cystic Carcinoma (ACC).

15 Claims, 46 Drawing Sheets
Specification includes a Sequence Listing.

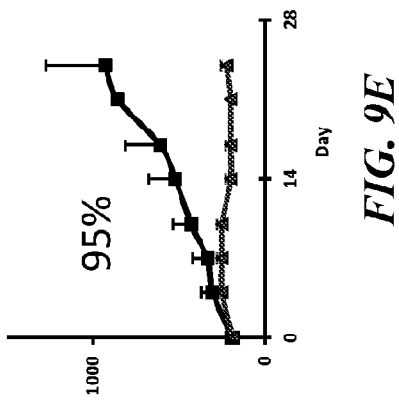
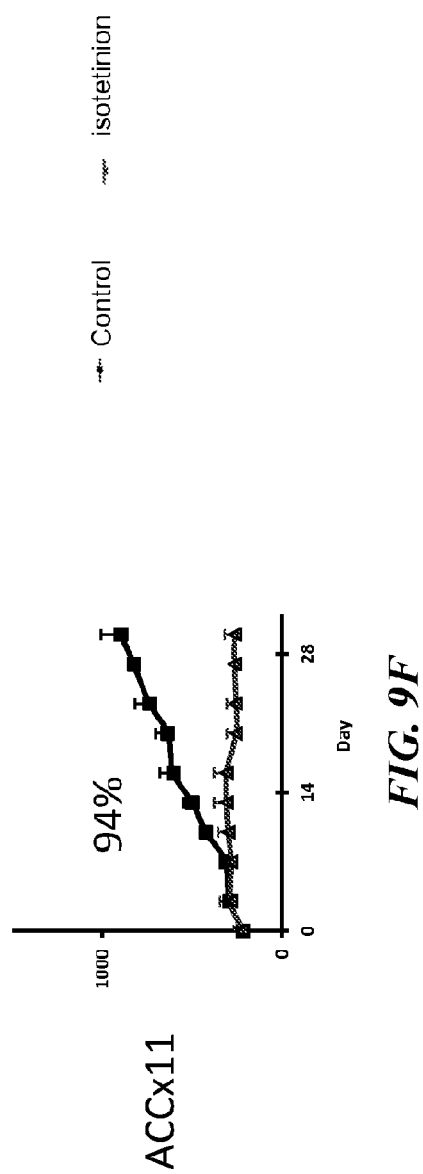
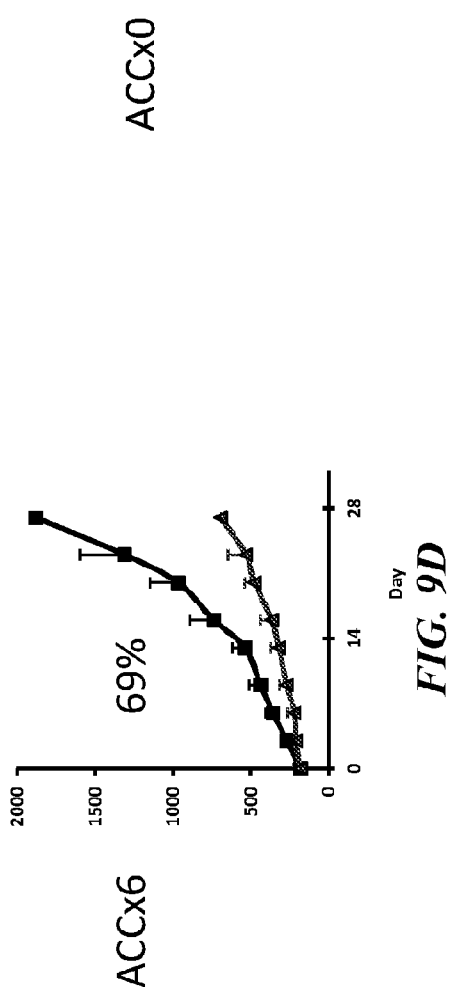
FIG. 9D
FIG. 9E
FIG. 9F

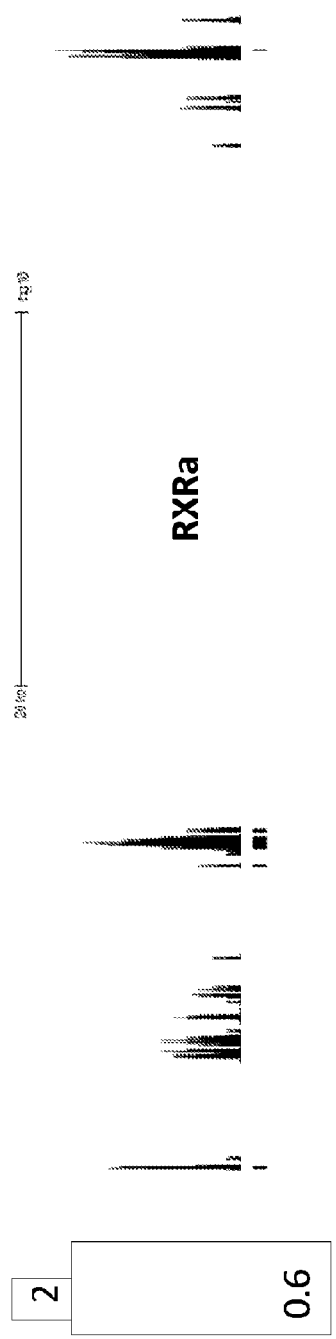
FIG. 10A
FIG. 10B

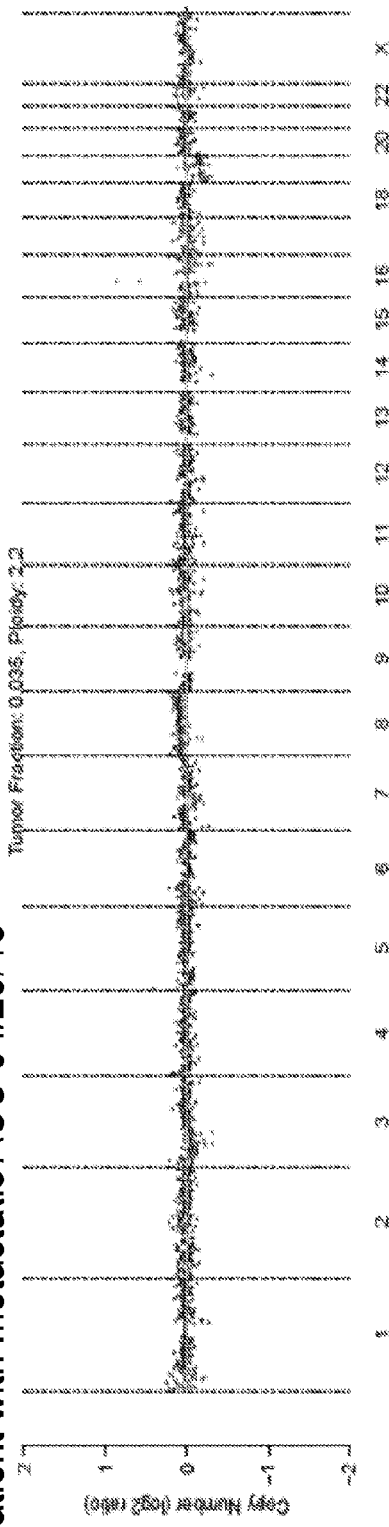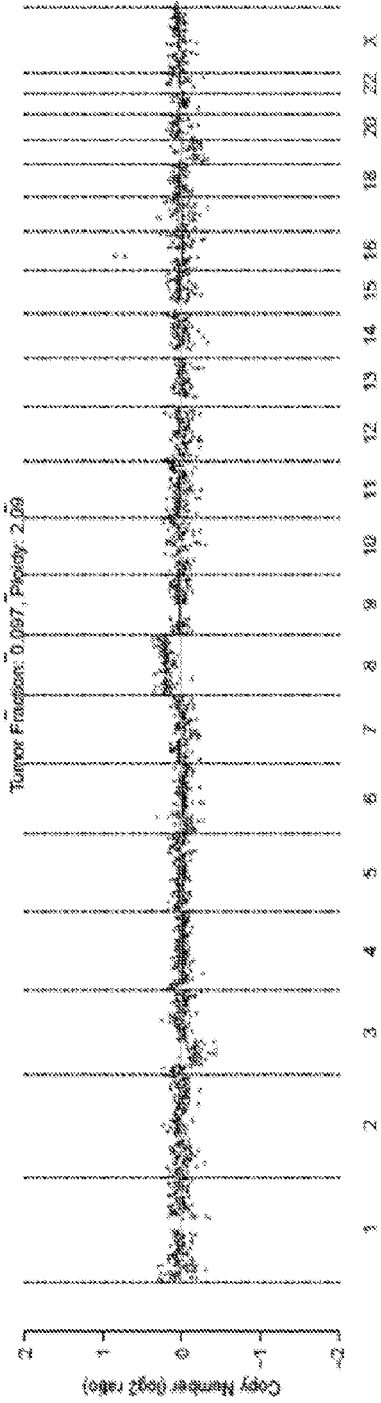
FIG. 28A
FIG. 28B 3 mg/ml Tretinoin; (TGI= 8%) most closely resembles the 32 mg/kg tretinoin dose.

METHODS FOR TREATMENT OF ADENOID CYSTIC CARCINOMA

CROSS REFERENCE TO RELATED APPLICATIONS

This application is a 35 U.S.C. § 371 National Phase Entry Application of International Application No. PCT/US2017/049861, filed Sep. 1, 2017, which designates the U.S. and which claims benefit under 35 U.S.C. § 119(e) of U.S. Provisional Application No. 62/383,230, filed Sep. 2, 2016, the contents of both of which are incorporated herein by reference in their entireties.

GOVERNMENT SUPPORT

This invention was made with Government support under grant no. R01 HL048801, P01 HL032262, P30 DK049216, R01 DK053298, U01 HL100001, R24 DK092760 awarded by the National Institutes of Health. The Government has certain rights in the invention.

SEQUENCE LISTING

The instant application contains a Sequence Listing which has been submitted electronically in ASCII format and is hereby incorporated by reference in its entirety. Said ASCII copy, created on Sep. 21, 2017, is named 701039-087921USPX_SL.txt and is 3,465 bytes in size.

TECHNICAL FIELD

The invention described herein relates to a method of treatment of Adenoid Cystic Carcinoma (ACC) comprising, selecting a subject in need of treatment for ACC and administering a therapeutically effective amount of a retinoic acid receptor agonist to the subject.

BACKGROUND

ACC is a malignant neoplasm that arises within the secretory glands, most commonly in the salivary glands of the head and neck, and is characterized by slow and unpredictable growth that is often fatal. ACC has a propensity to spread along nerve fibers and metastasize to other locations in the body. Recurrent MYB translocations have been identified in the majority of ACCs, which are characterized by overexpression of MYB and MYB targets. MYB is a master transcription factor with roles in proliferation and differentiation, and many of the ACC translocations involve another transcription factor, NFIB. Alterations in MYB have been implicated in a variety of cancers, including leukemia, pediatric gliomas, and cancers of the colon, breast and prostate. ACC-specific MYB translocations have been recently shown to promote transformation in genetically engineered mouse models.

Despite aggressive multimodality management, approximately half of ACC patients develop distant metastases, and up to one-third die within two years of diagnosis. No standard systemic chemotherapy regimen or approved drug therapy exists for recurrent or metastatic ACC, and no drug therapy has demonstrated either survival or progression-free survival benefit. Whole-exome sequencing of ACC tumors has revealed mutations in NOTCH and fibroblast growth factor signaling and chromatin remodeling genes, which could serve as potential therapeutic targets. However, over 30 phase II clinical trials since 1985 involving cytotoxic therapy or targeted therapies against c-Kit, epidermal growth factor receptor, fibroblast growth factor receptor, and mammalian target of rapamycin, among others, have not been successful. Activating NOTCH1 mutations occur in about 15% of ACCs, limiting the therapeutic use of Notch inhibitors. Hence, targeting MYB represents a desperately needed therapeutic strategy that has the potential to elicit broad clinical activity across many ACC tumors.

SUMMARY

In one aspect, the invention provides a method for treatment of adenoid cystic carcinoma (ACC) comprising: selecting a subject in need of treatment for ACC and administering a therapeutically effective amount of a retinoic acid receptor agonist to the subject. In some embodiments, the subject is having ACC or is at risk of having ACC and is not undergoing treatment for acute promyelocytic leukemia (APL). In some embodiments, the subject is having ACC or is at risk of having ACC, and is not having any other form of cancer.

In some embodiments of the invention described herein, the method further comprises administering a chemotherapy agent or an immunotherapy agent. In some preferred embodiments, the chemotherapy agent or the immunotherapy agent is selected from the group consisting of daunorubicin, idarubicin, cytarabine, arsenic trioxide and tamibarotene. In some embodiments, no other anti-cancer therapeutic agent is administered to the subject.

In another aspect, the invention provides a method for inhibiting expression of oncogenic transcription factor MYB in a cell, comprising: contacting a cell expressing MYB with a retinoic acid receptor agonist.

In yet another aspect, the invention described herein provides an assay for identifying a compound that modulates the expression or activity of MYB or MYBL1, the method comprising: contacting an embryonic cell with a test compound, wherein the cell comprises a reporter gene; and determining the amount of reporter gene expression after incubation with the test compound; wherein a change in the expression of the reporter gene relative to a control or reference indicates that the compound modulates the expression or activity of MYB or MYBL1.

BRIEF DESCRIPTION OF THE DRAWINGS

FIGS. 9A-9I are line graphs showing ACC xenotransplantation trials with retinoic acid agonists. ACC cells from three different human tumors—grade 2 tumors, ACCX6 (FIGS. 9A, 9D and 9G) and grade 3 tumors, ACCX9 (FIGS. 9B, 9E and 9H) and ACCX11 (FIGS. 9C, 9F and 9I)—were transplanted into the flanks of nude mice. Average tumor volume from about 5 mice per group was 88% for ATRA (FIGS. 9A-9C), 86% for isotretinoin (FIGS. 9D-9E) and 53% for fenretinide (FIGS. 9G-9I) during the period of the xenotransplantation trial.

FIGS. 10A and 10B are spectras showing RXR binding profile for the myb locus in K562 cells by ChIP-seq.

FIG. 28A-28D show serial whole genome sequencing of cell-free DNA from blood of ACC patient showing increasing tumor fraction correlating with clinical progression.

FIGS. 31A-31G are line graphs showing Tumor Growth Inhibition (TGI) in PDX model ACCx6 (FIGS. 31A and 31B), ACCx9 (FIGS. 31C and 31D), ACCx5M1 (FIGS. 31E and 31F) and ACCx11 (FIG. 31G). Results are from two different studies for ACCx6, ACCx9 and ACCx5M1 and one study for ACCx11.

DETAILED DESCRIPTION

Figure 1:
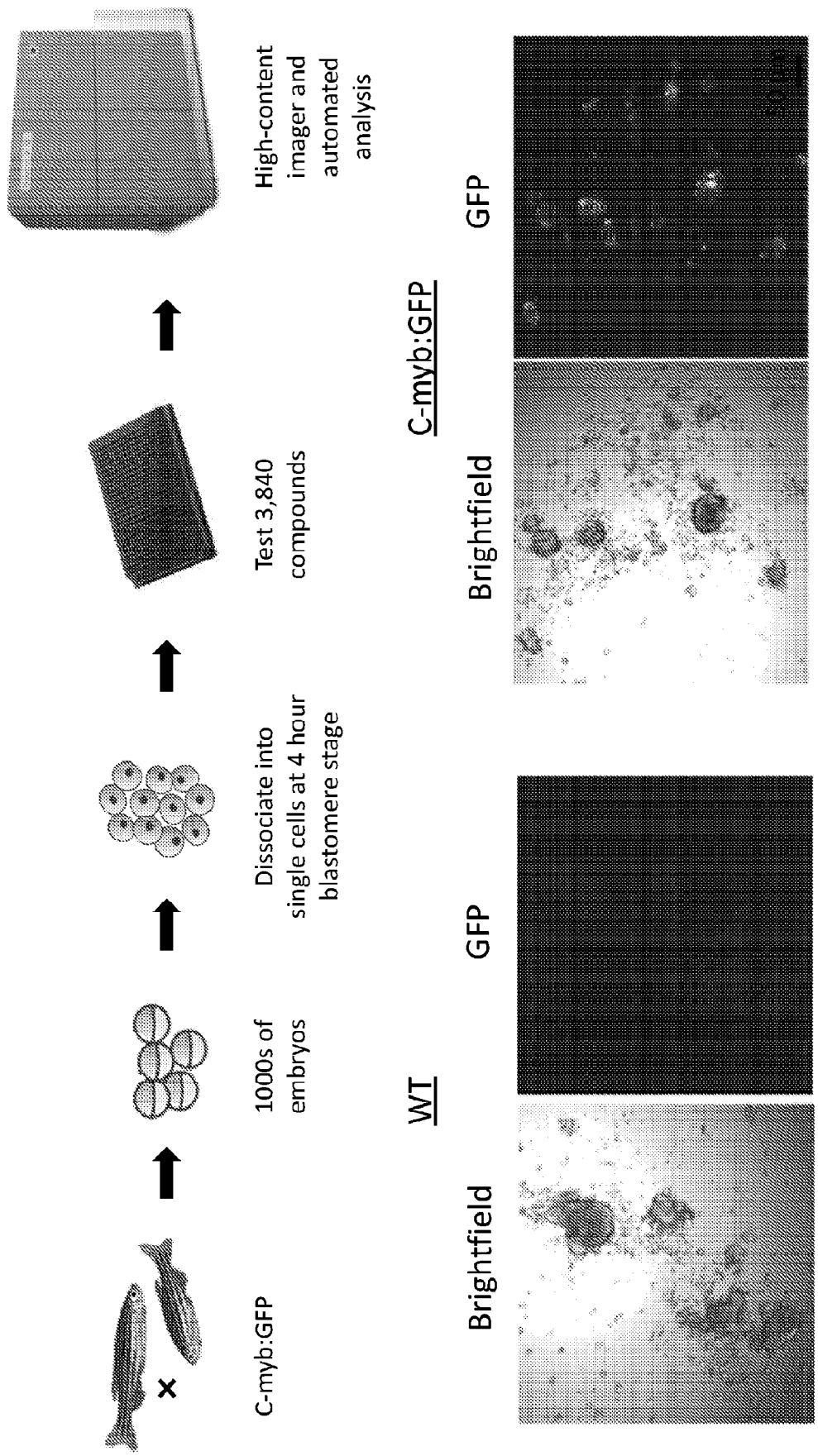
FIG. 1 is a schematic showing a high-throughput image-based chemical screening assay and sample images from the screen. Embryos from c-myb:GFP transgenic fish were collected and dissociated into single cells at approximately 4 hpf, plated individually with 3,840 compounds in duplicate, and imaged 2 days later for fluorescence.
Figure 2:
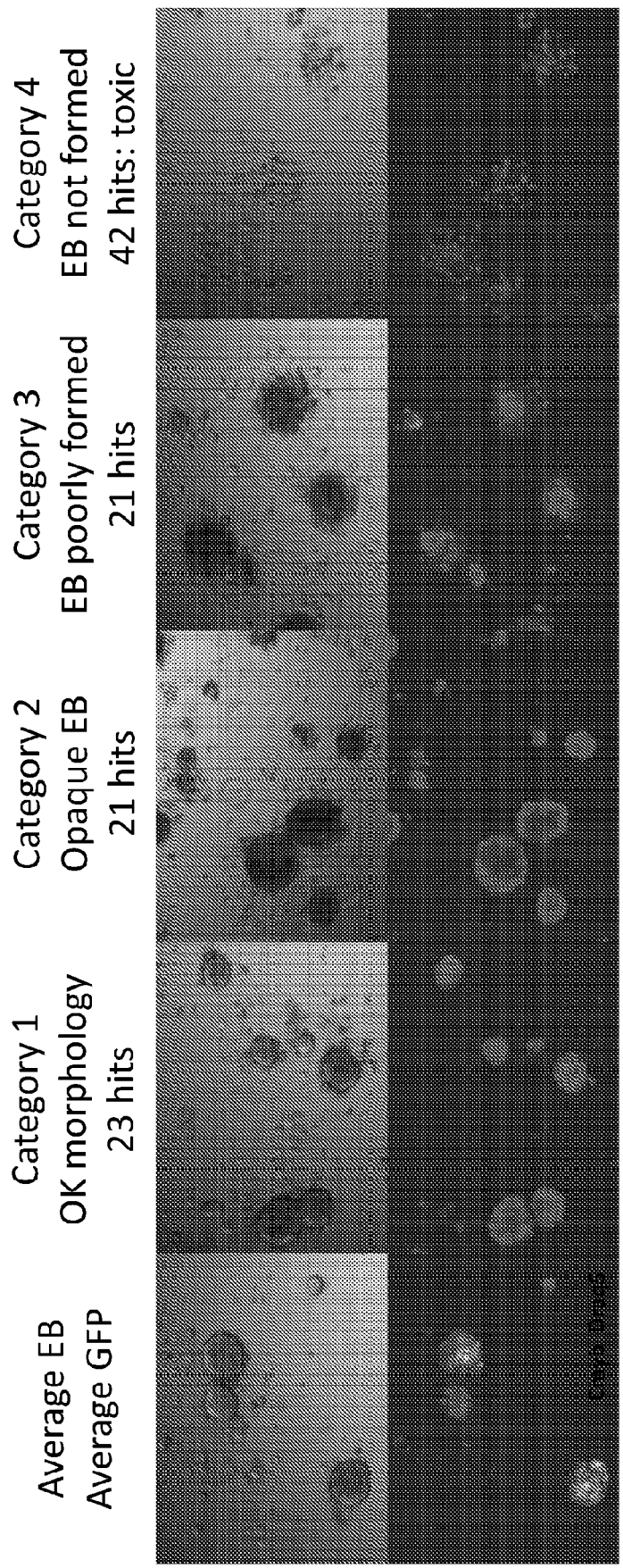
FIG. 2 is a representative image showing the hits found to downregulate c-myb:GFP zebrafish embryo cultures which were scored for morphology.
Figure 3:
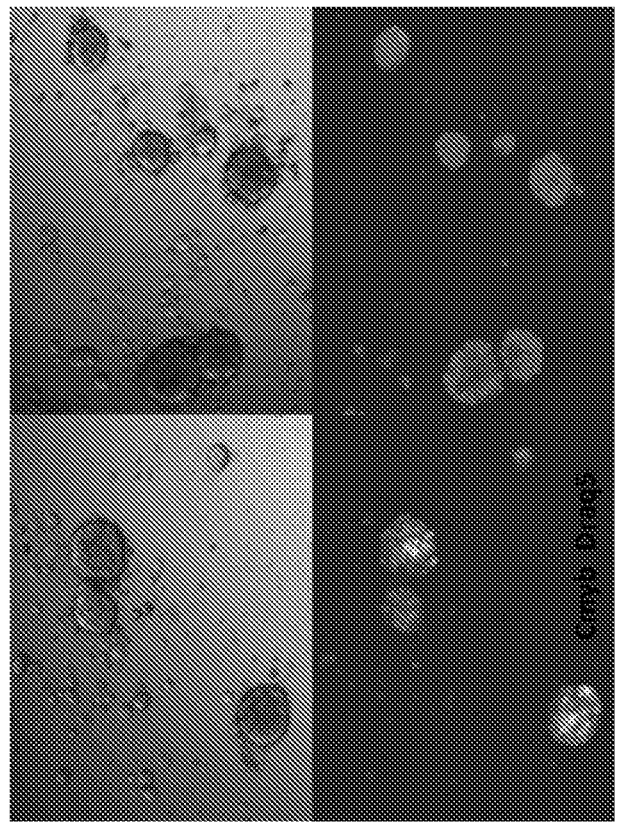
FIG. 3 shows several retinoic acid agonist derivatives that downregulate myb expression.
Figures 4A, 4B:
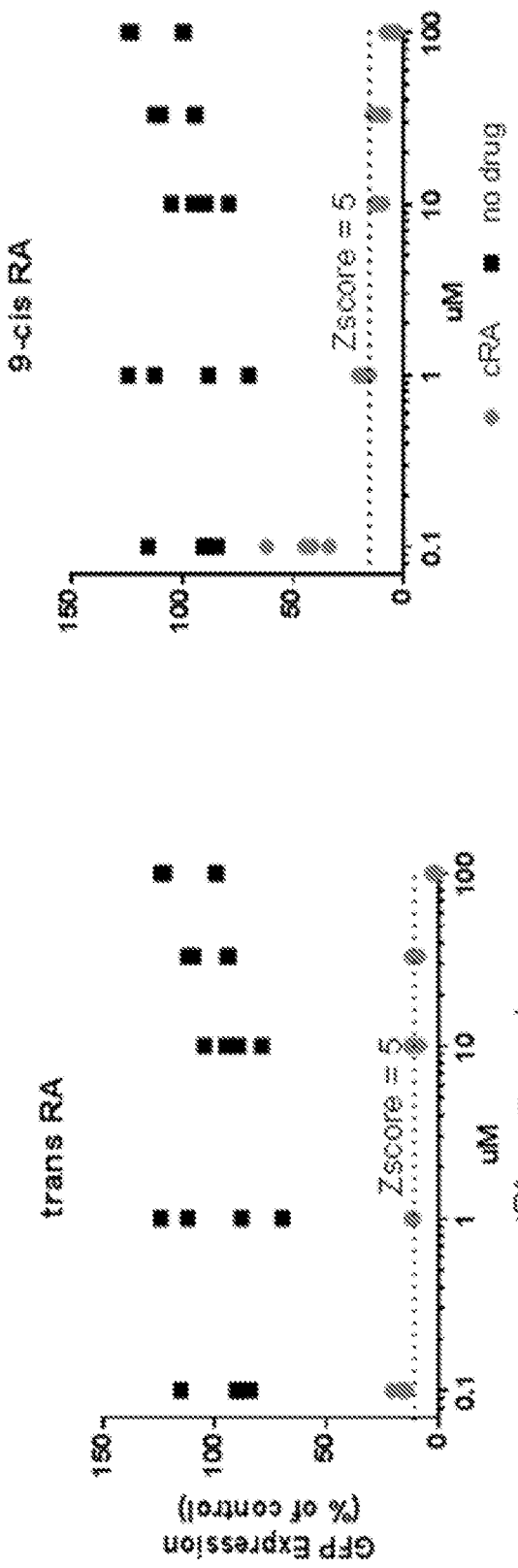
FIGS. 4A-4E are graphs showing dose response downregulation of c-myb:GFP cultures for retinoic acid agonists—trans retinoic acid (FIG. 4A), 9-cis-retinoic acid (FIG. 4B), p-hydroxyanilide (FIG. 4C), AM580 (FIG. 4D), TTNPB (FIG. 4e) and AC261066 (FIG. 4F).
Figures 4C, 4D:
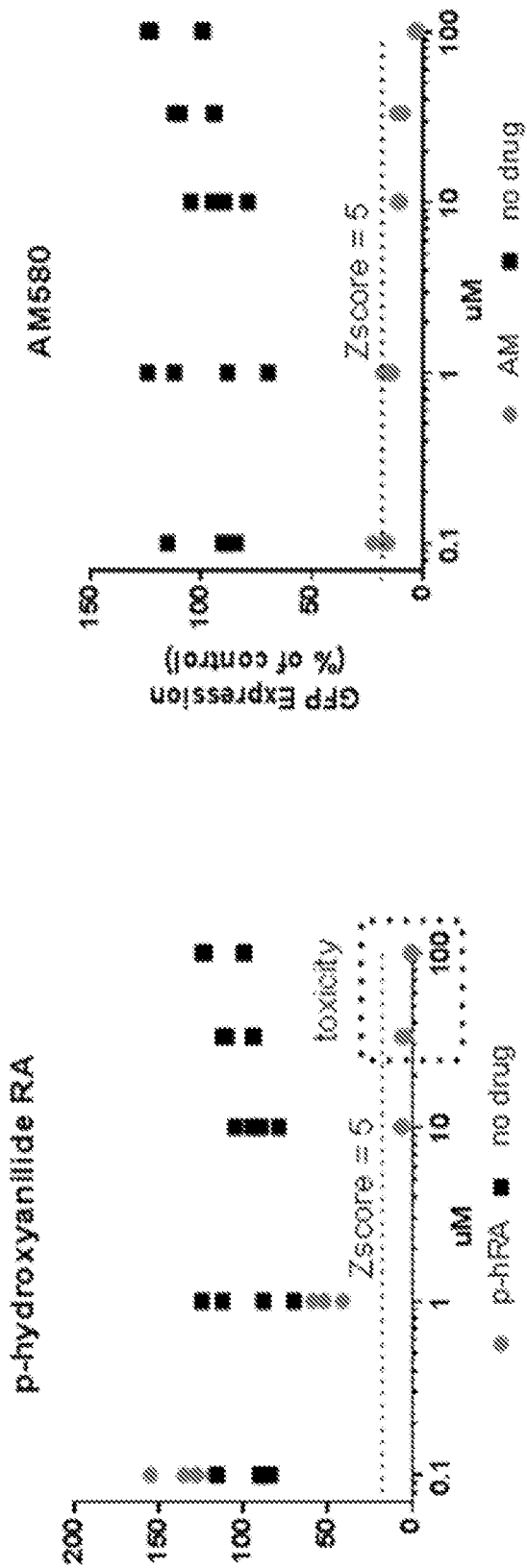
Figure 4F:
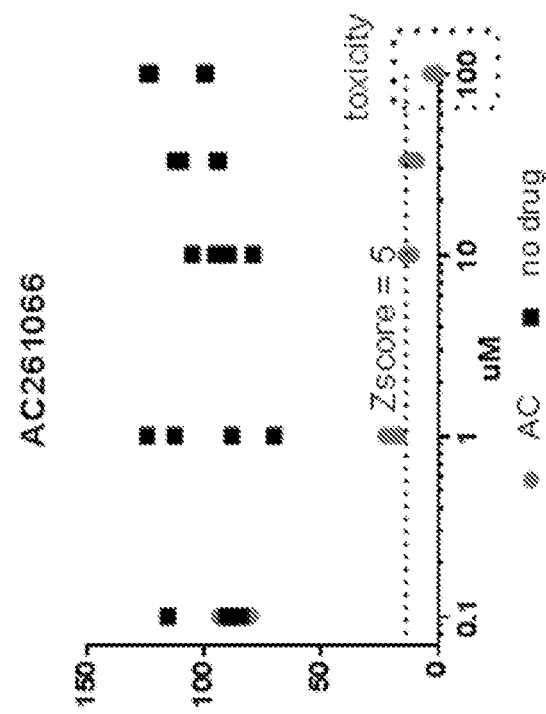
Figure 4E:
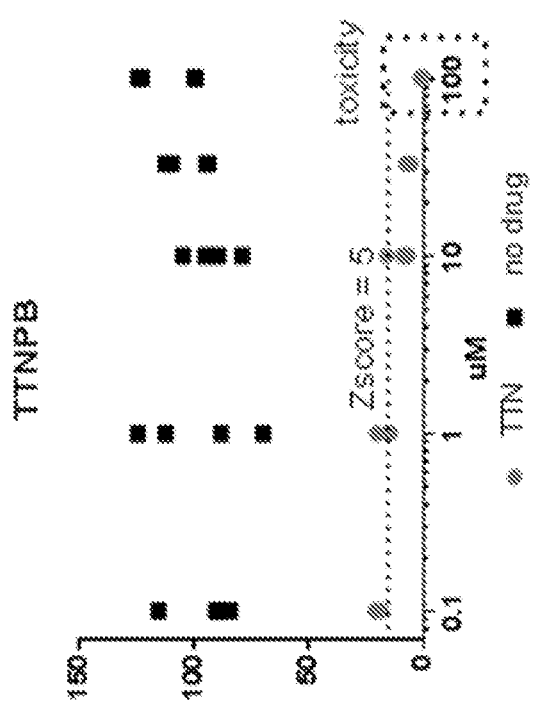

ACC is a form of malignant neoplasm which occurs in secretory glands. Most commonly, ACC arises at the salivary glands in the head and neck. Despite aggressive treatment, approximately fifty percent of the patients develop distant metastates and up to one third die within two years. Table 1 shows representative examples of Phase II trials performed in the last decade. Multiple phase II studies of targeted therapies in the last decade show minimal activity. Therefore, there is an unmet need to develop new therapies for the treatment of ACC.

TABLE 1

| Phase II Trials in ACC (1996-2015) | | |
| --- | --- | --- |
| Targeted Agent | Number of subjects | Objective Response Rate |
| Dovitinib (2015) | 32 | 3% |
| Sorafenib (2015) | 19 | 11% |
| Dasatinib (2015) | 40 | 3% |
| Everolimus (2014) | 31 | 0% |
| Vorinostat (2013) | 30 | 3% |
| Sunitinib (2012) | 13 | 0% |
| Cetuximab (2009) | 23 | 0% |
| Lapatinib (2006) | 19 | 0% |
| Bortezomib (2006) | 25 | 0% |
| Gefitinib (2005) | 19 | 0% |
| Imatinib (2005) | 15 | 0% |

The targeted agents described in Table 1 are all anticancer agents. For example, Sorafenib is used in the treatment of kidney, liver and thyroid cancer; Dasatinib is used for treating leukemia; Everolimus is used to treat cancer related to kidney, pancreas, breast and brain. However, as shown in Table 1, these targeted agents show little to no success in treating ACC. Therefore, one skilled in the art would not have a reasonable expectation that a drug used for the treatment of one type of cancer will be effective for the treatment of ACC or would provide a favorable result in the treatment of ACC.

In one aspect, the invention provides a method for treatment of adenoid cystic carcinoma (ACC) comprising: selecting a subject in need of treatment for ACC and administering a therapeutically effective amount of a retinoic acid receptor agonist to the subject.

One skilled in the art, for example a clinician, can diagnose ACC using standard methods. Early lesions associated with ACC of the salivary glands can appear as painless, usually slow-growing masses underneath the normal lining of the mouth or skin of the face. Non-limiting examples of symptoms associated with ACC include a lump on the palate, under the tongue, or in the bottom of the mouth, an abnormal area on the lining of the mouth, numbness of the upper jaw, palate, face, or tongue, difficulty swallowing, hoarseness, dull pain in jaw, a bump or nodule in front of the ear or underneath the jaw, and paralysis of a facial nerve.

To confirm the presence of ACC-associated tumors, one skilled in the art can perform a biopsy of a suspected area. As defined herein, a biopsy is the removal of a small amount of tissue for examination under a microscope. A biopsy can make a definite diagnosis of ACC. A biopsy can be performed for example, by using a fine needle biopsy or by surgically removing part or all of the tumor. A fine needle biopsy is also called fine needle aspiration or FNA. Typically, this procedure uses a thin needle to remove fluid and cells from the suspicious area. A trained pathologist can assess the biopsied tissue for distinct ACC characteristics, for example bundles of epithelial cells surround and/or infiltrate ducts or glandular structures within the organ.

As is known in the art, imaging techniques, primarily magnetic resonance imaging (MRI) or computed tomography (CT) scan, are used identifying the size and location of a tumor, for example prior to surgery or treatment. A positron emission tomography (PET) scan is useful in determining if a tumor has spread from its primary location to secondary locations.

An MRI utilizes magnetic fields to produce detailed images of the body. An MRI scan can be used to measure the tumor's size or identify growth of the tumor along nerve branches (perineural spread). A CT scan creates a 3-dimensional picture of the inside of the body using x-rays taken from different angles. A computer then combines these images into a detailed, cross-sectional view that shows any abnormalities or tumors. Optionally, a contrast medium (e.g., Gadolinium contrast medium) is administered prior to the MRI or CT scan before the scan to create a clearer image. The contrast medium is administered to a subject, for example by intravenous injection or orally. A PET scan generates pictures of organs and tissues inside the body. Typically, a PET scan combined with a CT scan, called a PET-CT scan. Prior to a PET scan, a subject is administered a small amount of radioactive sugar substance via intravenous injection. The radioactive sugar substance is taken up by the cancer cells and detected by PET imaging.

Recently sensitive techniques for "liquid biopsy" analysis to monitor circulating tumor DNA (ctDNA), and circulating tumor cells (CTCs) as a surrogate marker for tumor burden have been developed. This approach offers a valuable measurement for tumor response in addition to imaging studies. It has been demonstrated that tracking tumor-associated genetic aberrations in the blood can be used to assess residual disease or emergence of cancer cells resistant to the therapy. Moreover, monitoring of genetic alteration in the blood can be used to detect local recurrence or distant metastasis as early as 5-10 months before they are detectable by conventional imaging methods. These type of data are shown in the FIGS. 28A-28D, 29 and 30. Thus, ctDNA can be used as a biomarker of disease activity in ACC and response to therapy to determine whether retinoic acid affects the level of circulating tumor cells and/or circulating tumor DNA, and correlate with clinical response.

FIGS. 28A-28D, 29 and 30 show the use of "blood biopsy" to identify mechanisms of response and resistance to retinoic acid and identify prognostic biomarkers for good responders versus poor responders. Without wishing to be bound by a theory, in addition to establishing the role retinoic acid as a novel treatment in ACC, this also provides for simultaneous real-time tracking and identification of mechanisms of drug resistance. These data can reveal novel drug targets and impact the rational design of targeted treatment regimens in ACC. Thus the data shown can track and define the mechanisms of drug resistance with unprecedented resolution.

In some embodiments, a subject is selected for having a myb translocation. As described herein, a translocation of the gene myb resulting in the overexpression of the MYB protein is observed in approximately 75% of ACC tumors. As used herein, the term "gene translocation" refers to a chromosomal rearrangement resulting in a joining of otherwise-separated genes. A biological sample, for example a blood sample, a tissue biopsy, is analyzed for the presence or absence of gene amplification or translocation. One skilled in the art can use standard approaches to assess a biological sample for a myb translocation or MYB overexpression. Examples of methods that can be used for downstream analyses to characterize and/or analyze the biological sample include, but are not limited to, biochemical analysis; immunochemical analysis; image analysis; cytomorphological analysis; molecule analysis such as PCR, sequencing; genomics analysis; epigenomics analysis; transcriptomics analysis; and any combination thereof. In some embodiments, molecular features of the biological samples are analyzed by image analysis, PCR (including the standard and all variants of PCR), microarray (including, but not limited to DNA microarray, MMchips for microRNA, protein microarray, cellular microarray, antibody microarray, and carbohydrate array), sequencing, biomarker detection, or methods for determining DNA methylation or protein glycosylation pattern.

In some embodiments, protein expression level of MYB is determined. In some embodiments, RNA expression level of a cancer specific gene of the CTCs is determined. Examples of methods for determine protein expression level of MYB include, but are not limited to, PCR and all variations of PCR, western blot analysis, and RNA expression analysis.

In the previous publication Chen WT, et al. Effect of all-trans-retinoic acid on inhibition of human salivary adenoid cystic carcinoma cell proliferation in vitro, Chinese Journal of Oral Maxillofacial Surgery 1998, 8,12-14, it was alleged that all-trans-retinoic acid exhibits anti-proliferative effects on a human salivary adenoid cystic carcinoma cell. However, it has since been shown that the human salivary adenoid cystic carcinoma cell line used in this publication is not a bona fide adenoid cystic carcinoma cell line. Further, as seen from Table 1, there is no reasonable expectation of success for treating ACC based on in vitro data. Thus, one would not have a reasonable expectation that all-trans-retinoic acid would be effective in treating adenoid cystic carcinoma based on Chen's disclosure.

In some embodiments, the subject is having ACC or is at risk of having ACC and is not undergoing treatment for acute promyelocytic leukemia (APL). In some embodiments, the subject is having ACC or is at risk of having ACC, and is not having any other form of cancer.

It is widely known in the art that compounds having retinoid like activity are useful in treating a variety of disorders and conditions such as, but not limited to, dermatoses, acne, psoriasis, icthyosis, eczema, atopic dermatitis, epithelial cancer, for promoting wound healing and preventing the effects of sun damage to skin. In some embodiments of the invention described herein, the subject is not undergoing treatment requiring administration of retinoic acid receptor agonists.

As used herein, the term "retinoic acid", "retinoic acid agonists", "retinoic acid receptor agonists" or "retinoids" refer to naturally occurring compounds with vitamin A activity, synthetic analogs, and various metabolites thereof. The retinoids are a class of compounds consisting of four isoprenoid units joined in head-to-tail manner. Numerous retinoids have been identified, as described, for example, by Sporn, Roberts and Goodman in the two volume treatise entitled The Retinoids (Academic Press, N.Y., 1984). Exemplary retinoids include All trans Retinoic acid, 13-cis-retinoic acid (isotretinoin), 4-[(5,6,7,8-Tetrahydro-5,5,8,8-tetramethyl-2-naphthalenyl)carboxamido]benzoic acid (AM- 580), 9-cis retinoic acid, retinoic acid p-hydroxyanilide (Fenretinide), 4-[(1,1,4,4-tetramethyltetralin-6-yl)carbamoyl]benzoic acid (tamibarotene), 4-[(E)-2-(5,6,7,8-Tetrahydro-5,5,8,8-tetramethyl-2-naphthalenyl)-1-propenyl]benzoic acid (TTNPB), and 4-[4-(2-Butoxyethoxy-)-5-methyl-2-thiazolyl]-2-fluorobenzoic acid (AC 261066), retinol, retinyl acetate, retinyl hexadecanoate, α-retinyl, 4,14-retroretinol, deoxyretinol, anhydroretinol, 3,4-didehydroretinol, 15,15-dimethyl retinol, retinyl methyl ether, retinyl phosphate, mannosyl retinyl phosphate, retinol thioacetate, retinal (retinaldehyde), 3,4-didehydroretinal, retinylidene acetylacetone, retinylidene-1,3-cyclopentanedione, retinal oxime, retinaldehyde acetylhydrazone, retinoic acid, 4-hydroxyretinoic acid, 4-oxoretinoic acid, 5,6-dihydroretinoic acid, 5,6-epoxyretinoic acid, 5,8-epoxyretinoic acid, the open-chain C20 analog of retinoic acid (i.e., (all-E -3,7,11, 15-tetramethyl-2,4,6,8,10,12,14-hexadecaheptaenoic acid), 7,8-didehydroretinoic acid, 7,8-dihydroretinoic acid, "Acid" (E, E)-3-methyl-5-(2,6,6-trimethyl-2-cyclohexen-1-yl)-2,4-pentanedioic acid), "C17 Acid" ((E,E,E)-5-methyl-7-(2,6,6-trimethyl-1-cyclohexen-1-yl) -2,4,6-hepatrienoic acid), "C22 Acid" (14'-apo-γ, Ψ-carotenoic acid), retinoic acid esters (e.g., methyl ester, ethyl ester, etc.), retinoic acid ethylamide, retinoic acid 2-hydroxyethylamide, methyl retinone, "C18 Ketone" 6-methyl-8-(2,6,6-trimethyl-1-cyclohexen-1-yl)-3,5,7-ocatrien-2-one), and the like. The terms "retinoic acid", "retinoic acid agonists", "retinoic acid receptor agonists" or "retinoids" have been used interchangeably herein.

In some embodiments of this and other aspects of the invention, the method comprises administering at least one retinoid such as retinoic acid and derivatives and analogs thereof.

As used herein, the term "administer" refers to the placement of a composition into a subject by a method or route which results in at least partial localization of the composition at a desired site such that desired effect is produced. An agonist described herein can be administered by any appropriate route known in the art including, but not limited to, oral or parenteral routes, including intravenous, intramuscular, subcutaneous, transdermal, airway (aerosol), pulmonary, nasal and rectal administration. The preferred mode of administration in some embodiments of the invention is in the oral form. In some embodiments, said administering of agonist to the subject excludes topical administration.

The preferred retinoic acid receptor agonists are all-trans retinoic acid (ATRA), 13-cis-retinpoic acid (isotretinoin), Tamibarotene, 4-[(5,6,7,8-Tetrahydro-5,5,8,8-tetramethyl-2-naphthalenyl)carboxamido]benzoic acid (AM-580), 9-cis retinoic acid, retinoic acid p-hydroxyanilide (Fenretinide), 4-[(E)-2-(5,6,7,8-Tetrahydro-5,5,8,8-tetramethyl-2-naphthalenyl)-1-propenyl]benzoic acid (TTNPB), and 4-[4-(2-Butoxyethoxy-)-5-methyl-2-thiazolyl]-2-fluorobenzoic acid (AC 261066). The more preferred retinoic acid receptor agonist for use in some embodiments of the invention is all-trans-retinoic acid ((E)-3,7-dimethyl-9-(2,6,6-trimethyl-1-cyclo-hexen-1-yl)-2,4,6,8-nonatetraenoic acid)).

For administration to a subject, the retinoic acid receptor agonists described herein can be provided in pharmaceutically acceptable compositions. These pharmaceutically acceptable compositions comprise a therapeutically-effective amount of one or more of the retinoic acid receptor agonists described herein, formulated together with one or more pharmaceutically acceptable carriers (additives) and/or diluents. As described in detail below, the pharmaceutical compositions of the present invention can be specially formulated for administration in solid or liquid form, including those adapted for the following: (1) oral administration, for example, drenches (aqueous or non-aqueous solutions or suspensions), lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous or epidural injection as, for example, a sterile solution or suspension, or sustained-release formulation; (3) intravaginally or intrarectally, for example, as a pessary, cream or foam; (4) sublingually; (5) ocularly; (6) transdermally; (7) transmucosally; or (8) nasally. Additionally, the retinoic acid receptor agonists can be implanted into a patient or injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. No. 3,773,919; and U.S. Pat. No. 35 3,270,960.

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Amount of the retinoic acid receptor agonist/agonists in the pharmaceutical composition can be based on weight, moles, or volume. In some embodiments, the pharmaceutical composition comprises at least 0.0001% retinoic acid receptor agonist. In some embodiments, the pharmaceutical composition comprises at least 0.1% retinoic acid receptor agonist. In some embodiments, the pharmaceutical composition comprises at least 0.5% retinoic acid receptor agonist of the invention. In some embodiments, the pharmaceutical composition comprises at least 1% retinoic acid receptor agonist. In some embodiments, the pharmaceutical composition comprises at least 2% retinoic acid receptor agonist. In some embodiments, the pharmaceutical composition comprises at least 3% retinoic acid receptor agonist. In some embodiments, the pharmaceutical composition comprises at least 4% retinoic acid receptor agonist. In some embodiments, the pharmaceutical composition comprises at least 5% retinoic acid receptor agonist. In some embodiments, the pharmaceutical composition comprises at least 10% retinoic acid receptor agonist. In some embodiments, the pharmaceutical composition comprises 0.01%-99% of the retinoic acid receptor agonist. In some embodiments, the pharmaceutical composition comprises 0.05%-90% of the retinoic acid receptor agonist. In some embodiments, the pharmaceutical composition comprises 0.1%-85% of the retinoic acid receptor agonists. In some embodiments, the pharmaceutical composition comprises 0.5%-80% of the retinoic acid receptor agonists. In some embodiments, the pharmaceutical composition comprises 1%-75% of the retinoic acid receptor agonists. In some embodiments, the pharmaceutical composition comprises 2%-70% of the retinoic acid receptor agonists. In some embodiments, the pharmaceutical composition comprises 3%-65% of the retinoic acid receptor agonists. In some embodiments, the pharmaceutical composition comprises 4%-60% of the retinoic acid receptor agonists. In some embodiments, the pharmaceutical composition comprises 5%-50% of the retinoic acid receptor agonists.

It will also be appreciated that certain of the retinoic acid receptor agonists can exist in free form for treatment, or where appropriate, as a pharmaceutically acceptable derivative thereof. According to the present invention, a pharmaceutically acceptable derivative includes, but is not limited to, pharmaceutically acceptable salts, esters, salts of such esters, or a pro-drug or other adduct or derivative of a retinoic acid receptor agonist which upon administration to a patient in need is capable of providing, directly or indirectly, a compound as otherwise described herein, or a metabolite or residue thereof.

As described above, the pharmaceutical compositions of the present invention optionally comprise a pharmaceutically acceptable excipient, which, as used herein, includes any and all solvents, diluents, or other liquid vehicle, dispersion or suspension aids, surface active agents, isotonic agents, thickening or emulsifying agents, preservatives, antioxidants, solid binders, lubricants, and the like, as suited to the particular dosage form desired.

As used here, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (24) C2-C12 alcohols, such as ethanol; and (25) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

Useful pharmaceutical carriers for the preparation of the compositions hereof, can be solids, liquids or gases. Suitable pharmaceutical carriers and their formulation are described in Remington's Pharmaceutical Sciences by E. W. Martin. Such compositions will, in any event, contain an effective amount of the retinoic acid receptor agonist together with a suitable carrier so as to prepare the proper dosage form for proper administration to the recipient.

Liquid dosage forms for oral administration include, but are not limited to, pharmaceutically acceptable emulsions, microemulsions, solutions, suspensions, syrups and elixirs. In addition to the retinoic acid receptor agonists, the liquid dosage forms can contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Solid dosage forms for oral administration include capsules, tablets, pills, powders, and granules. In such solid dosage forms, the retinoic acid receptor agonist is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcelhdose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monosteamte, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form can also comprise buffering agents.

Solid compositions of a similar type can also be employed as fillers in soft and hard-filled gelatin capsules using such excipients as lactose or milk sugar as well as high molecular weight polyethylene glycols, and the like. The solid dosage forms of tablets, dragees, capsules, pills, and granules can be prepared with coatings and shells such as enteric coatings and other coatings well known in the pharmaceutical formulating art. They can optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type can also be employed as fillers in soft and hard-filled gelatin capsules using such excipients as lactose or milk sugar as well as high molecular weight polethylene glycols, and the like.

The retinoic acid receptor agonists can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the retinoic acid receptor agonists can be admixed with at least one inert diluent such as sucrose, lactose and starch. Such dosage forms can also comprise, as in normal practice, additional substances other than inert diluents, e.g., tableting lubricants and other tableting aids such as magnesium stearate and microcrystalline cellulose. In the case of capsules, tablets and pills, the dosage forms can also comprise buffering agents. They can optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Formulations suitable for parenteral administration conveniently include sterile aqueous preparations of the agents that are preferably isotonic with the blood of the recipient. Suitable excipient solutions include phosphate buffered saline, saline, water, lactated Ringer's or dextrose (5% in water). Such formulations can be conveniently prepared by admixing the agent with water to produce a solution or suspension, which is filled into a sterile container and sealed against bacterial contamination. Preferably, sterile materials are used under aseptic manufacturing conditions to avoid the need for terminal sterilization. Such formulations can optionally contain one or more additional ingredients, which can include preservatives such as methyl hydroxybenzoate, chlorocresol, metacresol, phenol and benzalkonium chloride. Such materials are of special value when the formulations are presented in multidose containers.

Buffers can also be included to provide a suitable pH value for the formulation. Suitable buffer materials include sodium phosphate and acetate. Sodium chloride or glycerin can be used to render a formulation isotonic with the blood.

If desired, a formulation can be filled into containers under an inert atmosphere such as nitrogen and can be conveniently presented in unit dose or multi-dose form, for example, in a sealed ampoule.

Those skilled in the art will be aware that the amounts of the various components of the compositions of the invention to be administered in accordance with the method of the invention to a subject will depend upon those factors noted above.

Injectable preparations, for example, sterile injectable aqueous or oleaginous suspensions can be formulated according to the known art using suitable dispersing or wetting agents and suspending agents. The sterile injectable preparation can also be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable media prior to use.

In order to prolong the effect of a drug, it is often desirable to slow the absorption of the drug from subcutaneous or intramuscular injection. This can be accomplished by the use of a liquid suspension or crystalline or amorphous material with poor water solubility. The rate of absorption of the drug then depends upon its rate of dissolution that, in turn, can depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include (poly(orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the retinoic acid receptor agonists with suitable non-irritating excipients or carriers such as cocoa butter, polyethylene glycol, or a suppository wax which are solid at ambient temperature but liquid at body temperature and therefore melt in the rectum or vaginal cavity and release the active compound.

A typical suppository formulation includes the compound or a pharmaceutically acceptable salt thereof which is active when administered in this way, with a binding and/or lubricating agent, for example, polymeric glycols, gelatins, cocoa-butter, or other low melting vegetable waxes or fats. Typical transdermal formulations include a conventional aqueous or nonaqueous vehicle, for example, a cream, ointment, lotion, or paste or are in the form of a medicated plastic, patch or membrane.

Typical compositions for inhalation are in the form of a solution, suspension, or emulsion that can be administered in the form of an aerosol using a conventional propellant such as dichlorodifluoromethane or trichlorofluoromethane.

In some embodiments, ATRA is administered orally at a dose of 45 mg/m$^2$ per day in two equally divided doses each day (as is currently approved for treatment in acute promyelocytic leukemia). Each cycle can be 28 days. Eligible trial patients can include patients with unresectable, advanced ACC with clinical or radiographic disease progression (progression by RECIST not required) over the past 12 months, and any number of prior lines of therapy can enroll.

The phrase "therapeutically-effective amount" as used herein means that amount of a compound, material, or composition comprising a retinoic acid receptor agonist which is effective for producing some desired therapeutic effect in at least a sub-population of cells in an animal at a reasonable benefit/risk ratio applicable to any medical treatment. For example, an amount of the retinoic acid receptor agonist administered to a subject that is sufficient to produce a statistically significant, measurable change in at least one symptom of adenoid cystic carcinoma or metastasis.

The amount of the retinoic acid receptor agonist described herein that can be combined with a carrier material to produce a single dosage form will generally be that amount of the compound that produces a therapeutic effect. Generally out of one hundred percent, this amount will range from about 0.01% to 99% of the retinoic acid receptor agonist, preferably from about 5% to about 70%, most preferably from 10% to about 30%.

Toxicity and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compositions that exhibit large therapeutic indices, are preferred.

As used herein, the term ED denotes effective dose and is used in connection with animal models. The term EC denotes effective concentration and is used in connection with in vitro models.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized.

The therapeutically effective dose can be estimated initially from cell culture assays. A dose may be formulated in animal models to achieve a circulating plasma concentration range that includes the IC50 (i.e., the concentration of the therapeutic which achieves a half-maximal inhibition of symptoms) as determined in cell culture. Levels in plasma may be measured, for example, by high performance liquid chromatography. The effects of any particular dosage can be monitored by a suitable bioassay.

Determination of a therapeutically effective amount is well within the capability of those skilled in the art. Generally, a therapeutically effective amount can vary with the subject's history, age, condition, sex, as well as the severity and type of the medical condition in the subject, and administration of other pharmaceutically active agents. The dose of the retinoic acid receptor agonists disclosed herein depends on a number of factors, such as, for example, the manner of administration, the age and the body weight of the subject, and the condition of the subject to be treated, and ultimately will be decided by the attending physician or veterinarian. Such an amount of the retinoic acid receptor agonist as determined by the attending physician or veterinarian is referred to herein, and in the claims, as a "therapeutically effective amount".

The dosage can be determined by a physician and adjusted, as necessary, to suit observed effects of the treatment. Generally, the dose of the retinoic acid receptor agonist described herein is typically in the range of about 1 to about 1000 mg per day. Preferably, the therapeutically effective amount is in an amount of from about 1 mg to about 500 mg per day. For example, the compositions are administered so that the retinoic acid receptor agonist described herein is given at a dose from 1 µg/kg to 150 mg/kg, 1 µg/kg to 100 mg/kg, 1 µg/kg to 50 mg/kg, 1 µg/kg to 20 mg/kg, 1 µg/kg to 10 mg/kg, 1 µg/kg to 1 mg/kg, 100 µg/kg to 100 mg/kg, 100 µg/kg to 50 mg/kg, 100 µg/kg to 20 mg/kg, 100 µg/kg to 10 mg/kg, 100 µg/kg to 1 mg/kg, 1 mg/kg to 100 mg/kg, 1 mg/kg to 50 mg/kg, 1 mg/kg to 20 mg/kg, 1 mg/kg to 10 mg/kg, 10 mg/kg to 100 mg/kg, 10 mg/kg to 50 mg/kg, or 10 mg/kg to 20 mg/kg. It is to be understood that ranges given here include all intermediate ranges, for example, the range 1 mg/kg to 10 mg/kg includes 1 mg/kg to 2 mg/kg, 1 mg/kg to 3 mg/kg, 1 mg/kg to 4 mg/kg, 1 mg/kg to 5 mg/kg, 1 mg/kg to 6 mg/kg, 1 mg/kg to 7 mg/kg, 1 mg/kg to 8 mg/kg, 1 mg/kg to 9 mg/kg, 2 mg/kg to 10 mg/kg, 3 mg/kg to 10 mg/kg, 4 mg/kg to 10 mg/kg, 5 mg/kg to 10 mg/kg, 6 mg/kg to 10 mg/kg, 7 mg/kg to 10 mg/kg, 8 mg/kg to 10 mg/kg, 9 mg/kg to 10 mg/kg, and the like. It is to be further understood that the ranges intermediate to the given above are also within the scope of this invention, for example, in the range 1 mg/kg to 10 mg/kg, dose ranges such as 2 mg/kg to 8 mg/kg, 3 mg/kg to 7 mg/kg, 4 mg/kg to 6 mg/kg, and the like.

In some preferred embodiments, the retinoic acid receptor agonist is administered orally. In some embodiments of this and other aspects of the invention, the retinoic acid receptor agonist is administered in a single dose. In some embodiments, the retinoic acid receptor agonist is administered in two or more doses.

In some embodiments of the invention described herein, the retinoic acid receptor agonist is administered at a dose ranging from 10-40 mg/kg. In some embodiments, the retinoic acid receptor agonist is administered at a dose 20 mg/kg. In some embodiments, the agonist is administered in 3 mg/kg dose. In some embodiments, the agonist is administered in 4 mg/kg dose. In some embodiments, the agonist is administered in 30 mg/kg dose. In some embodiments, the agonist is administered in 40 mg/kg dose. In some preferred embodiments, ATRA is administered at a dose ranging from 8 mg/kg to 32 mg/kg. In some embodiments, tamibarotene is administered in 2 mg/kg dose. These have all showed tumor growth inhibition in the PDX studies. In some embodiments, ATRA can be dosed in humans at a split dose of 45 mg/m2 per day, which is the clinically approved dose for acute promyelocytic leukemia patients.

In some embodiments, the compositions are administered at a dosage so that the retinoic acid receptor agonist or a metabolite thereof has an in vivo concentration of less than 500 nM, less than 400 nM, less than 300 nM, less than 250 nM, less than 200 nM, less than 150 nM, less than 100 nM, less than 50 nM, less than 25 nM, less than 20, nM, less than 10 nM, less than 5 nM, less than 1 nM, less than 0.5 nM, less than 0.1 nM, less than 0.05 nM, less than 0.01, nM, less than 0.005 nM, less than 0.001 nM after 15 mins, 30 mins, 1 hr, 1.5 hrs, 2 hrs, 2.5 hrs, 3 hrs, 4 hrs, 5 hrs, 6 hrs, 7 hrs, 8 hrs, 9 hrs, 10 hrs, 11 hrs, 12 hrs or more of time of administration. In some specific examples, all trans retinoic acid is administered at a split dose of 45 mg/m$^2$ per day.

With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment or make other alteration to treatment regimen. The dosing schedule can vary from once a week to daily depending on a number of clinical factors, such as the subject's sensitivity to the retinoic acid agonist receptor. The desired dose can be administered everyday or every third, fourth, fifth, or sixth day. The desired dose can be administered at one time or divided into subdoses, e.g., 2-4 subdoses and administered over a period of time, e.g., at appropriate intervals through the day or other appropriate schedule. Such sub-doses can be administered as unit dosage forms. In some embodiments of the aspects described herein, administration is chronic, e.g., one or more doses daily over a period of weeks or months. Examples of dosing schedules are administration daily, twice daily, three times daily or four or more times daily over a period of 1 week, 2 weeks, 3 weeks, 4 weeks, 1 month, 2 months, 3 months, 4 months, 5 months, or 6 months or more.

The efficacy of a composition as described herein in, e.g. the treatment of Adenoid Cystic Carcinoma, or to induce a response as described herein can be determined by the skilled clinician. However, a treatment is considered "effective treatment," as the term is used herein, if one or more of the signs or symptoms of the ACC are altered in a beneficial manner, other clinically accepted symptoms are improved, or even ameliorated, or a desired response is induced e.g., by at least 10% following treatment according to the methods described herein. Efficacy can be assessed, for example, by measuring a marker, indicator, symptom, and/or the incidence of ACC treated according to the methods described herein or any other measurable parameter appropriate, e.g.

tumor size and/or growth. Efficacy can also be measured by a failure of an individual to worsen as assessed by hospitalization, or need for medical interventions (i.e., progression of ACC is halted). Methods of measuring these indicators are known to those of skill in the art and/or are described herein. Treatment includes any treatment of ACC in an individual or an animal (some non-limiting examples include a human or an animal) and includes: (1) inhibiting ACC, e.g., preventing a worsening of symptoms (e.g. pain or inflammation); or (2) relieving the severity of ACC, e.g., causing regression of symptoms. An effective amount for the treatment of ACC means that amount which, when administered to a subject in need thereof, is sufficient to result in effective treatment as that term is defined herein, for that disease. Efficacy can be assessed in animal models of a condition described herein, for example treatment of ACC. When using an experimental animal model, efficacy of treatment is evidenced when a statistically significant change in a marker is observed, e.g. a decreased in tumor size and/or growth.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder, specifically ACC. The term "treating" includes reducing or alleviating at least one adverse effect or symptom of ACC. Treatment is generally "effective" if one or more symptoms or clinical markers are reduced. Alternatively, treatment is "effective" if the progression of ACC is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of ACC, stabilized (i.e., not worsening) state of disease, delay or slowing of disease progression, amelioration or palliation of the disease state, remission (whether partial or total), and/or decreased mortality, whether detectable or undetectable. The term "treatment" of ACC also includes providing relief from the symptoms or side-effects of the disease.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g. the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase", "enhance", or "activate" are all used herein to mean an increase by a statically significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, an "increase" is a statistically significant increase in such level.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments, the subject is a mammal, e.g., a primate, e.g., a human. The terms, "patient" and "subject" are used interchangeably herein.

Preferably, the subject is a mammal. The mammal can be a human, non-human primate, mouse, rat, dog, cat, horse, or cow, but are not limited to these examples. Mammals other than humans can be advantageously used as subjects that represent animal models of disorders associated with inflammation.

In addition, the methods described herein can be used to treat domesticated animals and/or pets. A subject can be male or female. A subject can be one who has been previously diagnosed with or identified as suffering from or having ACC or metastasis, but need not have already undergone treatment.

A subject can be one who has been previously diagnosed with or identified as suffering from or having a condition in need of treatment for ACC or one or more complications related to such a condition, and optionally, have already undergone treatment for ACC or one or more complications related to ACC. Alternatively, a subject can also be one who has not been previously diagnosed as having ACC or one or more complications related to ACC. For example, a subject can be one who exhibits one or more risk factors for ACC or one or more complications related to ACC or a subject who does not exhibit risk factors.

A "subject in need" of treatment for a particular condition can be a subject having that condition, diagnosed as having that condition, or at risk of developing that condition.

In one aspect of the present invention, pharmaceutical compositions comprise one or more of the retinoic acid receptor agonists (or a prodrug, pharmaceutically acceptable salt, or other pharmaceutically acceptable form thereof), and optionally a pharmaceutically acceptable excipient. In certain embodiments, these compositions optionally further comprise one or more additional therapeutic agents. Alternatively, the retinoic acid receptor agonist can be administered to a patient in need thereof in combination with the administration of one or more other therapeutic agents.

In some embodiments of the invention described herein, the method further comprises administering a chemotherapy agent or an immunotherapy agent.

As used herein the term "chemotherapeutic agent" refers to any chemical or biological agent with therapeutic usefulness in the treatment of diseases characterized by abnormal cell growth. Such diseases include tumors, neoplasms and cancer as well as diseases characterized by hyperplastic growth. These agents can function to inhibit a cellular activity upon which the cancer cell depends for continued proliferation. In some aspect of all the embodiments, a chemotherapeutic agent is a cell cycle inhibitor or a cell division inhibitor. Categories of chemotherapeutic agents that are useful in the methods of the invention include alkylating/alkaloid agents, antimetabolites, hormones or hormone analogs, and miscellaneous antineoplastic drugs. Most of these agents are directly or indirectly toxic to cancer cells. In one embodiment, a chemotherapeutic agent is a radioactive molecule. One of skill in the art can readily identify a chemotherapeutic agent of use (e.g. see Slapak and Kufe, Principles of Cancer Therapy, Chapter 86 in Harrison's Principles of Internal Medicine, 14th edition; Perry et al. , Chemotherapy, Ch. 17 in Abeloff, Clinical Oncology 2nd ed. 2000 Churchill Livingstone, Inc; Baltzer L, Berkery R (eds): Oncology Pocket Guide to Chemotherapy, 2nd ed. St. Louis, Mosby-Year Book, 1995; Fischer D S, Knobf M F, Durivage H J (eds): The Cancer Chemotherapy Handbook, 4th ed. St. Louis, Mosby-Year Book, 1993). In some embodiments, the chemotherapeutic agent can be a cytotoxic chemotherapeutic. The term "cytotoxic agent" as used herein refers to a substance that inhibits or prevents the function of cells and/or causes destruction of cells. The term is intended to include radioactive isotopes (e.g. At211, I131, I125, Y90, Re186, Re188, Sm153, Bi212, P32 and radioactive isotopes of Lu), chemotherapeutic agents, and toxins, such as small molecule toxins or enzymatically active toxins of bacterial, fungal, plant or animal origin, including fragments and/or variants thereof.

The term chemotherapeutic agent is a broad one covering many chemotherapeutic agents having different mechanisms of action. Generally, chemotherapeutic agents are classified according to the mechanism of action. Many of the available agents are antimetabolites of development pathways of various tumors, or react with the DNA of the tumor cells. There are also agents which inhibit enzymes, such as topoisomerase I and topoisomerase II, or which are antimiotic agents.

Chemotherapeutic agents include, but are not limited to, an aromatase inhibitor; an antiestrogen, an anti-androgen (especially in the case of prostate cancer) or a gonadorelin agonist; a topoisomerase I inhibitor or a topoisomerase II inhibitor; a microtubule active agent, an alkylating agent, an anti-neoplastic anti-metabolite or a platin compound; a compound targeting/decreasing a protein or lipid kinase activity or a protein or lipid phosphatase activity, a further anti-angiogenic compound or a compound which induces cell differentiation processes; a bradykinin 1 receptor or an angiotensin II antagonist; a cyclooxygenase inhibitor, a bisphosphonate, a heparanase inhibitor (prevents heparan sulphate degradation), e.g., PI-88, a biological response modifier, preferably a lymphokine or interferons, e.g. interferon γ, an ubiquitination inhibitor or an inhibitor which blocks anti-apoptotic pathways; an inhibitor of Ras oncogenic isoforms or a farnesyl transferase inhibitor; a telomerase inhibitor, e.g., telomestatin; a protease inhibitor, a matrix metalloproteinase inhibitor, a methionine aminopeptidase inhibitor, e.g., bengamide or a derivative thereof; a proteasome inhibitor, e.g., PS-341 (bortezomib/Velcade); agents used in the treatment of hematologic malignancies or FMS-like tyrosine kinase inhibitors; an HSP90 inhibitors; histone deacetylase (HDAC) inhibitors; mTOR inhibitors; somatostatin receptor antagonists; integrin antagonists; antileukemic compounds; tumor cell damaging approaches, such as ionizing radiation; EDG binders; anthranilic acid amide class of kinase inhibitors; ribonucleotide reductase inhibitors; S-adenosylmethionine decarboxylase inhibitors; antibodies against VEGF or VEGFR; photodynamic therapy; angiostatic steroids; AT1 receptor antagonists; ACE inhibitors; and the like.

Other chemotherapeutic agents include, but are not limited to, plant alkaloids, hormonal agents and antagonists, biological response modifiers, preferably lymphokines or interferons, antisense oligonucleotides or oligonucleotide derivatives; or miscellaneous agents or agents with other or unknown mechanism of action.

The terms, "chemotherapeutic agents" and "chemotherapy agents" have been used interchangeably herein. In some embodiments, the chemotherapy agent is selected from the group consisting of paclitaxel; a platinum compound, carboplatin; bortezomib; vorinostat; rituximab; temozolomide; rapamycin; an alkylating agent; cyclophosphamide; an alkyl sulfonate; busulfan; improsulfan; piposulfan; an aziridine; an ethylenimine; a methylamelamine; an acetogenin; a camptothecin; a cryptophycin; a nitrogen mustard; a nitrosurea; an antibiotic; a enediyne antibiotic; a bisphosphonate; doxorubicin; a mitomycin; an anti-metabolite; a folic acid analogue; a purine analog; a pyrimidine analog; an androgen; an anti-adrenal; an epothilone; a maytansinoid; a trichothecene; gemcitabine; 6-thioguanine; mercaptopurine; methotrexate; vinblastine; etoposide; ifosfamide; mitoxantrone; vincristine; vinorelbine; novantrone; teniposide; edatrexate; daunomycin; aminopterin; xeloda; ibandronate; irinotecan; a topoisomerase inhibitor; a retinoid; capecitabine; combretastatin; leucovorin; lapatinib; and erlotinib.

In some embodiments, the immunotherapy agent is selected from the group consisting of anti-cancer agent, an anti-angiogenesis agent, a pro-angiogenesis agent, a vasodilator, a vasoconstrictor, an anti-neoplastic agent, an antiproliferative agent, an anti-mitotic agent, an anti-migratory agent, an anti-adhesive agent, an anti-platelet agent, antithrombotic agent, a thrombolytic agent, a thrombogenic agent, an anti-inflammatory agent, anti-atherosclerosis agent, anti-infective agent, anti-sepsis agent, or an anti-polymerization agent.

In some preferred embodiments, the chemotherapy agent or the immunotherapy agent is selected from the group consisting of daunorubicin, idarubicin, cytarabine, arsenic trioxide and tamibarotene.

The retinoic acid receptor agonists described herein are also useful in combination with known anti-cancer treatments. Generally, cancer treatment may involve one or more of the treatment options, but not limited to surgery, radiation, chemotherapy, immunotherapy, targeted therapy and hormonal therapy. The single agent therapy or current combination therapies for the treatment of cancer cause side effects such as nausea, rashes, swelling, flu-like symptoms, fatigue, digestive tract problems, allergic reactions and immunosuppression. In some embodiments, the invention described herein provides a more effective treatment of ACC by administering retinoic acid receptor agonists in combination with other cancer treatments. In some embodiments, the combination therapy induces additive or synergistic therapeutic effect. In some embodiments, the method described herein can reduce or prevent one or more adverse effects or toxicities associated with the administration of a chemotherapeutic agent or radiation therapy. In some embodiments, the method described herein can increase the antitumor activity of a chemotherapeutic agent or radiation therapy or increase the selective cytotoxicity of a chemotherapeutic agent.

The phrase "combination therapy" as described herein means administration of a retinoic acid receptor agonist and a therapeutic agent as part of a specific treatment regimen intended to provide a beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period. The time period may be in minutes, hours, days or weeks depending upon the combination selected.

Combination therapy includes administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be done, for example, by administering to the subject a single pill having a fixed ratio of each therapeutic agent or in multiple, single pills for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered may or may not be important.

Combination therapy also can mean the administration of the retinoic acid receptor agonists in further combination with other retinoic acid receptor agonists and non-drug therapies, such as, but not limited to, surgery or radiation treatment. Where the combination therapy further comprises radiation treatment, the radiation treatment may be conducted at any suitable time so long as a beneficial effect from the co-action of the combination of the therapeutic agents and radiation treatment is achieved.

In some embodiments, the methods described herein exclude the combination therapies known in the art involving retinoic acid receptor agonists. For example, WO 2000038730 describes using a combination of cyclooxygenase-2 inhibitor and retinoic acid for treating a neoplasmia disorder. Exemplary cyclooxygenase-2 inhibitors used in WO 2000038730 are 5-chloro-3-(4-(methylsulfonyl)phenyl)-2-(methyl-5-pyridinyl)pyridine, 2-(3,5-difluorophenyl)-3-4-(methylsulfonyl)phenyl)-2-cyclopenten-1-one, 4-[5-(4-methylphenyl)-3-(trifluoromethyl)-1H-pyrazol-1-yl]-benzenesulfonamide, 4-(4-(methylsulfonyl)phenyl]-3-phenyl-2(5H)-furanone, 4-(5-methyl-3-phenylisooxazol-4-yl)benzenesulfonamide and N-[[4-(5-methyl-3-phenylisooxazol-4yl]phenyl]sulfonyl]propanamide. In some embodiments, cyclooxygenase-2 inhibitors are excluded from the method of treatment of ACC.

US 2008/0119559 describes a method of treating cancer using a combination of sulindac, sulindac metabolites, sulindac derivatives or combinations thereof and/or R- and S-epimers thereof and an oxidizing agent comprising retinoic acid. In some embodiments, sulindac, sulindac metabolites, sulindac derivatives or combinations thereof and/or R- and S-epimers are excluded from the method of treatment of ACC.

Lingen et al. describe the use of retinoic acid and interferon alpha against head and neck squamous cell carcinoma (Lingen, M. et al. Cancer Research 1998, 58 (23), 5551-5558); Turlaro et al. describe the use of beta interferon and 13-cis retinoic acid to inhibit angiogenesis (Turlaro, M. et al. European Journal of Cancer 1998, 34 (4) 570-576); Majewski et al. describe a combination of Vitamin D3 and retinoids in the inhibition of tumor cell-induced angiogenesis (Majewski, S. et al. J. Invest. Dermatology Symposium Proceedings 1996, 1(1) 97-101) and Bollag describes retinoids and alpha-interferon in the treatment of neoplastic disease (Bollag, W. Chemotherapie Journal (Suppl) 1996, 5(10) 55-64.

The combinations of retinoic acid and interferon alpha; beta interferon and 13-cis retinoic acid and Vitamin D3 and retinoids are excluded from some embodiments of the method of treatment of ACC.

In some embodiments of this and other aspects of the invention, retinoic acid receptor agonists are administered to the subject by itself without any combination therapy. In some embodiments, the retinoic acid receptor agonists are administered to the subject with combination therapy, wherein the combination therapy consists of non-drug therapies only, such as, but not limited to, surgery or radiation treatment. In some embodiments, the retinoic acid receptor agonists are administered to the subject without any additional therapeutic agent. In some embodiments, the retinoic acid receptor agonists are administered to the subject without any other anticancer therapy. In some embodiments, the retinoic acid receptor agonists are administered to the subject without any other chemotherapy agent. In some embodiments, the retinoic acid receptor agonists are administered to the subject without any other immunotherapy agent.

In one aspect, the invention provides a method for inhibiting expression of oncogenic transcription factor MYB in a cell, comprising: contacting a cell expressing MYB with a retinoic acid receptor agonist. One skilled in the art will be able to determine if a cell expresses MYB using standard techniques. For example, expression levels of a protein in a cell can be quantified by Western blotting, by an immunological detection of the protein, ELISA (enzyme-linked immunosorbent assay), radioimmunoassay (RIA), or immunoassays. C-MYB-specific antibodies are commercially available from Santa Cruz Biotechnology (Dallas, Tex.) and are used to detect expression of MYB protein in a cell. Fluorescence-activated cell sorting and analysis (FACS) of fluorescently-labeled protein (for example, c-MYB:GFP) is additionally used to detect protein expression in a cell. Expression levels of RNA in a cell can be quantified, for example by in situ hybridization. Gene translation can be measured by quantitation of protein expressed from a gene using methods described above.

Inhibition of MYB expression due to contact of a cell with a retinoic acid receptor agonist can be determined using any assay for protein, RNA, or gene expression described above. Generally, MYB expression in a cell contacted by a retinoic acid receptor agonist will be compared to a reference level, for example MYB expression in an identical cell not contacted by a retinoic acid receptor agonist. In some embodiments, MYB expression is inhibited at least 10% as compared to the reference level. In some embodiments, MYB expression is inhibited at least 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99% as compared to the reference level. 100% inhibition of MYB expression compared to the reference level is defined as complete inhibition of MYB.

In another aspect provided herein is a method for screening chemical compounds or compositions in embryonic cells, e.g., zebrafish embroyos. The embodiments of the disclosure provide a system for screening modulators of MYB activity or expression. More specifically, the present disclosure provides for screening, including high throughput screening, for modulators that effect MYB activity and/or expression. Generally, the assay comprises contacting an embryonic cell with a test compound, wherein the cell comprises a reporter gene; and determining the amount of reporter gene expression after incubation with the test compound; wherein a change in the expression of the reporter gene relative to a control or reference indicates that the compound modulates the expression or activity of MYB or MYBL1. In some embodiments, the screening assay utilizes zebrafish embryos.

In one embodiment, the compound inhibits the expression or activity of MYB or MYBL1 relative to a control or reference. Using the present invention, one can distinguish compounds that increase, decrease or otherwise modulate MYB activity or expression. Specificity is high in this well-defined assay, providing deeper and broader information including obtaining compounds that can induce a change in MYB activity and/or expression.

Generally, the method comprises the steps of culturing embryos in presence of a test compound, wherein at least one cell in the cell culture comprises a reporter gene, wherein the reporter gene encodes a cell lineage specific marker and produces a detectable signal when expressed; and measuring/detecting the detectable signal. A change in level or amount of the detectable signal indicating that the test compound modulates MYB activity and/or expression. The level or amount of the detectable signal can be determined relative to a reference or control. In some embodiments, the reference or control can be a blastomere culture without the test compound.

As used herein, the term "reporter gene" refers to a gene that expresses a cell marker that is expressed in a cell lineage specific manner and produces a detectable response or signal. As used herein, the term "detectable" refers to a molecule or an element or functional group in a molecule that allows for the detection, imaging, and/or monitoring of the presence the molecule. The reporter gene can be an endogenous gene, an exogenous gene, or a transgene. A detectable response generally refers to a change in, or occurrence of, a signal that is detectable either by observation or instrumentally. Without limitations, the expressed molecule can be detected directly or the molecule can produce a detectable signal in the presence of a reagent. Further, any available method for determining the amount of the reporter in a culture can be employed. In some embodiments, detectable response is an optical signal, i.e., the reporter is an optical reporter. Suitable optical reporters include, but are not limited to, fluorescent reporters and chemiluminescent groups.

In some embodiments, the detectable response is fluorescence or a change in fluorescence, e.g., a change in fluorescence intensity, fluorescence excitation or emission wavelength distribution, fluorescence lifetime, and/or fluorescence polarization. In some embodiments, the reporter gene encodes a fusion protein comprising MYB fused with a fluorescent protein (i.e., a MYB::FP construct or fusion protein). In one embodiment, the reporter gene is c-myb: GFP.

Examples of fluorescent proteins suitable for use include, but are not limited to, green fluorescent protein, red fluorescent protein (e.g., DsRed), yellow fluorescent protein, cyan fluorescent protein, blue fluorescent protein, and variants thereof (see, e.g., U.S. Pat. Nos. 6,403,374, 6,800,733, and 7,157,566). Specific examples of GFP variants include, but are not limited to, enhanced GFP (EGFP), destabilized EGFP, the GFP variants described in Doan et al, Mol. Microbiol, 55:1767-1781 (2005), the GFP variant described in Crameri et al, Nat. Biotechnol., 14:315319 (1996), the cerulean fluorescent proteins described in Rizzo et al, Nat. Biotechnol, 22:445 (2004) and Tsien, Annu. Rev. Biochem., 67:509 (1998), and the yellow fluorescent protein described in Nagal et al, Nat. Biotechnol., 20:87-90 (2002). DsRed variants are described in, e.g., Shaner et al, Nat. Biotechnol., 22:1567-1572 (2004), and include mStrawberry, mCherry, morange, mBanana, mHoneydew, and mTangerine. Additional DsRed variants are described in, e.g., Wang et al, Proc. Natl. Acad. Sci. U.S.A., 101:16745-16749 (2004) and include mRaspberry and mPlum. Further examples of DsRed variants include mRFPmars described in Fischer et al, FEBS Lett., 577:227-232 (2004) and mRFPruby described in Fischer et al, FEBS Lett, 580:2495-2502 (2006).

Other non-limiting list of fluorescent proteins incudes AceGFP, AcGFP1, AmCyan1, AQ143, AsRed2, Azami-Green (mAG), Cerulean, Cerulean, Citrine, cOFP, CopGFP, Cyan, CyPet, Dronpa, DsRed/DsRed2/DsRed-Express, DsRed-Monomer, EBFP, ECFP, EGFP, Emerald, eqFP611, EYFP, GFPs, HcRed1, HcRed-tandem, J-Red, Kaede, KFP, KikGR, mBanana, mCFP, mCherry, mCitrine, mEosEP, mHoneydew, MiCy, mKO, mOrange, mPlum, mRaspberry, mRFP1, mStrawberry, mTangerine, mYFP, mYFP, mYFP, PA-GFP, PA-mRFP, PhiYFP, PS-CFP-2, Renilla, tdEosFP, tdTomato, T-Sapphire, TurboGFP, UV-T-Sapphire, Venus, YPet, ZsYellow1, and derivatives and analogs thereof. In one embodiment, the fluorescent protein is Green Fluorescent Protein (GFP).

One of skill in the art is well aware of methods for constructing reporter genes that encode fusion proteins comprising fluorescent proteins.

Specific devices or methods known in the art for the detection of fluorescence, e.g., from fluorophores or fluorescent proteins, include, but are not limited to, in vivo near-infrared fluorescence (see, e.g., Frangioni, Curr. Opin. Chem. Biol, 7:626-634 (2003)), the Maestro™ in vivo fluorescence imaging system (Cambridge Research & Instrumentation, Inc.; Woburn, Mass.), in vivo fluorescence imaging using a flying-spot scanner (see, e.g., Ramanujam et al, IEEE Transactions on Biomedical Engineering, 48:1034-1041 (2001), and the like. Other methods or devices for detecting an optical response include, without limitation, visual inspection, CCD cameras, video cameras, photographic film, laser-scanning devices, fluorometers, photodiodes, quantum counters, epifluorescence microscopes, scanning microscopes, flow cytometers, fluorescence microplate readers, or signal amplification using photomultiplier tubes.

In some embodiments, the FP can be Green fluorescent protein (GFP) or mCherry. In some embodiments, the reporter gene encodes a fusion protein comprising Myf5 and GFP.

The term "embryonic cell" is used throughout to refer to at least one embryonic cell (e.g., 1, 2, 3, 4, etc. . . . ) obtained from an embryo.

For the screening assay disclosed herein, the embryonic cell can be obtained from any source available to the practitioner or one of skill in the art. In some embodiments, the embryonic cell is from zebrafish. As used herein, the term "zebrafish" refers to any fish or strain of fish that is considered to be of the genus and species Danio rerio. In some embodiments, the embryonic cell can be from a transgenic species that expresses MYB fused with a fluorescent protein. One of skill in the ordinary skill in the art is well aware of methods for producing transgenic zebrafish and can easily use these methods for producing transgenic zebrafish from which the embryonic cell for the screening assay can be obtained. See, for example, Gabriela, et al., BMC Developmental Biology 2007, 7:62 (doi:10.1186/1471-213X-7-62), content of which is incorporated herein by reference in its entirety.

Culture media for culturing the embryonic cell can be any suitable media available to one of skill in the art for culturing embryos. For example, one can use zESC medium, which is composed of 70% LDF medium and 30% RTS34st-conditioned medium.

For the assay, the embryonic cell can be optionally allowed to grow for a period time before contacting with the test compound. In some embodiments, a practitioner can obtain embryonic cell that are already planted in the appropriate vessel and allowed to grow for a period of time. In other embodiments, the practitioner plates the embryonic cell in the appropriate vessel and allow them to grow for a period time, e.g., at least one day, at least two days, at least three days, at least four days, at least five days, at least six days, at least seven days or more before contacting with the test compound.

After the test compound has been in contact with the cell for a sufficient period of time, amount of reporter (e.g., expression or activity of MYB) is measured and compared to a control or reference. For example, contact time can be from seconds to days or weeks. The practitioner can optimized the contact time for obtaining an optimal signal-to-noise ratio, time constraints, amount of test compound to be tested, number of cells, test volume, availability of reagents for the assay, and the like.

As used herein, the term "test compound" refers to compounds and/or compositions that are to be screened for their ability to inihbit and/or decrease and/or antagonize MYB activity or expression. The test compounds can include a wide variety of different compounds, including chemical compounds and mixtures of chemical compounds, e.g., small organic or inorganic molecules; saccharines; oligosaccharides; polysaccharides; biological macromolecules, e.g., peptides, proteins, and peptide analogs and derivatives; peptidomimetics; nucleic acids; nucleic acid analogs and derivatives; an extract made from biological materials such as bacteria, plants, fungi, or animal cells; animal tissues; naturally occurring or synthetic compositions; and any combinations thereof. In some embodiments, the test compound is a small molecule.

The number of possible test compounds runs into millions. Methods for developing small molecule, polymeric and genome based libraries are described, for example, in Ding, et al. J Am. Chem. Soc. 124: 1594-1596 (2002) and Lynn, et al., J. Am. Chem. Soc. 123: 8155-8156 (2001). Commercially available compound libraries can be obtained from, e.g., ArQule, Pharmacopia, graffinity, Panvera, Vitas-M Lab, Biomol International and Oxford. These libraries can be screened using the screening devices and methods described herein. Chemical compound libraries such as those from NIH Roadmap, Molecular Libraries Screening Centers Network (MLSCN) can also be used. A comprehensive list of compound libraries can be found at www.broad.harvard. edu/chembio/platform/screening/compound_libraries/index.htm. A chemical library or compound library is a collection of stored chemicals usually used ultimately in high-throughput screening or industrial manufacture. The chemical library can consist in simple terms of a series of stored chemicals. Each chemical has associated information stored in some kind of database with information such as the chemical structure, purity, quantity, and physiochemical characteristics of the compound.

As used herein, the term "small molecule" can refer to compounds that are "natural product-like," however, the term "small molecule" is not limited to "natural product-like" compounds. Rather, a small molecule is typically characterized in that it contains several carbon-carbon bonds, and has a molecular weight more than about 50, but less than about 5000 Daltons (5 kD). Preferably the small molecule has a molecular weight of less than 3 kD, still more preferably less than 2 kD, and most preferably less than 1 kD. In some cases it is preferred that a small molecule have a molecular mass equal to or less than 700 Daltons.

Depending upon the particular embodiment being practiced, the test compounds can be provided free in solution, or may be attached to a carrier, or a solid support, e.g., beads. A number of suitable solid supports may be employed for immobilization of the test compounds. Examples of suitable solid supports include agarose, cellulose, dextran (commercially available as, i.e., Sephadex, Sepharose) carboxymethyl cellulose, polystyrene, polyethylene glycol (PEG), filter paper, nitrocellulose, ion exchange resins, plastic films, polyaminemethylvinylether maleic acid copolymer, glass beads, amino acid copolymer, ethylene-maleic acid copolymer, nylon, silk, etc. Additionally, for the methods described herein, test compounds can be screened individually, or in groups. Group screening is particularly useful where hit rates for effective test compounds are expected to be low such that one would not expect more than one positive result for a given group. Group screening is also useful for determining hits that can act synergistically.

The test compound can be tested at any desired concentration. For example, the test compound can be tested at a final concentration of from 0.01 nm to about 10 mM. Further, the test can be tested at 2 or more (e.g., 2, 3, 4, 5, 6, 7, 8, 9, 10 or more) different concentrations. This can be helpful if the test compound is active only in a range of concentration. When the test compound is tested at 2 or more different concentrations, the concentration difference can range from 10-10,000 fold (e.g., 10-5000 fold, 10-1000 fold, 10-500 fold, or 10-250 fold).

The screening assay can be performed in any suitable container or apparatus available to one of skill in the art for cell culturing. For example, the assay can be performed in 24-, 96-, or 384-well plates. In one embodiment, the assay is performed in a 384-well plate.

In some embodiments, the screening method is a high-throughput screening. High-throughput screening (HTS) is a method for scientific experimentation that uses robotics, data processing and control software, liquid handling devices, and sensitive detectors. High-Throughput Screening or HTS allows a researcher to quickly conduct millions of biochemical, genetic or pharmacological tests. High-Throughput Screening are well known to one skilled in the art, for example, those described in U.S. Pat. Nos. 5,976, 813; 6,472,144; 6,692,856; 6,824,982; and 7,091,048, and contents of each of which is herein incorporated by reference in its entirety.

HTS uses automation to run a screen of an assay against a library of candidate compounds. An assay is a test for specific activity: usually inhibition or stimulation of a biochemical or biological mechanism. Typical HTS screening libraries or "decks" can contain from 100,000 to more than 2,000,000 compounds.

The key labware or testing vessel of HTS is the microtiter plate: a small container, usually disposable and made of plastic, which features a grid of small, open divots called wells. Modern microplates for HTS generally have either 384, 1536, or 3456 wells. These are all multiples of 96, reflecting the original 96 well microplate with 8×12 9 mm spaced wells.

To prepare for an assay, the researcher fills each well of the plate with the appropriate reagents that he or she wishes to conduct the experiment with, such as an embryonic cell or population thereof. After some incubation time has passed to allow the reagent to absorb, bind to, or otherwise react (or fail to react) with the compounds in the wells, measurements are taken across all the plate's wells, either manually or by a machine. Manual measurements are often necessary when the researcher is using microscopy to (for example) seek changes that a computer could not easily determine by itself. Otherwise, a specialized automated analysis machine can run a number of experiments on the wells such as colorimetric measurements, radioactivity counting, etc. In this case, the machine outputs the result of each experiment as a grid of numeric values, with each number mapping to the value obtained from a single well. A high-capacity analysis machine can measure dozens of plates in the space of a few minutes like this, generating thousands of experimental data points very quickly.

Screening using zebrafish embryos is useful for the study of development, disease, and stem cell biology. However, the required manual manipulation of zebrafish embryos prevents capitalizing on recent innovations in high-speed pipetting and imaging. Compared to screening using zebrafish embryos, the screening assay described herein is highly automatic, taking one sixth of the time, and consumes only one tenth of the embryo. Such throughput enables screening of larger chemical libraries and can be used for screening of a genetic mutant suppressor. For example, several zebrafish anemia mutants, including cia, edy, and weh, have defects in iron metabolism and lack benzidine staining, a marker for mature erythrocytes. The screening assay of the present disclosure can be designed to screen for chemicals that restore benzidine staining. Without wishing to be bound by a theory, the chemicals identified can be used to treat these iron metabolism defects.

Transgenic zebrafish with a fluorescent reporter that labels a cell, tissue, or protein of interest are widely used in the study of development and stem cell biology. Despite the pioneering of transgenic reporter lines for screening, readout by WISH is usually preferred. Compared to WISH, transgenic reporters are usually thought to be less sensitive to detect a difference. Moreover, transgenic embryos need to be fixed and scored immediately. However, the inventors surprising and unexpectedly found that transgenic reporters were useful for the screening assay described herein, mainly because transgenic reporters in a 2-dimensional culture are more sensitive than those in a 3-D embryo. Moreover, because images are automatically captured and stored by imaging cytometers, the cells do not need to be fixed or scored immediately. Further, the screening assay described herein enables combining reporters of different colors, allowing the determination of different developmental states or lineages simultaneously.

Since embryonic cells in culture lack spatial and temporal information, the screening assay described herein uses cellular markers, like transgenic fluorescent reporters. Cell membrane markers, like F-actin and Membrane-GFP, and nuclear markers, like DAPI and H2B-Tomato, can also be used to acquire additional information regarding cellular morphology and cell number. The possibility that a transgenic reporter may behave differently in vitro requires researchers to confirm that the reporter line in culture recapitulates its in vivo expression pattern.

The development of a robust chemical screening system using embryonic cells is an important complement to studies using embryos. Without wishing to be bound by a theory, other genetic tools like morpholino/siRNA knockdown and mRNA overexpression can be used to enable genome-wide loss-of-function and gain-of-function genetic screening using blastomere cells. A casper based transplantation system can be exploited for the study of engraftment and self-renewal of cells derived from the system. In summary, the data presented herein indicates that the system described herein enables screening using well-established fluorescent transgenic lines and capitalizes on advances in high-speed pipetting and imaging systems. This system can be modified for any cell lineage and can enhance our understanding of developmental biology and to provide insights into cell-based therapies for many diseases.

The present disclosure also provides a compound selected by the screening assay disclosed in this disclosure.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein the term "comprising" or "comprises" is used in reference to compositions, methods, and respective component(s) thereof, that are essential to the method or composition, yet open to the inclusion of unspecified elements, whether essential or not.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9); Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the present invention was performed using standard procedures, as described, for example in Sambrook et al., Molecular Cloning: A Laboratory Manual (3 ed.), Cold Spring Harbor Laboratory Press, Cold Spring Harbor, N.Y., USA (2001); Davis et al., Basic Methods in Molecular Biology, Elsevier Science Publishing, Inc., New York, USA (1995); Current Protocols in Cell Biology (CPCB) (Juan S. Bonifacino et. al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998) which are all incorporated by reference herein in their entireties.

Some embodiments of the technology described herein can be defined according to any of the following numbered paragraphs:

1. A method for treatment of adenoid cystic carcinoma (ACC) comprising: selecting a subject in need of treatment for ACC and administering a therapeutically effective amount of a retinoic acid receptor agonist to the subject.
2. The method of paragraph 1, wherein the subject does not require or is not undergoing treatment for acute promyelocytic leukemia (APL).
3. The method of paragraph 1 or 2, wherein the subject has a gene translocation in oncogenic transcription factor MYB.
4. The method of paragraph 2 or 3, wherein said gene translocation is MYB-NFIB fusion (MYB-NFIB translocation).
5. The method of any one of paragraphs 1-4, wherein the retinoic acid receptor agonist is selected from the group consisting of all-trans retinoic acid (ATRA), 13-cis-retinoic acid (isotretinoin), 4-[(1,1,4,4-tetramethyltetralin-6-yl)carbamoyl]benzoic acid (tamibarotene), 4-[(5,6,7,8-Tetrahydro-5,5,8,8-tetramethyl-2-naphthalenyl) carboxamido]benzoic acid (AM-580), 9-cis retinoic acid, retinoic acid p-hydroxyanilide (Fenretinide), 4-[(E)-2-(5,6,7,8-Tetrahydro -5,5,8,8-tetramethyl-2-naphthalenyl)-1-propenyl]benzoic acid (TTNPB), and 4-[4-(2-Butoxyethoxy-)-5-methyl-2-thiazolyl]-2-fluorobenzoic acid (AC 261066).
6. The method of any one of paragraphs 1-5, wherein the retinoic acid receptor agonist is all-trans retinoic acid.
7. The method of any one of paragraphs 1-6, wherein the agonist is administered in amount from about 1 µg/kg to about 150 mg/kg per day.
8. The method of any one of paragraphs 1-7, wherein the agonist is administered in amount from about 10 mg/kg to about 40 mg/kg per day.
9. The method of any one of paragraphs 1-8, wherein said administration is in a single dosage.
10. The method of any one of paragraphs 1-8, wherein said administration is in two or more dosages.
11. The method of any one of paragraphs 1-10, wherein the agonist is administered orally.
12. The method of any one of paragraphs 1-11, further comprising administering an anticancer therapy.
13. The method of paragraph 12, wherein cyclooxygenase-2-inhibitors and sulindac or sulindac derivatives are excluded.
14. The method of any one of paragraphs 1-12, further comprising administering a chemotherapy agent or an immunotherapy agent.
15. The method of paragraph 14, wherein the chemotherapy/immunotherapy agent is not a cyclooxygenase-2-inhibitor.
16. The method of paragraph 14, wherein the chemotherapy/immunotherapy agent is not a sulindac, sulindac metabolite, sulindac derivative or combination thereof and/or R- and S-epimer.
17. A method for inhibiting expression of oncogenic transcription factor MYB in a cell, comprising: contacting a cell expressing MYB with a retinoic acid receptor agonist.
18. An assay for identifying a compound that modulates the expression or activity of MYB or MYBL1, the method comprising:
   (i) contacting an embryonic cell with a test compound, wherein the cell comprises a reporter gene; and
   (ii) determining the amount of reporter gene expression after incubation with the test compound;
   wherein a change in the expression of the reporter gene relative to a control or reference indicates that the compound modulates the expression or activity of MYB or MYBL 1.
19. The assay of paragraph 18, wherein the test compound inhibits the expression or activity of MYB or MYBL1 relative to a control or reference.
20. The assay of paragraph 18 or 19, wherein the reporter gene is c-myb:GFP gene.
21. The assay of any one of paragraphs 18-20, wherein the assay is a high throughput screening (HTS) assay.

To the extent not already indicated, it will be understood by those of ordinary skill in the art that any one of the various embodiments herein described and illustrated may be further modified to incorporate features shown in any of the other embodiments disclosed herein.

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

EXAMPLES

Example 1: Retinoic Acid Suppression of c-Myb in ACC

The inventors have developed an embryo culture system in which embryos bearing a c-myb:GFP transgenic reporter were dissociated during sphere stage at 4 hours post fertilization (hpf), and cultured in gelatin-coated 384 well plates with chemicals for 2 days until imaging for fluorescent reporter activity (FIG. 1). This fluorescent transgene is expressed in a similar pattern to the endogenous gene. The brief culture time reflects the accelerated embryonic development of zebrafish relative to mammals, which renders this system more efficient and robust for screening. This transgene responds to inducers of hematopoiesis, as myb is a marker of hematopoietic stem cells (HSCs).

A chemical screen of 3,840 compounds was completed for suppressors of myb from four library sets at an initial screening concentration of approximately 30 µM: Evotec's NIH (720), Sigma's Library of Pharmacologically Active Compounds (LOPAC, 1,440), BIOMOL ICCB Known Bioactives (480), and ChemBridge's Nuclear Hormone Receptor (NHR) and Kinacore library (1,200). These libraries were selected to significantly expand and diversify the repertoire of previously tested compounds. The NIH and LOPAC libraries include pharmacologically active compounds. The NHR and Kinacore libraries include compounds with structural similarities to published compounds active against nuclear hormone receptors. Chemical hits from the screen that suppress the transgene likely act by inhibiting myb transcription, making them potential therapies for adenoid cystic carcinoma tumors.

The image analysis software (ImageJ and MatLab) was used to identify hits that downregulate c-myb:GFP zebrafish embryo cultures by a z-score less than 1.44 and more than 70% downregulation. Hits were assessed by eye and scored for morphology. Toxic compounds that caused poor embryoid body (EB) formation were assessed a 4. The hits were selected from category 1 that showed downregulation of c-myb:GFP and good EB morphology to minimize toxicity effects.

Among the hits, several retinoic acid (RA) agonist derivatives such as all-trans retinoic acid (ATRA) were found to lead to suppression of the transgene with minimal toxicity (assessed by cellular morphology), suggesting the importance of nuclear hormone signaling in regulating myb expression (Tables 2 and 3).

TABLE 3

Retinoic acid agonists decrease GFP signal in the blastomere embryo culture screen.

| Chemical | Fold Change | Z-Score |
| --- | --- | --- |
| All-trans retinoic acid | −0.95857 | −5.72903 |
| Isotretinoin | −0.95571 | −5.05412 |
| AM-580 | −0.95472 | −1.63138 |
| 9-cis retinoic acid | −0.91531 | −1.56594 |
| Retinoic acid p-hydroxyanilide | −0.91488 | −1.58231 |
| TTNPB | −0.91253 | −1.63390 |
| AC 261066 | −0.77341 | −1.69716 |

Figure 6:
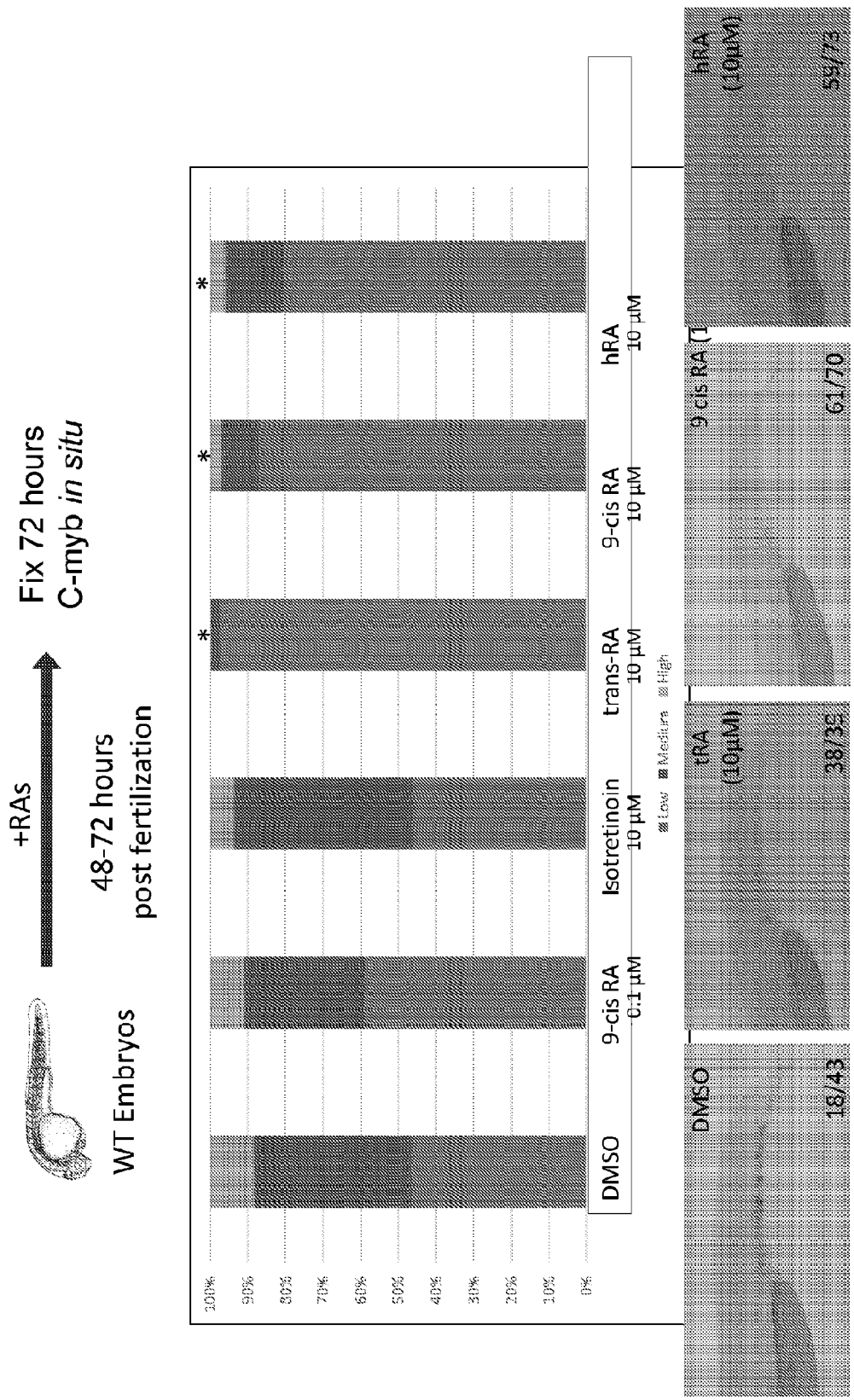
FIG. 6 is a graph showing in situ hybridization for c-myb which showed a significant decrease due to RA treatment during 48-72 hpf. *P<0.05.

Dose response follow-up experiments confirmed that the RA agonists are potent downregulators of c-myb:GFP cultures (FIGS. 4A-4F) and by c-myb in situ hybridization of whole embryos treated at 48-72 hpf (FIG. 6).

Figure 5:
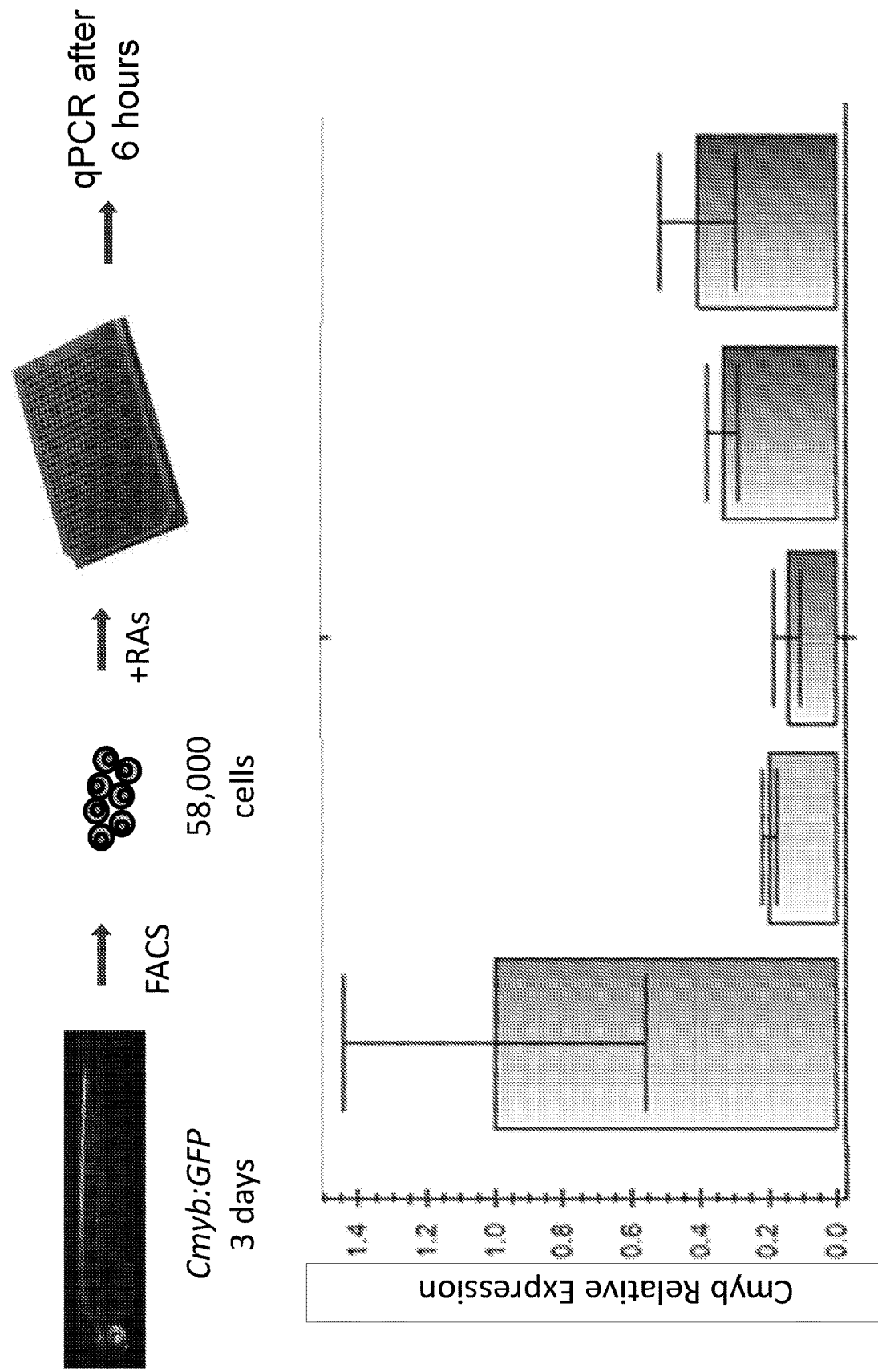
FIG. 5 is a bar graph showing c-myb relative expression for some representative retinoic acid agonists. C-myb gene expression of 58,000 sorted c-myb:GFP cells from 72 hpf c-myb:GFP embryos was suppressed when treated at 1 μM for 6 hours with various RAs by qPCR.

To validate the effects of RA on myb expression, it was confirmed by qPCR that ATRA, 9-cis-RA, RA p-hydroxyanilide, and isotretinoin significantly downregulate endogenous myb levels of sorted c-myb:GFP zebrafish embryo cells in culture after six hours incubation on a per-cell basis (FIG. 5). Following a standard 45 mg/m2 oral dose of ATRA in patients, the median plasma concentration is approximately 1 µM on the first day of treatment. The other clinically available RA compounds achieve a similar plasma concentration. Thus, the RA derivatives were tested at a dose of 1 µM to reflect the relevant bioavailability in patients. A time course experiment further showed that ATRA, 9-cis-RA, RA p-hydroxyanilide, and isotretinoin significantly downregulate myb levels in the human leukemia cell line U937, which normally expresses high levels of myb, at 6,

TABLE 2

Several retinoic acid agonist derivatives downregulate myb expression.

| Chemical | Function | Fold Change | Z-Score |
| --- | --- | --- | --- |
| '1-(4-Fluorobenzyl)-5-methoxy-2-methylindole-3-acetic acid' | MRP1 inhibitor | −0.97727 | −1.72623 |
| 'N-[1-(1,5-dimethyl-1H-pyrazol-4-yl)ethyl]thieno[2,3-d]pyrimidin-4-amine' | KINAcore | −0.97313 | −2.82986 |
| 'TREMULACIN' | Natural product, antiinflammatory | −0.96773 | −3.9299 |
| 'Retinoic acid' | Retinoic acid agonist | −0.95857 | −5.72903 |
| '4-(4-methoxyphenyl)-3,3-dimethyl-N-(3-methyl-1,2,4-thiadiazol-5-yl)piperazine-1-carboxamide' | NHRcore | −0.95663 | −2.35685 |
| 'Isotretinoin' | Retinoic acid agonist | −0.95571 | −5.05412 |
| 'AM-580' | Retinoic acid agonist | −0.95472 | −1.63138 |
| '3-(4-fluorobenzyl)-N-(3-methyl-1,2,4-thiadiazol-5-yl)piperidine-1-carboxamide' | NHRcore | −0.93509 | −3.28653 |
| '9-cis Retinoic acid' | Retinoic acid agonist | −0.91531 | −1.56594 |
| 'Retinoic acid p-hydroxyanilide' | Retinoic acid agonist | −0.91488 | −1.58231 |
| 'TTNPB' | Retinoic acid agonist | −0.91253 | −1.6339 |
| '4-[(2-methylphenyl)thio]-N-(3-methyl-1,2,4-thiadiazol-5-yl)piperidine-1-carboxamide' | NHRcore | −0.87449 | −2.22776 |
| '1,3-dimethyl-5-({[4-(1,3,5-trimethyl-1H-pyrazol-4-yl)pyrimidin-2-yl]amino}methyl)-1,3-dihydro-2H-benzimidazol' | KINAcore | −0.86694 | −2.02581 |
| 'FluniSOLIDe' | GR agonist | −0.85742 | −3.08536 |
| 'N-[(5-chloro-1H-indol-2-yl)methyl]-2-(3-hydroxyphenyl)acetamide' | KINAcore | −0.85676 | −3.29747 |
| 'Riluzole' | Na Channel | −0.84519 | −6.52096 |
| AC 261066 | Retinoic acid agonist | −0.77341 | −1.69716 |
| L-733,060 hydrochloride | tachykinin NK1 antagonist | −0.752 | −1.71471 |
| (−)-Perillic acid | pro-apototic | −0.73266 | −1.84844 |
| 'Evista' | Estrogen receptor modulator | −0.71314 | −3.31848 |
| 'Diacylglycerol Kinase Inhibitor II' | ip3 signaling | −0.70682 | −1.49298 |
| '4-(1,3-dimethyl-1H-pyrazol-4-yl)-N-(3,3-dimethyl-1-pyridin-3-ylbutyl)pyrimidin-2-amine' | NHRcore | −0.70233 | −2.28996 |

Figure 7:
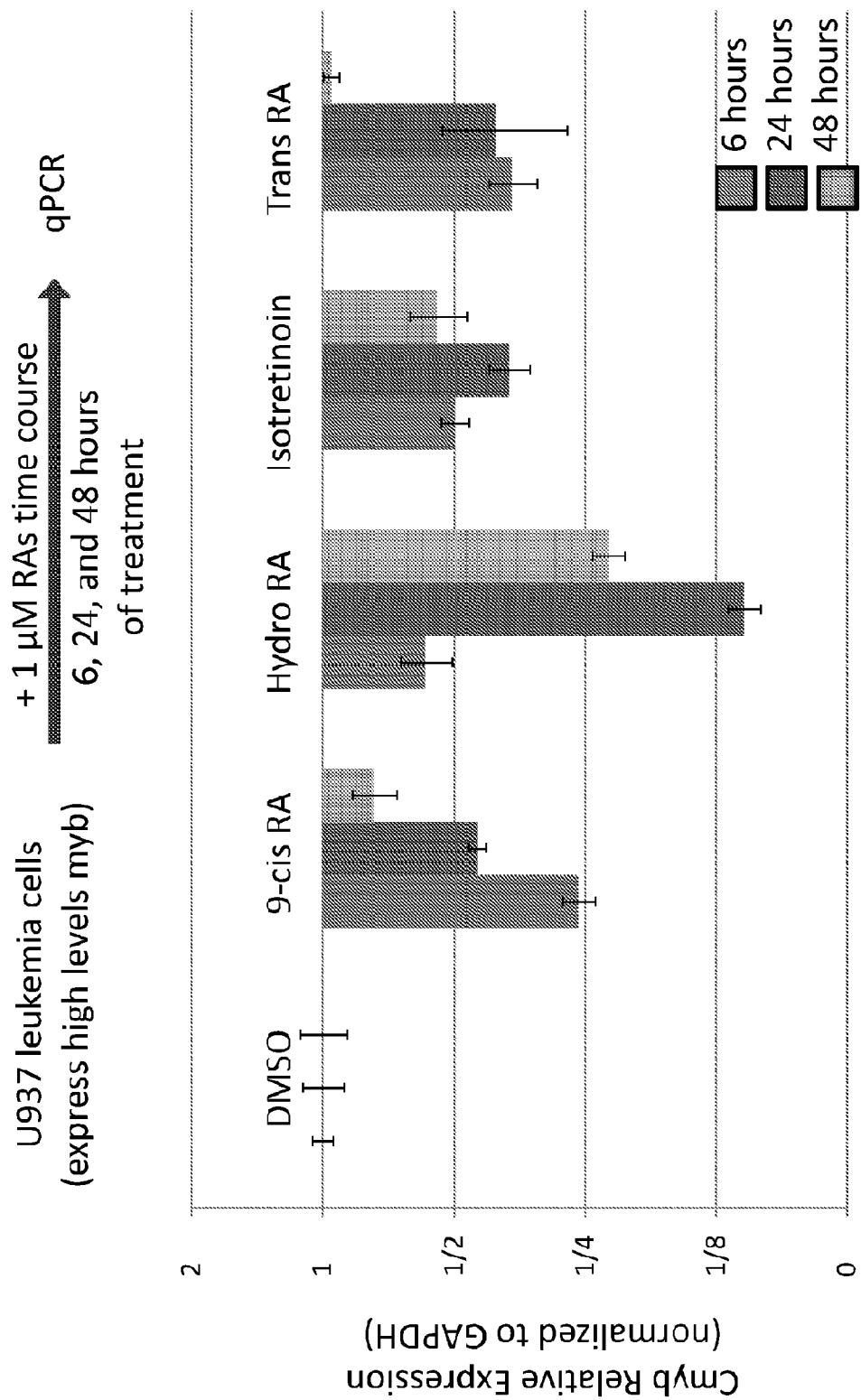
FIG. 7 is a bar graph showing c-myb gene expression of U937 cells treated at 1 μM over time by qPCR.
Figure 8:
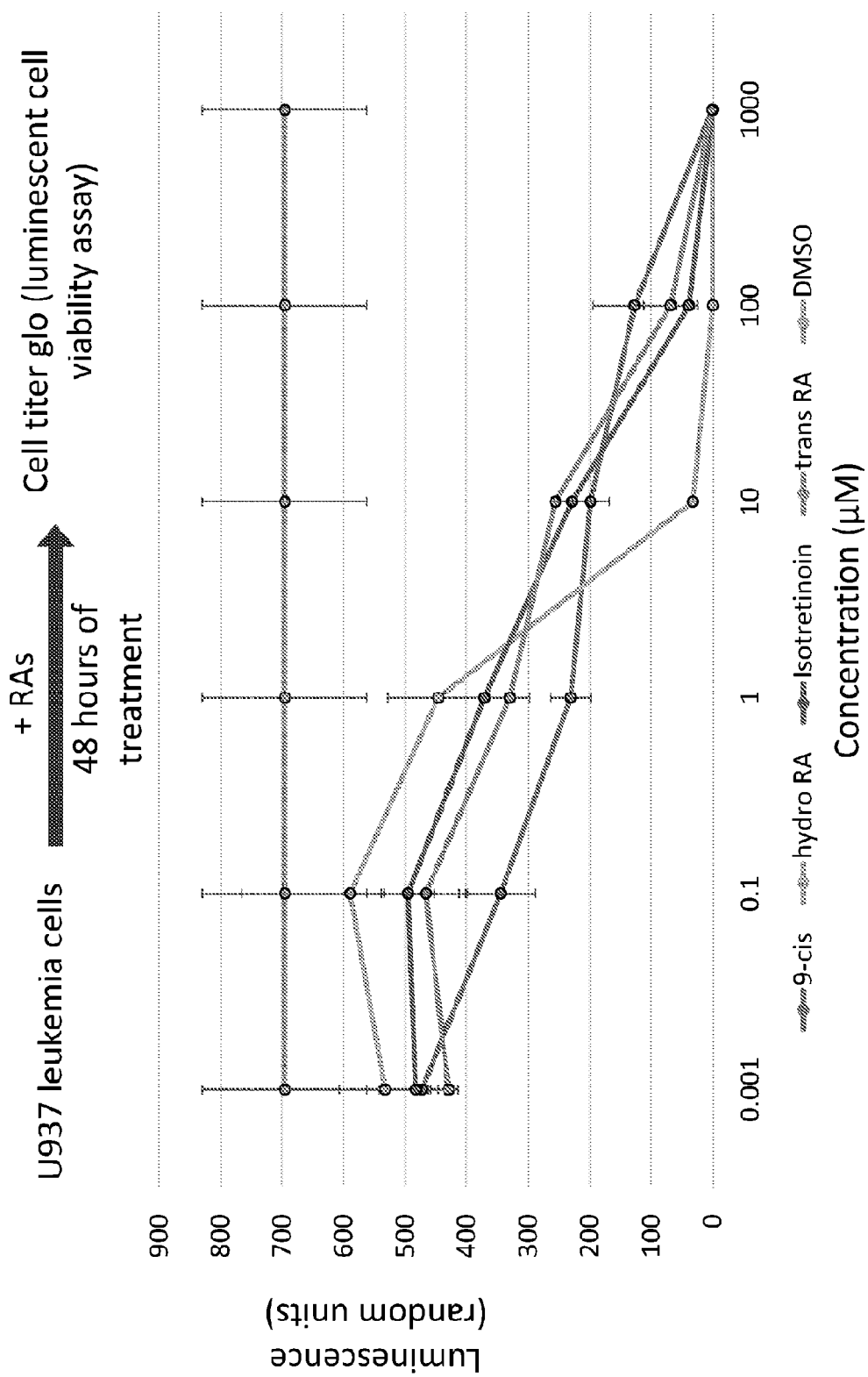
FIG. 8 is a graph showing luminescence vs. concentration of retinoic acid agonists. U937 proliferation after 2 days of various RA treatments assessed by CellTiter-Glo showed a dose-dependent effect.
Figure 9A:
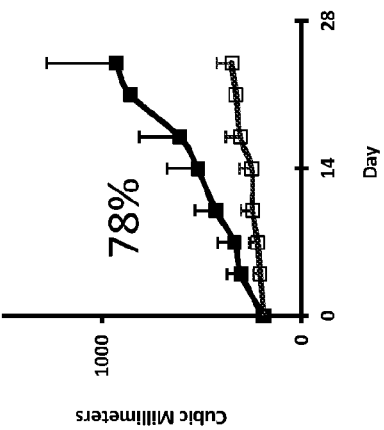
Figure 9B:
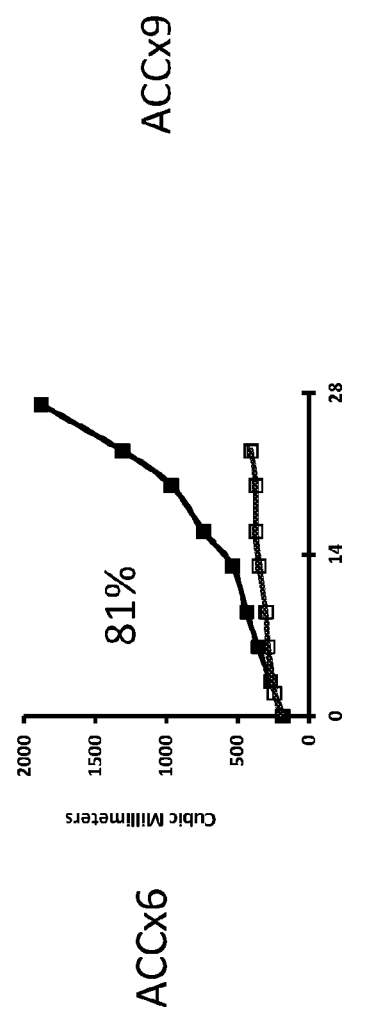
Figure 9C:
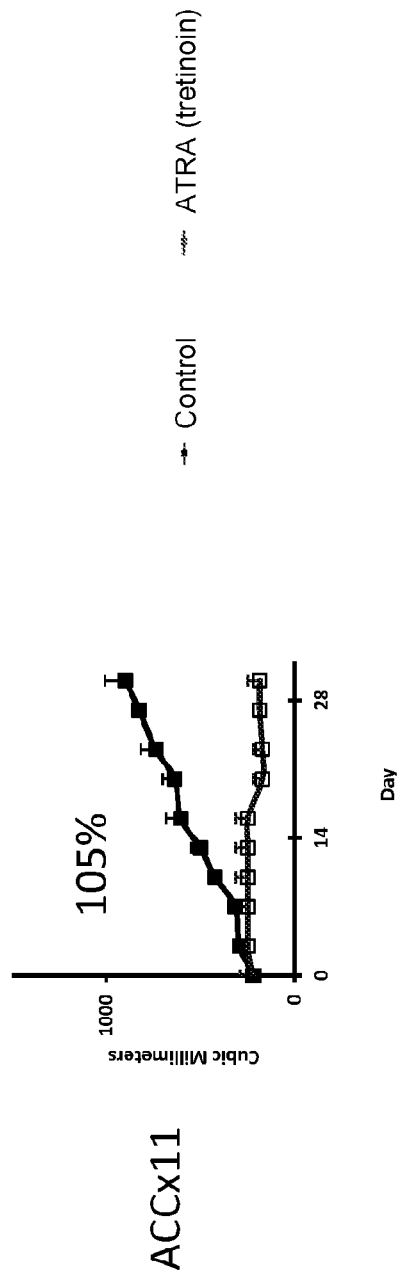
Figure 9H:
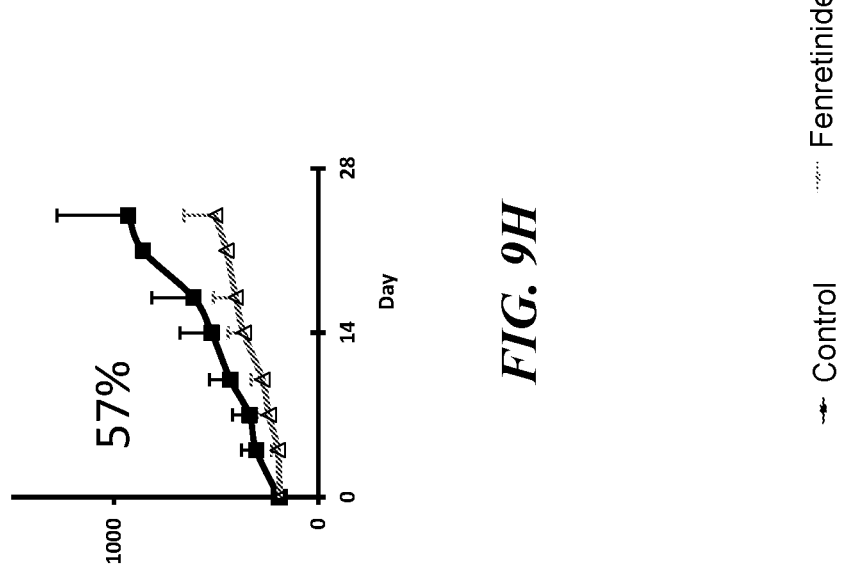
Figure 9I:
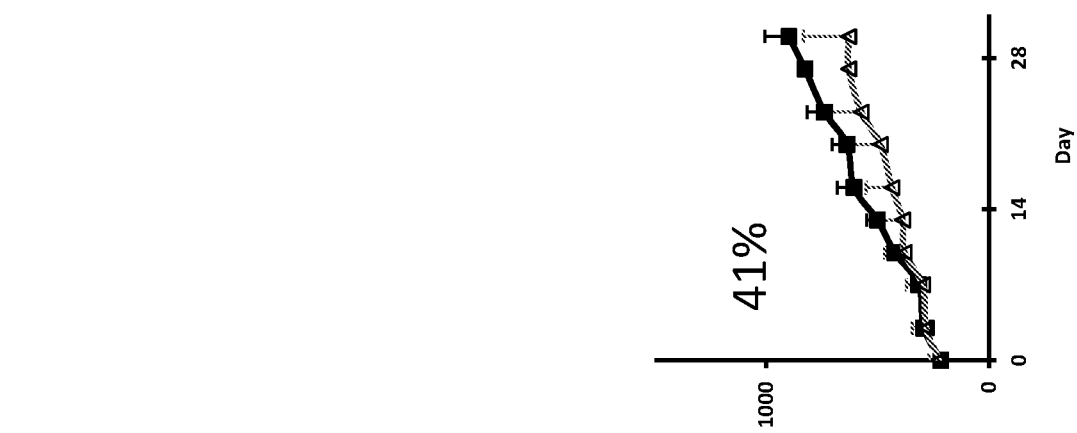
Figure 9G:
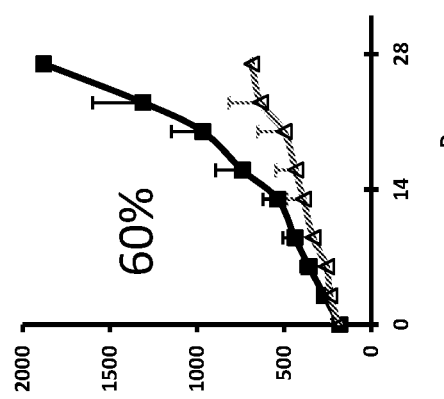
Figure 11A:
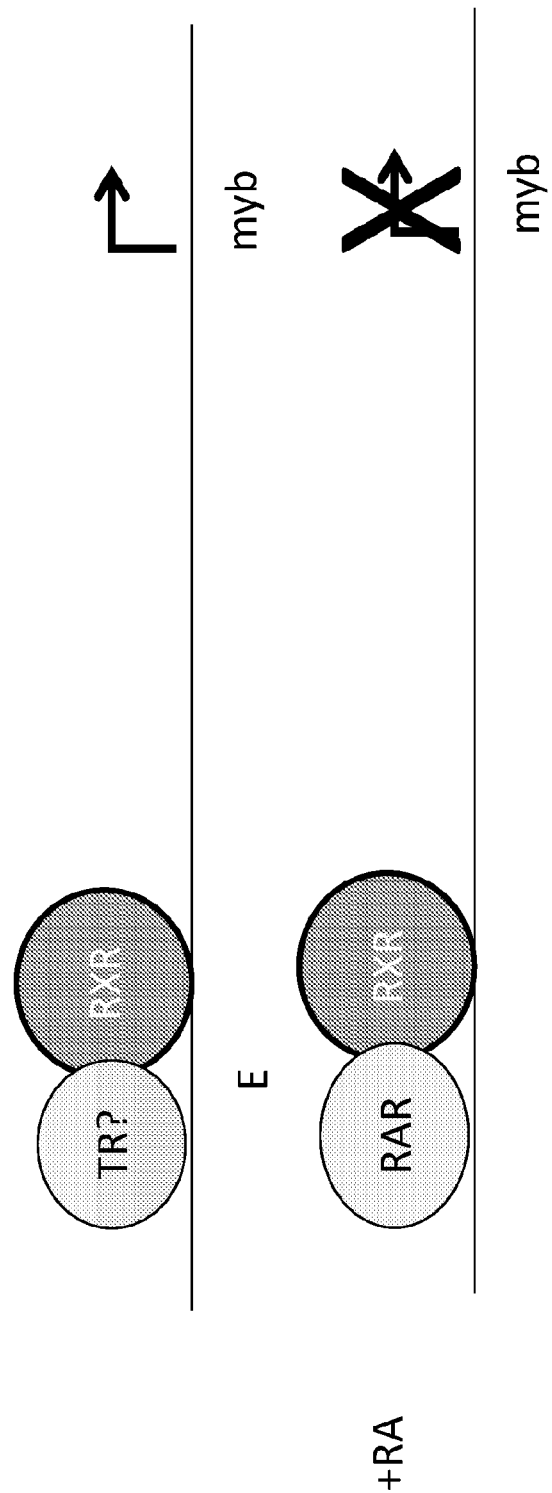
FIGS. 11A and 11B are schematic representation of various models of myb regulation.
Figure 11B:
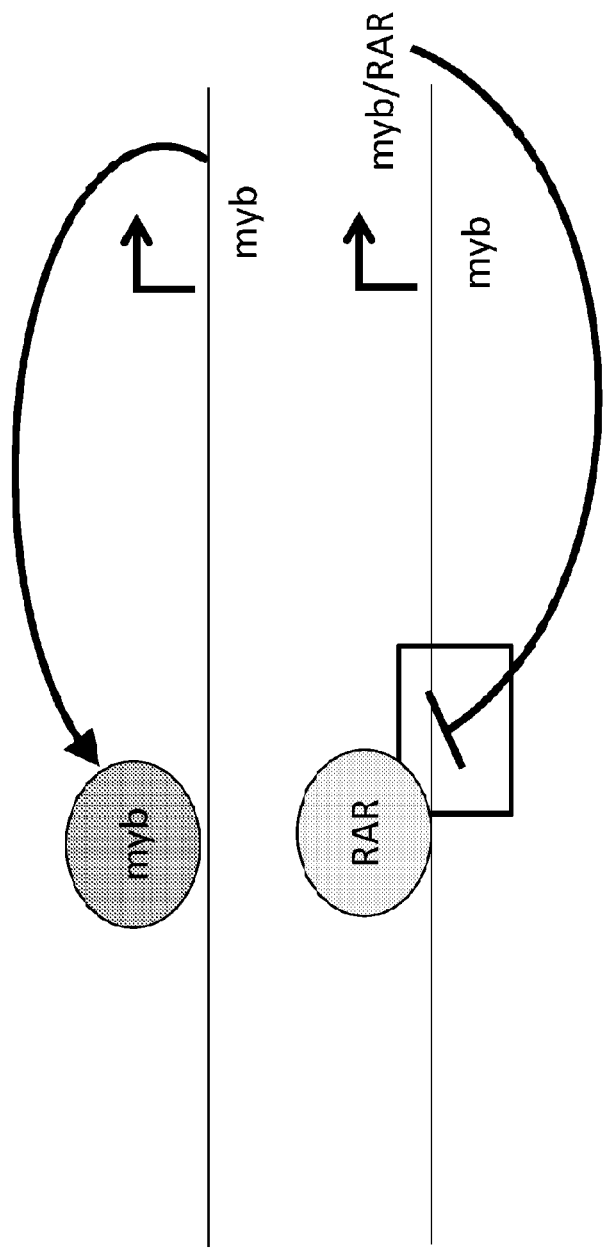

24, and 48 hours (FIG. 7). In addition, ATRA inhibited U937 proliferation as assessed by CellTiter-Glo (a luminescent cell viability assay) in a dose-dependent manner in two days (FIG. 8). The availability of ACC cell lines would be helpful in the studies, but the cells are very difficult to culture ex vivo and so the inventors opted to use U937 cells. Taken together, the screen revealed that RAs are potent suppressors of myb.

ACC patient derived xenograft studies in mice using three different primary patient lines showed an average tumor size inhibition across the three models of 88% for all-trans retinoic acid (ATRA), 86% for isotretinoin, and 53% for fenretinide, which are near the highest levels for any drugs tested in the xenograft models (FIGS. 9A-9I and Table 4) The data strongly indicates that RAs could lead to a therapy for ACC.

TABLE 4

Summary of tumor growth inhibition with retinoic acid agonists.

| | ACCx6 | ACCx9 | ACCx11 | Average |
|---|---|---|---|---|
| ATRA (tretinoin) | | | | 88% |
| 4 mg/mL | 81% | | 105% | |
| 3 mg/mL | | 78% | | |
| Isotretinoin (13-cis RA) | 69% | 95% | 94% | 86% |
| Fenretinide (4-HPR) | 60% | 57% | 41% | 53% |
| Average | 70% | 77% | 80% | 76% |

It is envisioned that ATRA treatment changes the chromatin landscape. The nuclear hormone receptors including the steroid receptors, androgen receptors, and retinoic acid receptors (RARs) bind to a common RXR receptor. The binding of one ligand to RXR could therefore block the response to another ligand, essentially preventing the transactivation potential or DNA-binding of the specific receptors. RA receptor agonists such as ATRA could thus block myb transcription directly. Indeed, RXR ChIP-seq on human leukemia K562 cells revealed binding sites at the myb locus (FIGS. 10A and 10B).

Discussion

The data strongly indicates that RAs could lead to a therapy for ACC. RAR binding directly at the myb locus may inhibit myb transcription, or RAR binding myb at the protein level upon RA treatment could disrupt the positive autoregulatory loop of myb expression due to RAR binding. Given the suppressor effect of various RA agonists on myb, it is predicted that ATRA treatment induces RAR and RXR binding at the myb gene locus, which reduces myb expression.

Acute promyelocytic leukemia (APL) due to a translocation resulting in PML-RARA fusion can be treated with an ATRA split dose of 45 mg/m2 per day, and the median plasma concentration in patients is approximately 1 µM on the first day of treatment. This RARA fusion in APL makes the fusion protein sensitive to RA treatment, which acts via a significantly different mechanism than the transcriptional mechanism that is proposed in ACC and lacks this RARA fusion. In APL, ATRA treatment is often combined with anthracycline chemotherapy (daunorubicin, idarubicin, or cytarabine), or, in low-risk patients (white blood cell count <10,000/µL and platelet count >40,000/µL), with arsenic trioxide (ATO). ATRA and ATO are believed to act as differentiation agents, and studies suggest that ATO may also induce apoptosis at concentrations of 0.5-2 µM through a separate pathway. It is likely that RAs such as ATRA may be used in combination with other drugs to suppress myb synergistically for the treatment of ACC tumors or to prevent tumor relapse.

The nuclear hormone receptors, including the steroid receptors, androgen receptors and retinoic acid receptors all bind to a common receptor called RXR. The binding of one ligand to RXR could therefore block the response to another ligand, essentially preventing the transactivation potential or DNA-binding of the specific receptors. Furthermore, pharmaceutical companies have developed a large number of nuclear hormone receptor modulators that may be therapeutically useful. Since myb functions as an oncogene in a variety of cancers, including breast cancer, pancreatic cancer and leukemia, RA suppression of myb may be therapeutically useful in other tumors in addition to ACC.

Materials and Methods

Zebrafish cell culture: Zebrafish embryo cultures were adapted from Xu (2013). Dissociated blastomere cells were grown in medium composed of 85% LDF medium, 5% heat inactivated FBS, and 10% zebrafish day 1 embryo extract. LDF medium contains 50% Leibowitz's L-15 (Invitrogen), 20% DMEM (Invitrogen), and 30% DMEM/F-12 (Invitrogen), supplemented with 0.018% sodium bicarbonate, 15 mM HEPES (Invitrogen), 1% L-Glutamine (Invitrogen), 10 nM sodium selenite (Sigma-Aldrich), 1% N2 (Invitrogen), 2% B27 (Invitrogen), 1% Penicillin-Streptomycin (Invitrogen), and 0.2% Primocin (InvivoGen).

Screening procedures: Two 384-well plates were coated with 0.1% gelatin for each chemical library plate. Males of the c-myb:GFP transgenic line were set up overnight with casper females and kept separated until morning when they were mixed for mating. Embryos were washed twice with E3 embryo water and treated with pronase to remove chorions. Dechorionated embryos were washed with E3 embryo water and collected into tubes containing media. Embryos were disassociated by shaking ~10 times and were filtered through a 40 µm nylon mesh filter. Resulting single cells were diluted with medium and aliquoted 30 µl per well into the 384-well plates at approximately 2 embryo equivalents per well. Chemicals were dispensed immediately afterwards with an Agilent Bravo robot. Chemicals from the libraries were diluted 300 times with LDF medium and were aliquoted 10 µl per well for a final concentration of approximately 33 µM. Libraries tested include Evotec's NIH (720), Sigma's Library of Pharmacologically Active Compounds (LOPAC, 1,440), BIOMOL ICCB Known Bioactives (480), and ChemBridge's Nuclear Hormone Receptor (NHR) and Kinacore library (1,200). Cells were cultured in a 28° C. incubator with 5% CO2. Two days later, cells were imaged by a Yokogawa Cell Voyager 7000 imager. Images were analyzed by ImageJ and MatLab and confirmed by eye.

RA dose response experiments were plated similarly in LDF medium with the appropriate RA concentration. Sorted c-myb:GFP+ cells were collected from 72 hpf transgenic embryos that were homogenized: embryos were finely chopped and dissociated using Liberase (Roche), cell suspensions were filtered, and 58,000 GFP+ live cells were collected using a FACS Aria cell sorter (BD Biosciences). Cells were cultured for 6 hours in LDF medium, and then collected for qPCR.

In situ hybridization: In situ hybridization was done for c-myb as described in North (2007). Wildtype AB zebrafish embryos were treated with RAs in the E3 water at the indicated doses during 48-72 hpf, after which point they were fixed in 4% PFA. Qualitative scoring (number of embryos with altered number of HSCs scored) of c-myb positive cells was conducted by assessing the caudal hematopoietic tissue (CHT) region by the tail.

Cell culture: U937 cells were grown in RPMI 1640 (Life Technologies), 10% heat inactivated FBS, and 1% Penicillin-Streptomycin (Invitrogen). CellTiter-Glo Luminescent Cell Viability Assay (Promega) was performed as per manufacturer's instructions. Cell viability was assessed at day 2.

Quantitative PCR: Total RNA from cells was extracted using Qiagen RNeasy Mini Kit, and random primed cDNA was generated (Invitrogen, SuperScript III First-Strand Synthesis System). The SsoFast EvaGreen (Biorad) method was used to quantify cDNAs of interest, which are represented as the fold change in transcript level. The amount of cDNA starting material for each sample was normalized in relation to species-specific β-actin expression for zebrafish samples, and both gapdh and β-actin expression for human samples. The primer sequences used were zebrafish myb: forward, 5'-TGATGCTTCCCAACACAGAG-3' (SEQ ID No:1), reverse, 5'-TTCAGAGGGAATCGTCTGCT-3' (SEQ ID No:2); zebrafish β-actin: forward, 5'-CGAGCAGGA-GATGGGAACC-3' (SEQ ID No:3), reverse, 5'-CAACG-GAAACGCTCATTGC-3' (SEQ ID No:4); human myb: forward, 5'-GGCAGAAATCGCAAAGCTAC-3' (SEQ ID No:5), reverse, 5'-ACCTTCCTGTTCGACCTTCC-3' (SEQ ID No:6); human gapdh: forward, 5'-CTGACTTCAACA-GCGACACC-3' (SEQ ID No:7), reverse, 5'-TGCTGTAGC-CAAATTCGTTGT-3' (SEQ ID No:8); human β-actin: forward, 5'-AGTGGGGTGGCTTTTAGGAT-3' (SEQ ID No:9), reverse, 5'-CCGAGGACTTTGATTGCACA-3' (SEQ ID No:10).

ChIP-seq: ChIP-seq was performed as described in Lee (2006) and Buenrostro (2013) with conditions optimized for K562 cells. ~1×108 K562 cells were crosslinked fixed in formaldehyde and subjected to ChIP with RXR antibody (Santa Cruz, sc-774X, 10 µg). Libraries were prepared by using the NEBNext Multiplex Oligos for Illumina kit (NEB) and run on an Illumina HiSeq 2000.

Xenograft experiments: To generate ACC xenografts, 1×106 viable ACC cells were injected into the flank of female nude (Foxn1nu) mice for in vivo drug testing of ACCx6, ACCx9, and ACCx11 lines. Once tumors were visible, the mice were randomized to receive vehicle control or drug until reaching a minimal tumor volume of 1,000 mm3. The mice in each group were treated with an oral flat dose five times weekly (po qdx5) for four cycles (two days off between cycles). The exact dosing was determined based on an initial MTD tolerability study and published literature reports. Five mice per group were treated for ACCx6 and ACCx9, and four mice per group were treated for ACCx11 (five mice in the control ACCx11 group), and the tumor volumes were quantified. Mice were treated with a flat dose of 0.2 mL orally of: 30 mg/mL isotretinoin; 40 mg/mL fenretinide; 4 mg/mL ATRA for ACCx6 and ACCx11 or 3 mg/mL ATRA for ACCx9. Mouse procedures used in this study were approved by the IACUC at South Texas Accelerated Research Therapeutics (San Antonio, Tex.).

References

1 Drier, Y. et al. An oncogenic MYB feedback loop drives alternate cell fates in adenoid cystic carcinoma. *Nat Genet* 48, 265-272, doi:10.1038/ng.3502 (2016).
2 Adelstein, D. J., Koyfman, S. A., El-Naggar, A. K. & Hanna, E. Y. Biology and management of salivary gland cancers. *Seminars in radiation oncology* 22, 245-253, doi:10.1016/j. semradonc.2012.03.009 (2012).
3 Ho, A. S. et al. The mutational landscape of adenoid cystic carcinoma. *Nat Genet* 45, 791-798, doi:10.1038/ng.2643 (2013).
4 Ramsay, R. G. & Gonda, T. J. MYB function in normal and cancer cells. *Nat Rev Cancer* 8, 523-534, doi:10.1038/nrc2439 (2008).
5 Persson, M. et al. Recurrent fusion of MYB and NFIB transcription factor genes in carcinomas of the breast and head and neck. *Proc Natl Acad Sci USA* 106, 18740-18744, doi:10.1073/pnas.0909114106 (2009).
6 Xu, C. et al. A zebrafish embryo culture system defines factors that promote vertebrate myogenesis across species. *Cell* 155, 909-921, doi:10.1016/j.cell. 2013.10.023 (2013).
7 Howe, K. et al. The zebrafish reference genome sequence and its relationship to the human genome. *Nature* 496, 498-503, doi:10.1038/nature12111 (2013).
8 Langheinrich, U. Zebrafish: a new model on the pharmaceutical catwalk. *BioEssays: news and reviews in molecular, cellular and developmental biology* 25, 904-912, doi:10.1002/bies. 10326 (2003).
9 North, T. E. et al. Prostaglandin E2 regulates vertebrate haematopoietic stem cell homeostasis. *Nature* 447, 1007-1011, doi:10.1038/nature05883 (2007).
10 Adamson, P. C. All-Trans-Retinoic Acid Pharmacology and Its Impact on the Treatment of Acute Promyelocytic Leukemia. *The oncologist* 1, 305-314 (1996).
11 Khoo, K. C., Reik, D. & Colburn, W. A. Pharmacokinetics of isotretinoin following a single oral dose. *Journal of clinical pharmacology* 22, 395-402 (1982).
12 Degos, L. & Wang, Z. Y. All trans retinoic acid in acute promyelocytic leukemia. *Oncogene* 20, 7140-7145, doi: 10.1038/sj.onc.1204763 (2001).
13 Lo-Coco, F. et al. Targeted Therapy Alone for Acute Promyelocytic Leukemia. *N Engl J Med* 374, 1197-1198, doi:10.1056/NEJMc1513710 (2016).
14 Zhu, J., Lallemand-Breitenbach, V. & de The, H. Pathways of retinoic acid- or arsenic trioxide-induced PML/RARalpha catabolism, role of oncogene degradation in disease remission. *Oncogene* 20, 7257-7265, doi:10.1038/sj.onc.1204852 (2001).
15 Lee, T. I., Johnstone, S. E. & Young, R. A. Chromatin immunoprecipitation and microarray-based analysis of protein location. *Nature protocols* 1, 729-748, doi: 10.1038/nprot.2006.98 (2006).
16 Buenrostro, J. D., Giresi, P. G., Zaba, L. C., Chang, H. Y. & Greenleaf, W. J. Transposition of native chromatin for fast and sensitive epigenomic profiling of open chromatin, DNA-binding proteins and nucleosome position. *Nature methods* 10, 1213-1218, doi:10.1038/nmeth.2688 (2013).

Figures 12A, 12B, 12C:
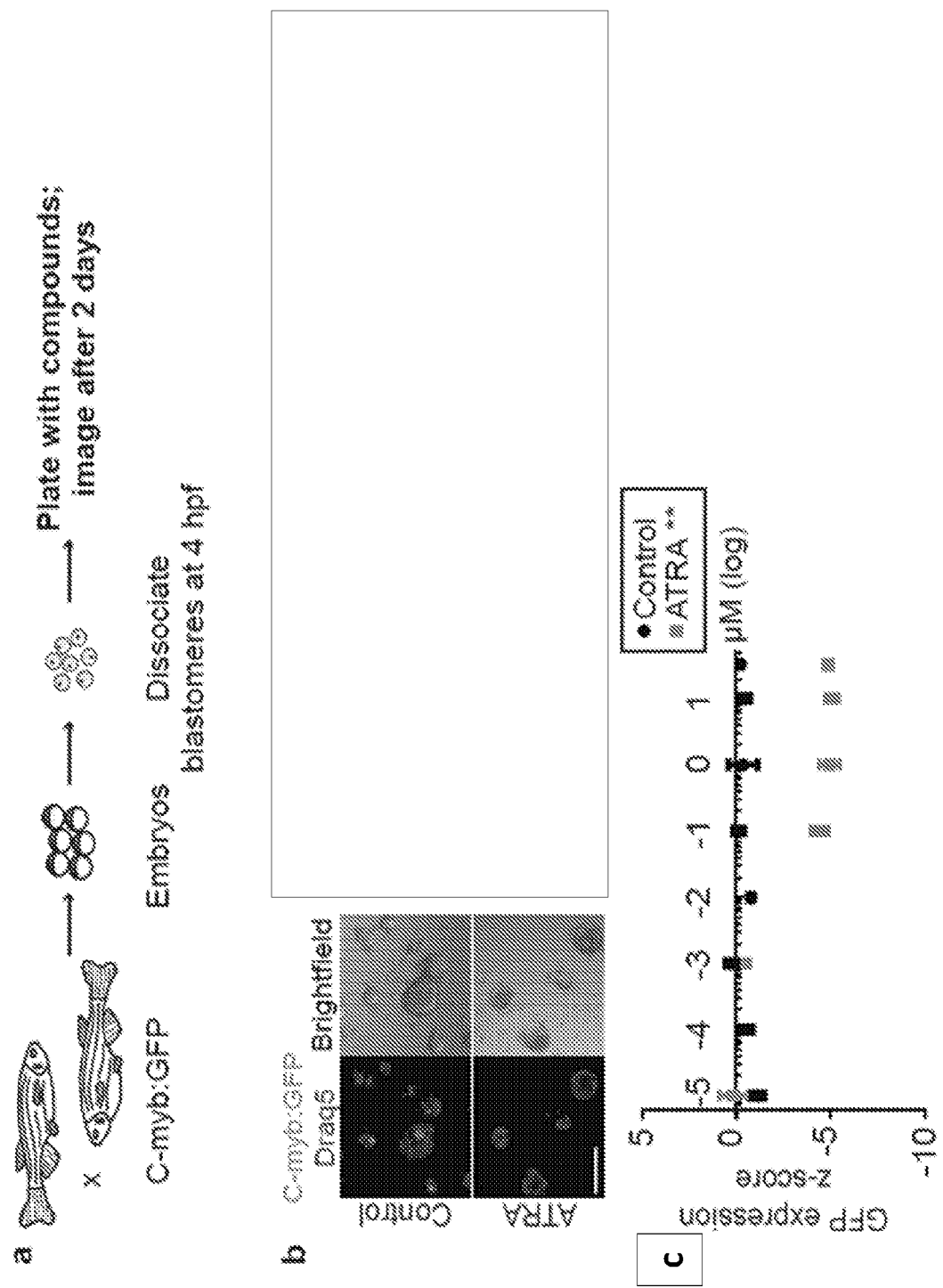
FIG. 12A is a schematic showing high-throughput image-based chemical screening assay. Chemical genetic screen identifies retinoic acid agonists as downregulators of c-myb: GFP. C-myb:GFP transgenic embryos were collected and dissociated at sphere stage. Resulting blastomere cells were plated into 384-well plates with chemicals in duplicate. After 2 days, the 384-well plates were imaged using a Yokogawa Cell Voyager 7000 and analyzed.
FIG. 12B shows sample images from the screen. Hits were visually inspected for normal embryoid body formation as an indicator for toxicity.
FIG. 12C shows dose response curves (n=4). **p<0.01 by unpaired one-tailed t-test, mean with s.e.m. Scale bar, 50 μm. hpf, hours post fertilization.

Example 2: Zebrafish Chemical Genetic Screen Identifies Regulators of c-Myb Expression The inventors previously reported a chemical genetic screen that identified inducers of myogenesis using an embryonic blastomere culture system in zebrafish. Here, this culture screening system is adapted to find modulators of c-myb, a marker of HSPCs. A culture system involving a BAC transgenic reporter with GFP at the ATG of the c-myb gene is used. Embryos were dissociated into single cells at sphere stage (4 hours post fertilization, hpf), and plated with chemicals for two days until fluorescence was evaluated (FIG. 12A). Gene expression analysis of sorted c-myb:GFP expressing cells demonstrated that the cells contained a mixture of blood, neural, and epithelial cell types, thereby proving that c-myb:GFP was expressed in similar tissues as the endogenous gene.

Figures 18A, 18B, 18C, 18D:
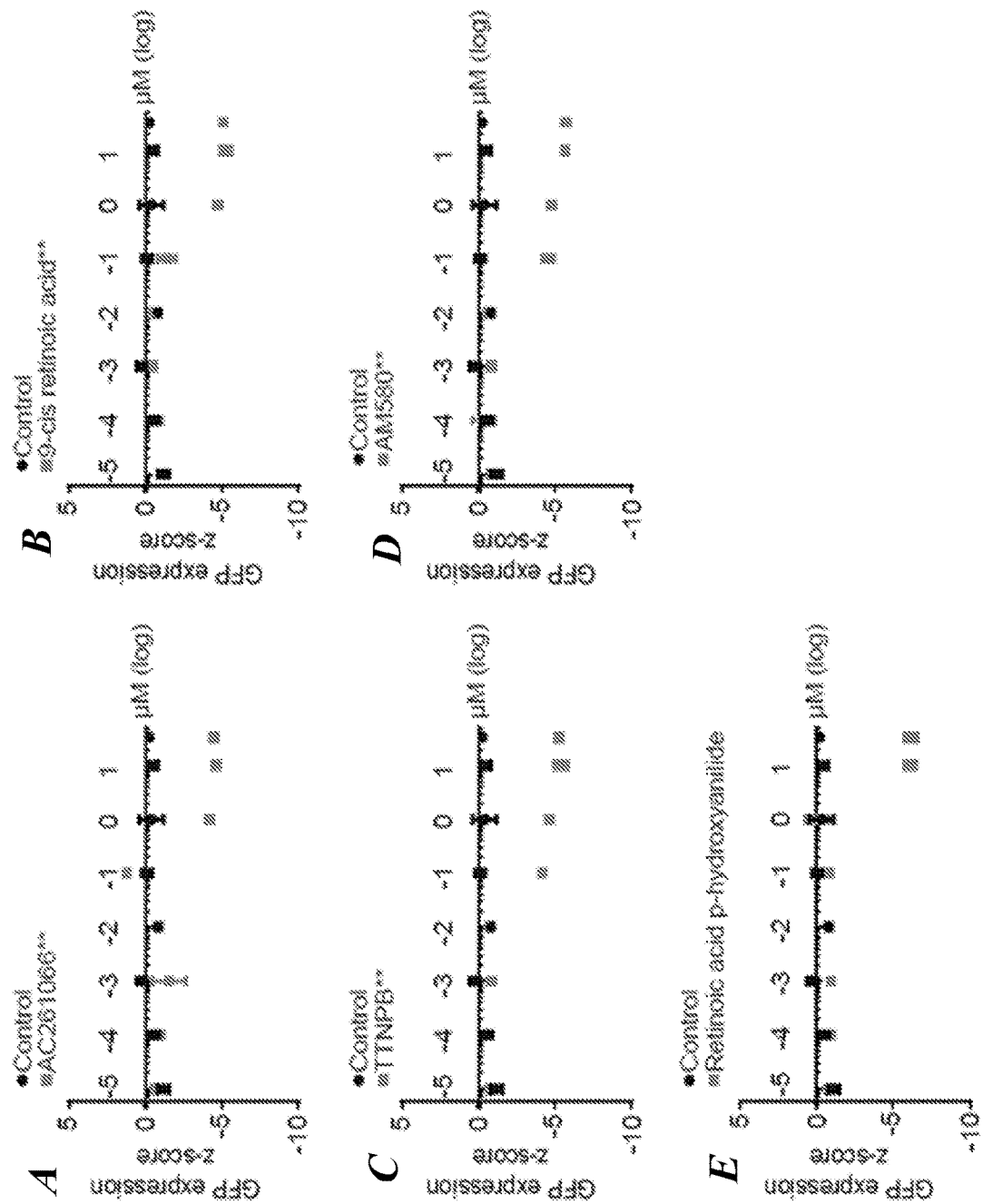
FIGS. 18A-18C show dose response curves (n=4) for retinoic acid agonists AC261066 (FIG. 18A), 9-cis retinoic acid (FIG. 18B), TTNPB (FIG. 18C), AM580 (FIG. 18D) and p-hydroxyanilide (FIG. 18E). **p<0.01 by unpaired one-tailed t-test, mean with s.e.m. Chemical genetic screen identifies retinoic acid agonists as downregulators of c-myb: GFP.

3,840 bioactive small molecules were screened in duplicate for suppression of c-myb:GFP and identified 107 chemical hits (2.8% hit rate, z-score <1.44 and >70% c-myb:GFP downregulation). The z-score represents the average across the two plates and normalizes for variable amounts of GFP fluorescence among the plates screened. Visual inspection revealed 23 hits had normal embryoid body formation. This suggested that the c-myb:GFP downregulation observed was specific and not due to toxicity effects of the chemicals (FIG. 12B). Retinoic acid agonists were identified as potent suppressors of c-myb:GFP expression in the blastomere cultures at low concentrations (Table 3, FIGS. 12C and 18). Given that c-myb:GFP was expressed by a variety of different cell types in the culture system, the retinoic acid effects on c-myb expression can occur in many tissues.

Figures 13A, 13B, 13C, 13D:
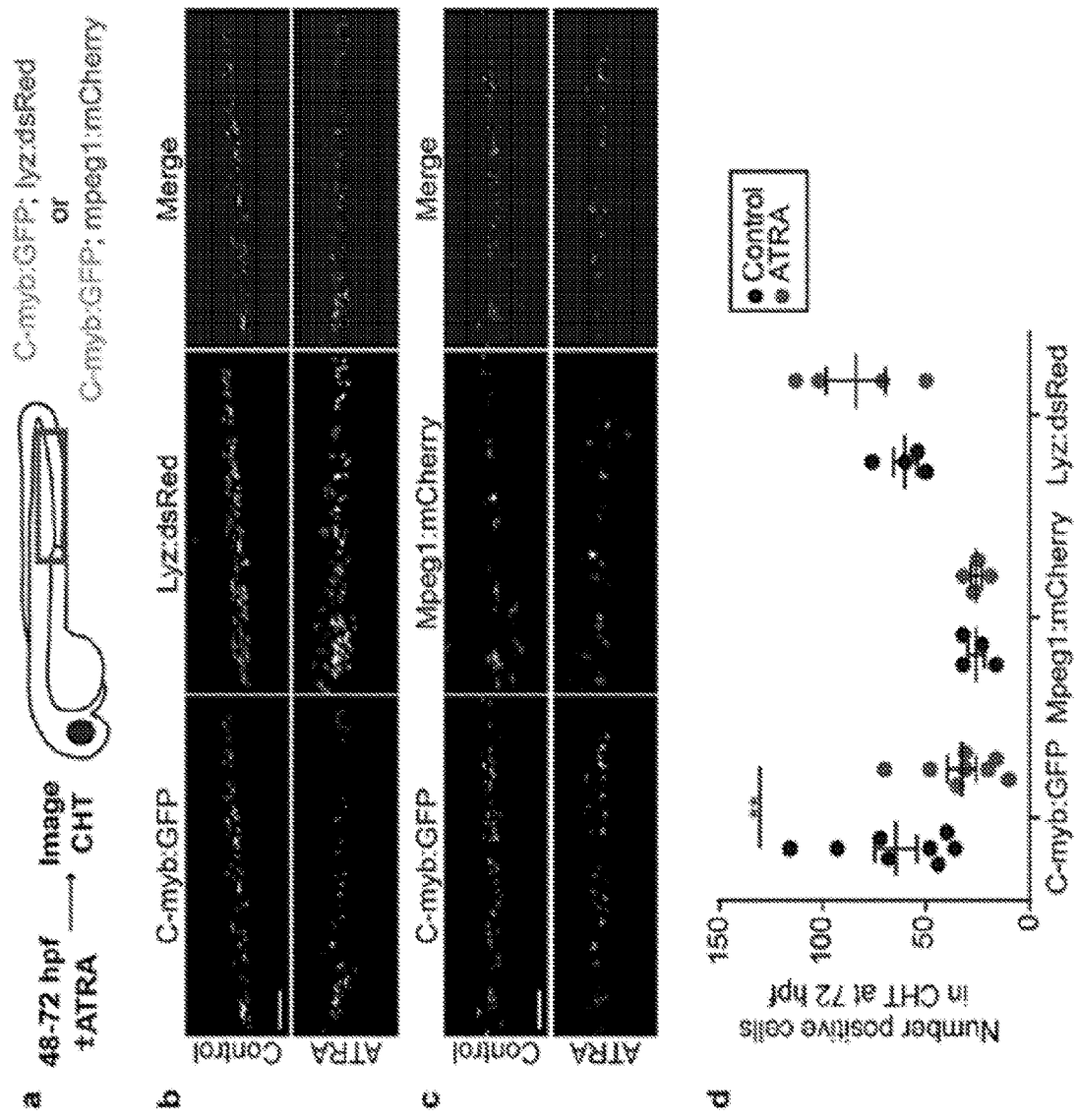
FIG. 13A shows that ATRA decreases c-myb:GFP positive cells in vivo. Double transgenic c-myb:GFP; mpeg1: mCherry or c-myb:GFP; lyz:dsRed embryos were treated at 48-72 hpf with ATRA and then the CHT region was imaged.
FIG. 13B is an image showing ATRA decreased c-myb: GFP positive cells in the CHT at 72 hpf, but had no significant effect on lyz:dsRed positive cells.
FIG. 13C is an image showing ATRA decreased c-myb: GFP positive cells in the CHT at 72 hpf, but had no significant effect on mpeg1:mCherry positive cells.
FIG. 13D is a graph showing ATRA decreased c-myb: GFP positive cells in the CHT at 72 hpf, but had no significant effect on mpeg1:mCherry or lyz:dsRed positive cells. **p<0.01 by unpaired one-tailed t-test, mean with s.e.m. Scale bars, 70 μm. CHT of n=4 embryos scored for each condition, and combined for the c-myb:GFP population. hpf=hours post fertilization, CHT=caudal hematopoietic tissue.
Figures 14A, 14B, 14C, 14D, 14E:
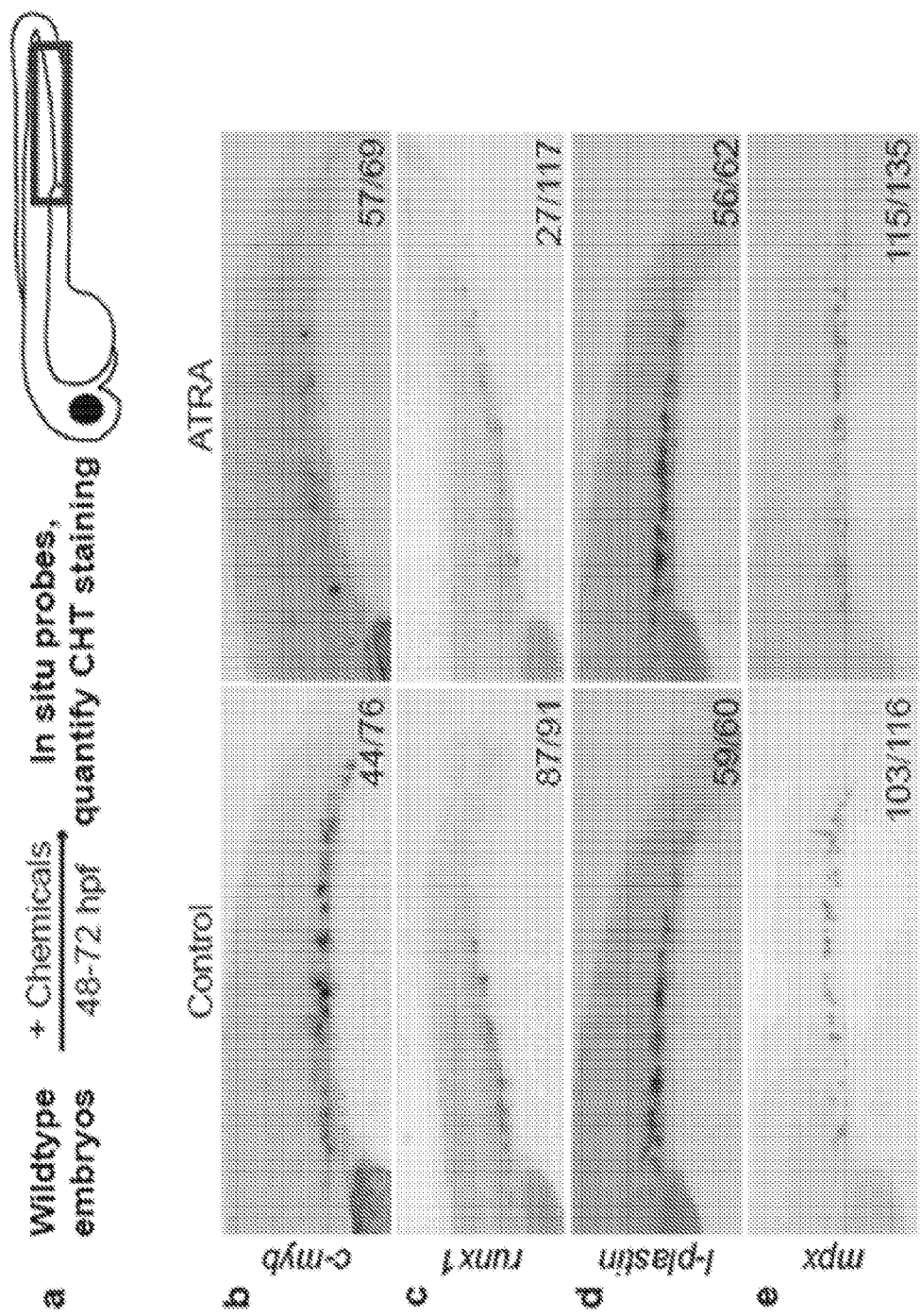
FIG. 14A shows that ATRA downregulates c-myb and runx1 in vivo. Wildtype embryos were treated at 48-72 hpf, fixed at 72 hpf, and stained by in situ hybridization.
FIG. 14B is a representative image showing ATRA treatment decreased staining for c-myb in the CHT. Embryos were scored as high, medium, or low, and summed across 3 independent experiments.
FIG. 14C is a representative image showing ATRA treatment decreased staining for runx1 in the CHT. Embryos were scored as high, medium, or low, and summed across 3 independent experiments.
FIG. 14D is a representative image showing ATRA treatment did not decrease staining for 1-plastin in the CHT. Embryos were scored as high, medium, or low, and summed across 3 independent experiments.
FIG. 14E is a representative image showing ATRA treatment did not decrease staining for mpx in the CHT. Embryos were scored as high, medium, or low, and summed across 3 independent experiments.
Figures 19A, 19B:
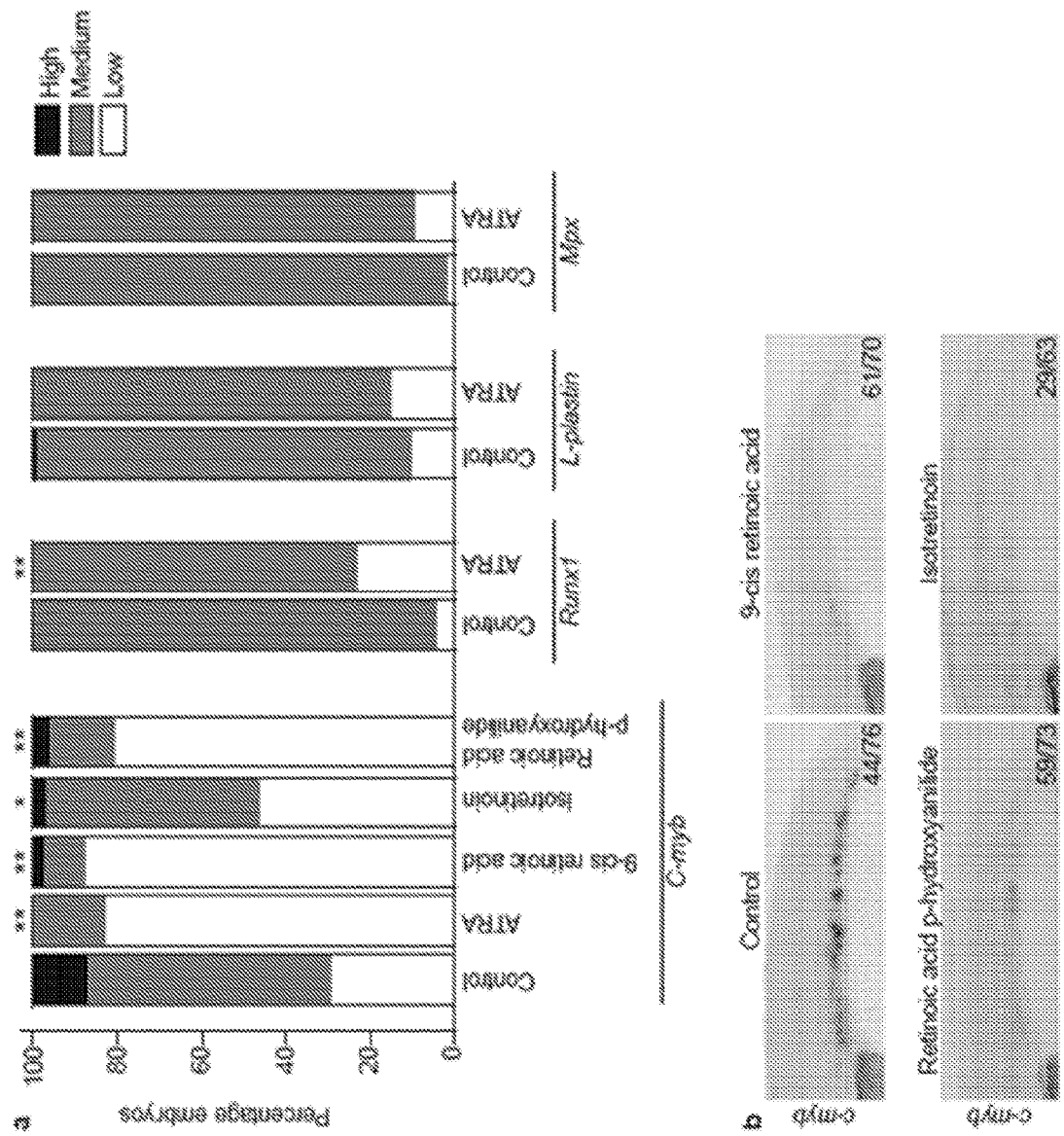
FIG. 19A is a bar graph showing in situ hybridization in the CHT region after retinoic acid agonist treatments. Retinoic acids downregulate c-myb in vivo.
FIG. 19B is a representative image showing c-myb in situ hybridization. Embryos were scored as high, medium, or low, and summed across 3 independent experiments. *p<0.05; **p<0.01, by Chi-square (for c-myb, 1-plastin, and mpx quantification) or one-tailed Fisher's Exact Test (for runx1 quantification).

Retinoic acid agonists decrease c-myb positive cells in vivo: C-myb is required for HSPC formation in zebrafish and mammalian blood development. C-myb is also expressed in mature myeloid cells such as neutrophils and macrophages. Thus, it was investigated if retinoic acid treatment functions on HSPCs and myeloid cells located in the subsequent hematopoietic niche between 48-72 hpf. The inventors quantified the number of c-myb:GFP+ cells of live zebrafish embryos treated with ATRA in double-transgenic embryos along with mpeg1:mCherry+ (macrophage marker) or lyz:dsRed+ (neutrophil marker) cells at 72 hpf (FIG. 13A). They also examined alterations on endogenous hematopoietic populations by whole mount in situ hybridization in ATRA treated wildtype AB embryos (FIG. 14A). In embryos treated with ATRA, there was a significant decrease in the number of c-myb:GFP+ cells (FIG. 13A-13D) and c-myb and runx1 expression (FIGS. 14B, 14C and 19A). Other retinoic acid agonists besides ATRA also strongly decreased c-myb levels (FIG. 19B). There was no significant difference in mpeg1:mCherry+ and lyz:dsRed+ cells (FIG. 13B-13D) or mpx (neutrophil marker) and l-plastin (macrophage and neutrophil marker) expression (FIG. 14D-14E). Taken together, these findings argue strongly for a specific inhibitory role of retinoic acid agonists on the c-myb positive HSPC population that does not affect mature myeloid cells.

Figures 15A, 15B:
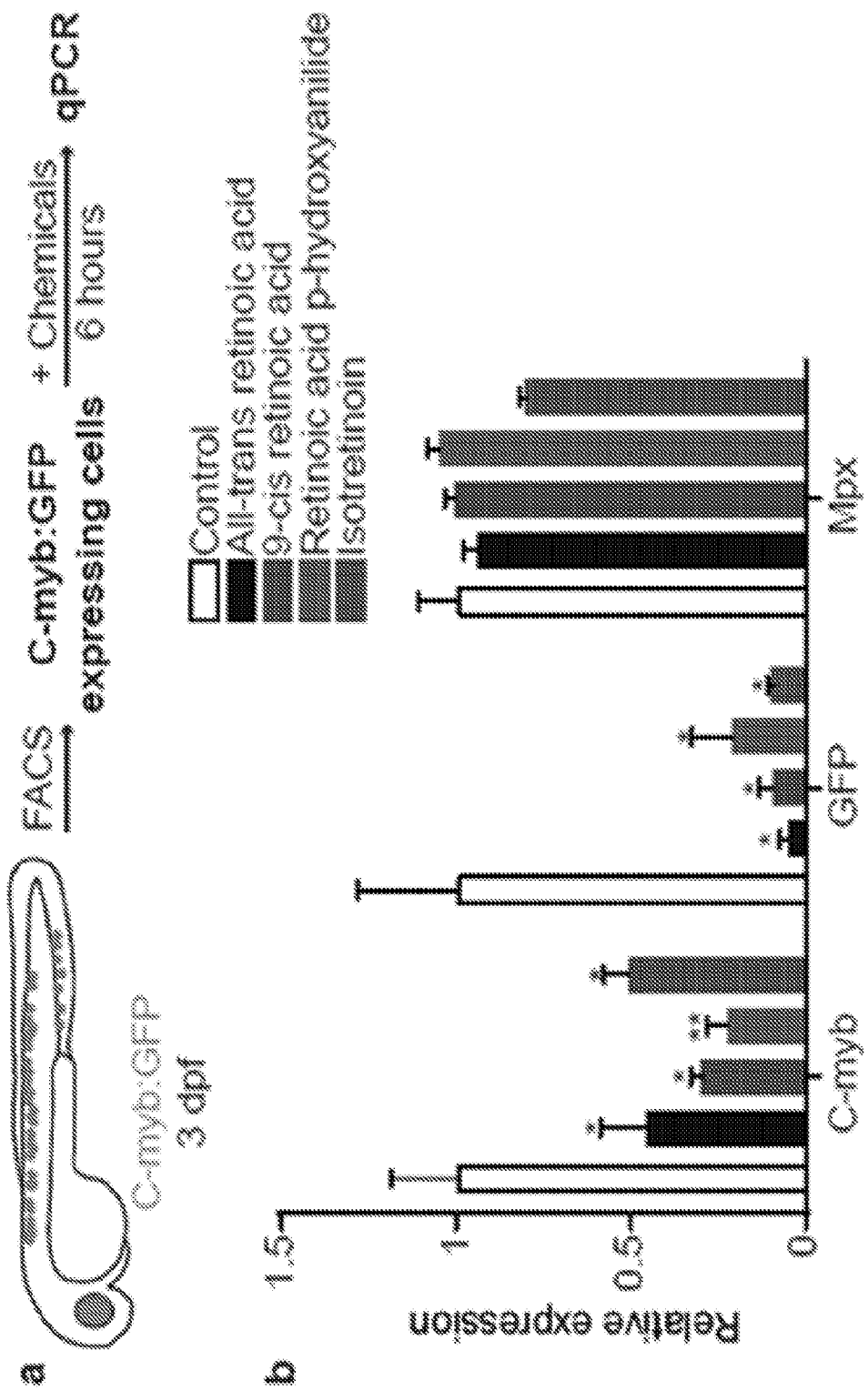
FIG. 15A shows that retinoic acids downregulate endogenous c-myb expression in c-myb:GFP expressing cells. C-myb:GFP positive cells were sorted from 3 dpf transgenic embryos, plated with chemicals for 6 hours, and analyzed by qPCR.
FIG. 15B is a bar graph showing expression of genes after retinoic acid agonists treatment shown relative to control cells (n=3). *p<0.05; **p<0.01, by unpaired one-tailed t-test, mean with s.e.m. dpf, days post fertilization.

Retinoic acid agonists work rapidly to downregulate c-myb expression in isolated tissues: To examine the role of retinoic acids on endogenous c-myb expression, c-myb:GFP expressing cells were sorted from 72 hpf transgenic embryos and were treated ex vivo with 1 µM retinoic acid agonists for 6 hours (FIG. 15A). At this stage, transgenic zebrafish express c-myb:GFP in blood, neural, hatching gland, and eye tissues. Retinoic acid treatments caused a rapid decline in c-myb and GFP transcript expression, whereas mpx gene expression was unaffected (FIG. 15B), in accordance with the in vivo findings.

Figure 16:
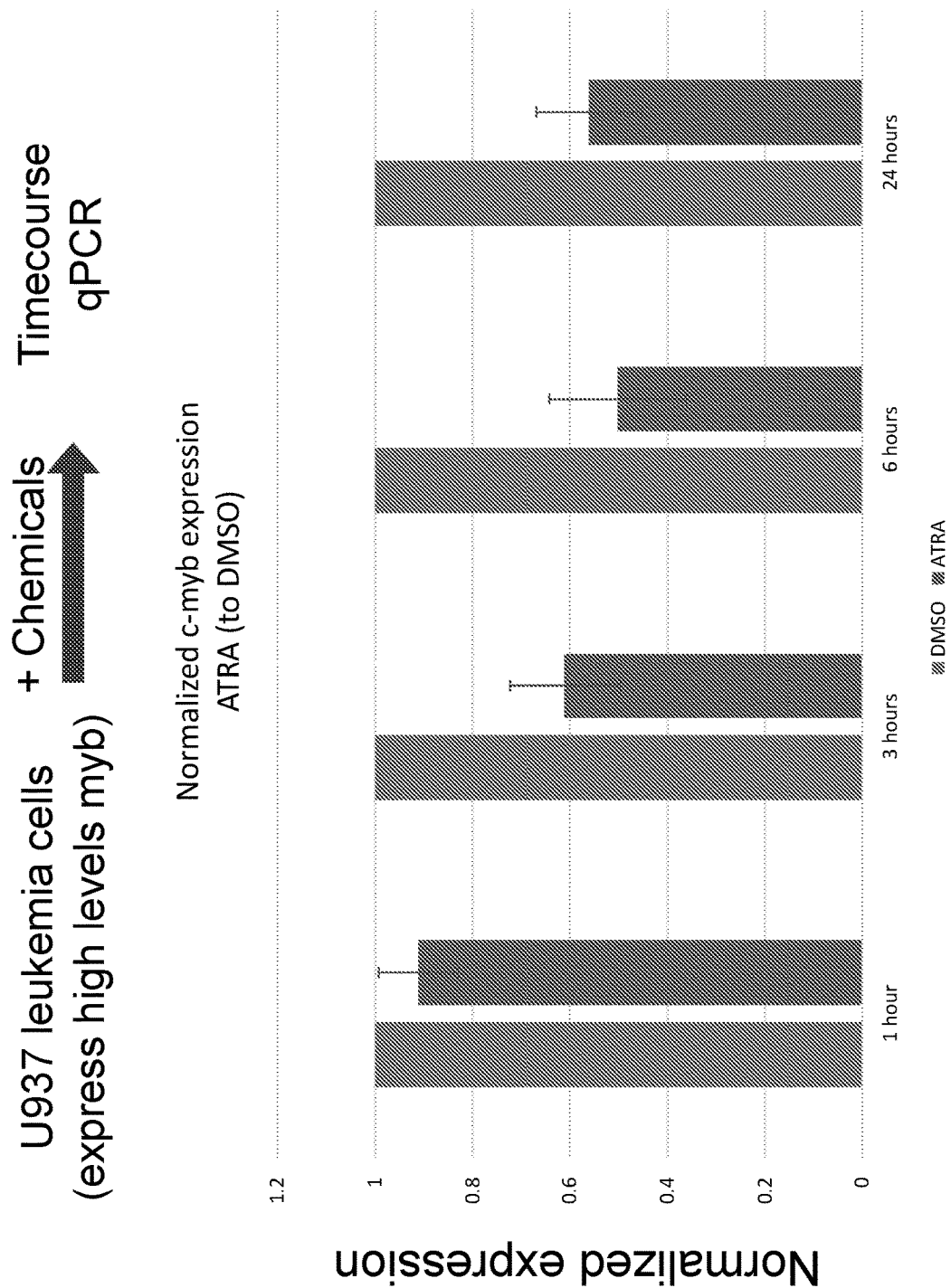
FIG. 16 is a bar graph showing normalized expression of c-myb after ATRA treatment This is shown relative to control cells (n=3). **p<0.01, by unpaired one-tailed t-test, mean with s.e.m. As can be seen, retinoic acid agonists downregulate endogenous c-myb expression. Time course treatment was done to assess c-myb transcript levels by qPCR in U937 cells (human myeloid leukemia cell line).
Figure 20:
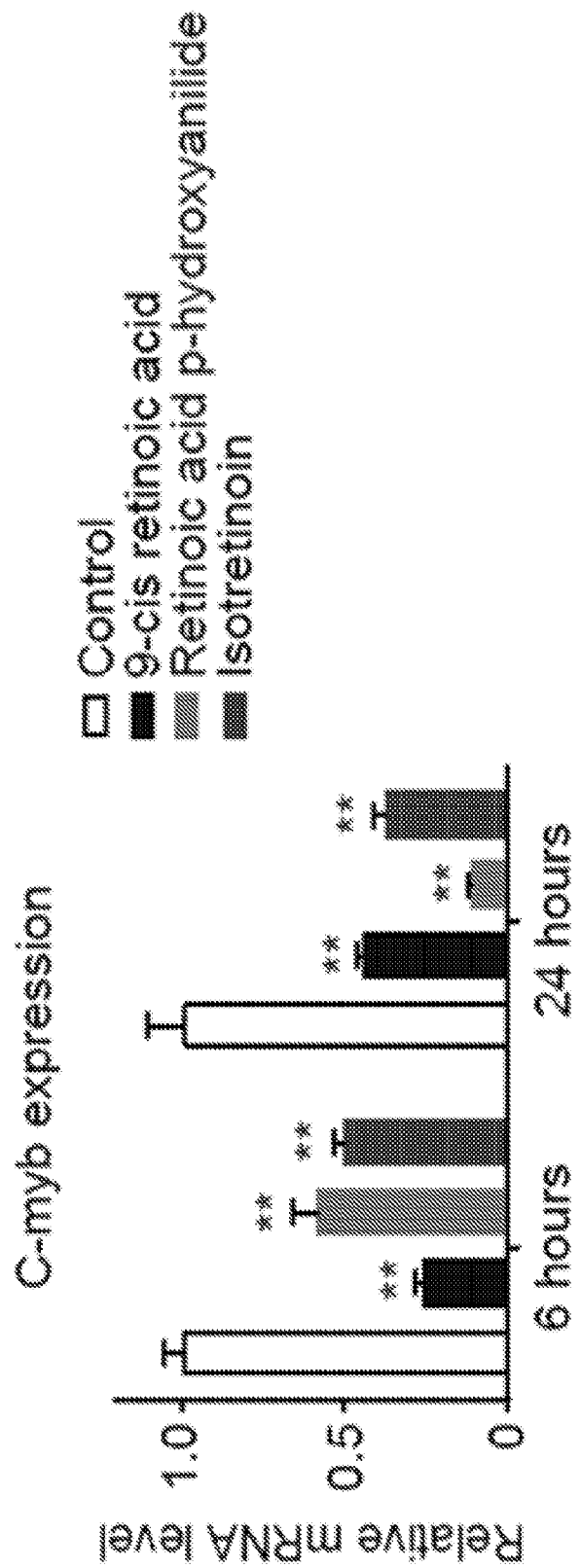
FIG. 20 is a bar graph showing relative transcript expression of c-myb in U937 cells after treatment duration indicated (n=3). **p<0.01, by unpaired one-tailed t-test, mean with s.e.m.

It was predicted that the retinoic acid downregulation of c-myb expression in zebrafish embryos and cell cultures could likewise act in mammalian tissues. As there are no ACC cell lines available for in vitro analysis, human U937 cells were studied. U937 cells, a myeloid leukemia line, express high levels of c-myb. U937 cells downregulated c-myb expression within 3 hours of ATRA treatment and for extended periods of time (FIG. 16), which suggested a direct transcriptional mechanism of regulation. Other retinoic acid agonists that were able to decrease c-myb expression were also analyzed (FIG. 20). Retinoic acid binds retinoic acid receptor (RAR α, β, or γ), which exists as a heterodimer with retinoid X receptor (RXR) and acts to control gene transcription upon ligand binding. Although 9-cis retinoic acid is a natural ligand of both pan-RAR and RXR, the reduction in c-myb gene expression which was observed with the pan-RAR agonists ATRA, retinoic acid p-hydroxyanilide, and isotretinoin strongly indicated that signaling via RAR specifically was responsible for c-myb downregulation. Retinoic acid agonists inhibited U937 proliferation in a dose dependent manner after 48 hours of treatment (FIG. 8), suggesting that the acute reduction of c-myb and the transcriptional response to retinoic acid leads to a proliferative defect.

Retinoic acid agonists slow ACC tumor growth in vivo: MYB translocations are near universal features in ACC where the MYB gene regulatory elements are maintained in the resulting fusions. The nuclear hormone receptors, including the steroid receptors, androgen receptors, and RARs, bind to a common RXR receptor. The binding of one ligand to RXR could therefore block the response to another ligand, essentially preventing the transactivation potential or DNA-binding of the specific receptors. Hence, ATRA, as a retinoic acid agonist, could block MYB transcription directly, especially given the rapid inhibition in c-myb gene expression which was observed by retinoic acid treatments. By shutting down transcription of the MYB gene, it was reasoned that it may be possible to modify the course of the disease with retinoic acid treatments by disrupting positive feedback loops involving MYB.

Figures 17A, 17B, 17C, 17D, 17E, 17F, 17G, 17H:
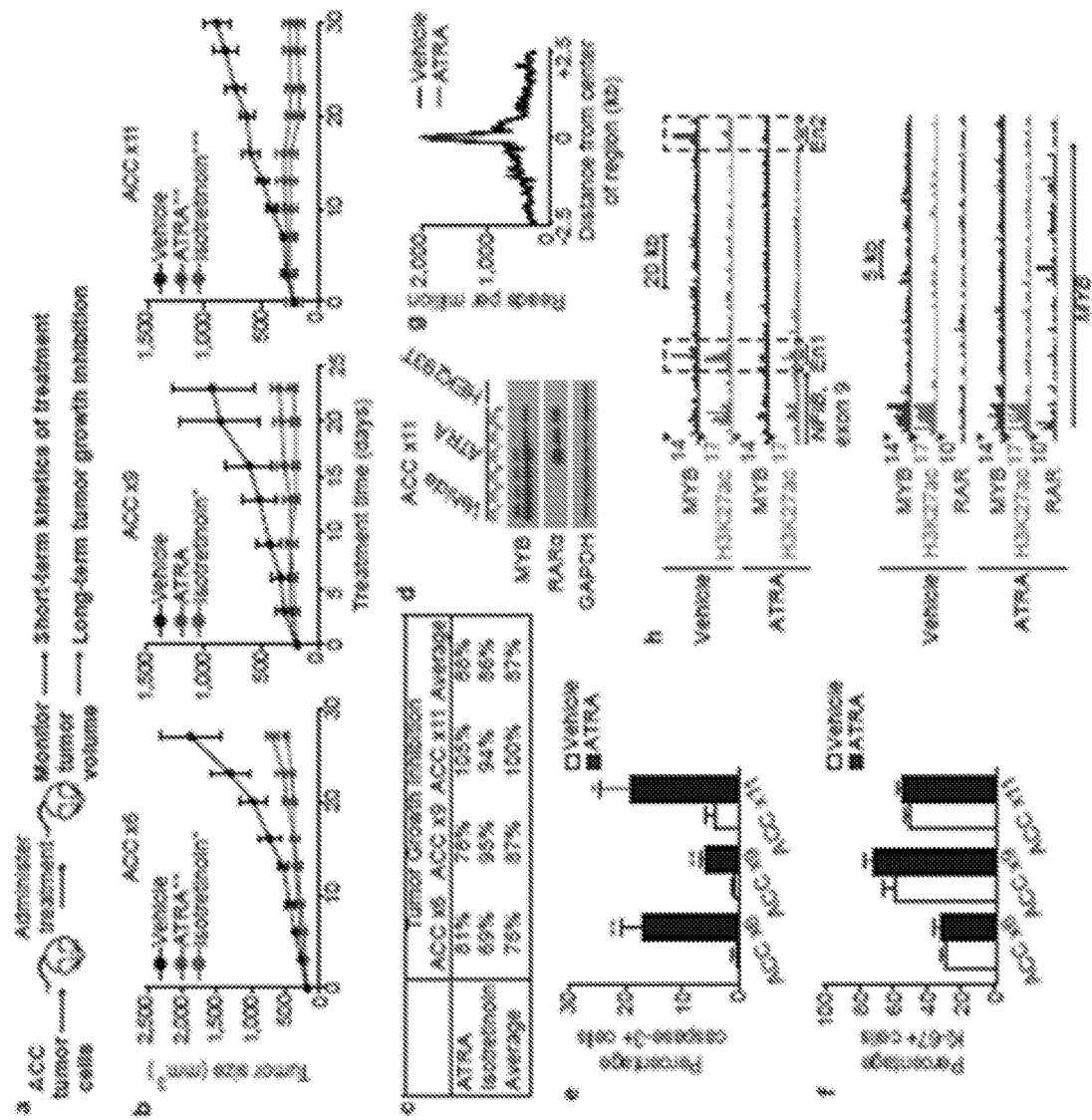
FIG. 17A shows an experimental design for ACC xenotransplantation trials. Retinoic acids slow tumor growth in ACC primagrafts.
FIG. 17B is a graph showing average tumor size from 4-9 mice per group during the xenotransplantation trial period.
FIG. 17C is a table showing average tumor growth inhibition across the different human tumors and treatments shown in FIG. 17B.
FIG. 17D shows protein expression of MYB (bands showing wildtype and translocated fusion) and RARα in individual ACC x11 primagrafts at the conclusion of the xenotransplantation trial in FIG. 17B (3 primagrafts from different mice shown for each group). HEK293T cell lysate is a negative control lacking MYB expression.
FIG. 17E is a bar graph showing percentage of cleaved caspase-3 positive nuclei quantified from immunohistochemistry sections of primagraft tumors at the conclusion of the xenotransplantation trial in FIG. 17B (n=3 images quantified, >200 nuclei each). ATRA treatment induced more cell death in the tumors.
FIG. 17F is a bar graph showing percentage of cleaved Ki-67 positive nuclei quantified from immunohistochemistry sections of primagraft tumors at the conclusion of the xenotransplantation trial in FIG. 17B (n=3 images quantified, >200 nuclei each). ATRA treatment had no significant effect on proliferation.
FIG. 17G shows composite enrichment profile for MYB bound regions (n=1,868) in ACC x9 vehicle and ATRA treated samples. MYB binding is reduced overall genome-wide in response to ATRA.
FIG. 17H shows MYB and RAR binding and H3K27ac profiles downstream of NFIB exon 9 or the MYB locus in ACC x9 tumors (negative strand shown). Previously described translocated MYB-bound enhancers that loop to the MYB promoter are labeled. *p<0.05; p<0.01; *p<0.001, by unpaired one-tailed t-test, mean with s.e.m.

The in vivo efficacy of ATRA and isotretinoin in ACC xenotransplantation trials was assessed (FIG. 17A). Evidence suggests that patient derived xenografts (PDXs) serve as the most reliable preclinical model available by preserving tumor structure and heterogeneity and facilitating clinical predictions of drug responses in vivo. PDX studies are particularly important in ACC given that there are currently no validated ACC cell lines that can be cultured. Most ACC tumors are low grade (grade 1 and 2, with 'tubular' and 'cribriform' patterns respectively) and are histologically dominated by myoepithelial cells, whereas a small number of tumors have predominantly luminal epithelial cells and are more aggressive (grade 3, with 'solid' pattern). For long-term tumor growth inhibition studies, nude mice were engrafted with three different human ACC tumors: x6 (grade 2 primagrafts), and x9 and x11 (grade 3 primagrafts). These PDX models were isolated from different patients, confirmed to have MYB translocations, and shown to recapitulate the parent tumors by histology and gene expression.

Figures 21A, 21B, 21C:
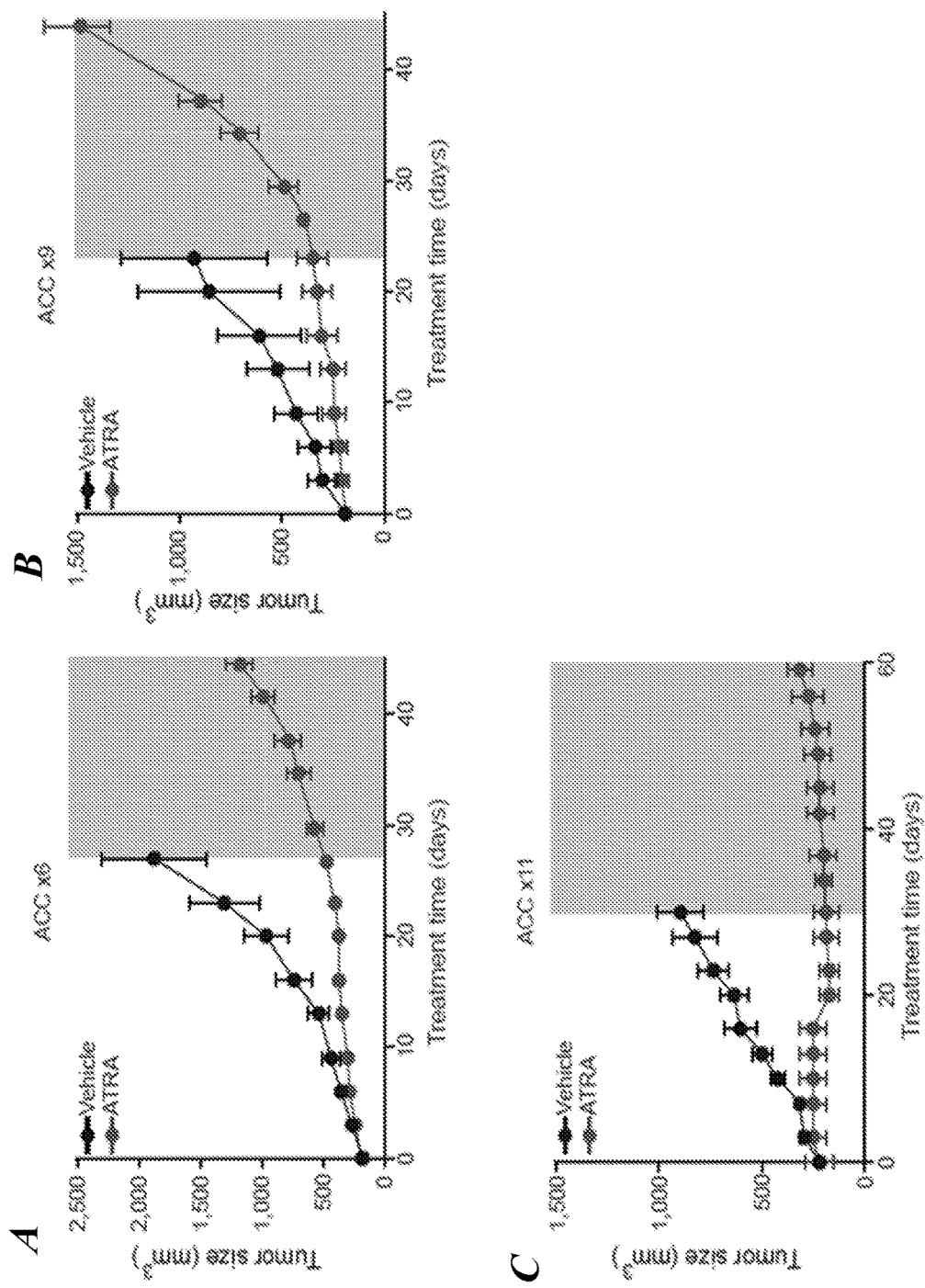
FIGS. 21A-21C are line graphs showing tumor maintenance after discontinuation of in ACC primagrafts—ACCx6 (FIG. 21A), ACCx9 (FIG. 21B) and ACCx11 (FIG. 21C). Tumor burden was monitored in ATRA treated mice groups after treatment stopped. Tumor growth inhibition was sustained in ACC x11 (FIG. 21C), but not in ACC x6 (FIG. 21A) and ACC x9 (FIG. 21B). ATRA was discontinued during the time represented by the colored area. Mean with s.e.m.

Randomized groups of mice were treated with vehicle, ATRA, or isotretinoin, and tumor size was measured over time (FIG. 17B). Retinoic acid treatment inhibited tumor growth significantly (FIG. 17C). After long-term tumor growth studies were completed in approximately 28 days, ATRA treatment was discontinued and tumor size was continued to measure in the ATRA treated mice groups over an extended period of time to monitor tumor maintenance post-treatment (FIGS. 21A-21C Tumor growth inhibition was sustained in ACC x11 (FIG. 21C), but not in ACC x6 (FIG. 21A) and ACC x9 (FIG. 21B), suggesting that continuous treatment may be needed to target residual tumor cells.

Figure 22B:
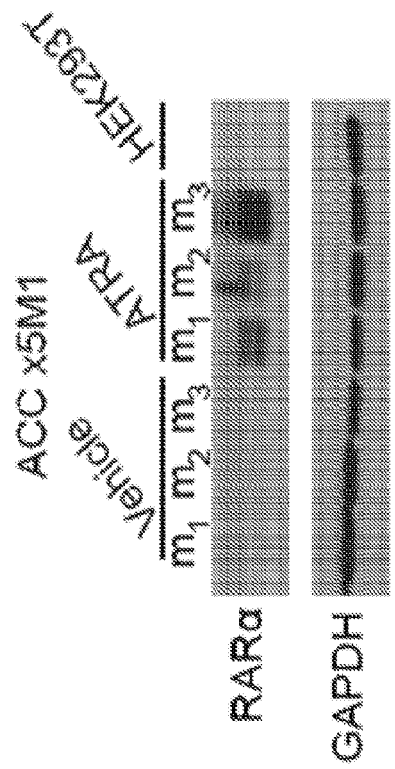
FIGS. 22A and 22B show protein expression of MYB (FIG. 22A) and RARα (FIG. 22B) in individual ACC x5M1 primagrafts after 3 days of ATRA treatment (3 primagrafts from different mice shown for each treatment group). HEK293T cell lysate is a negative control lacking MYB expression. ATRA decreases MYB levels in ACC primagrafts.
Figure 22A:
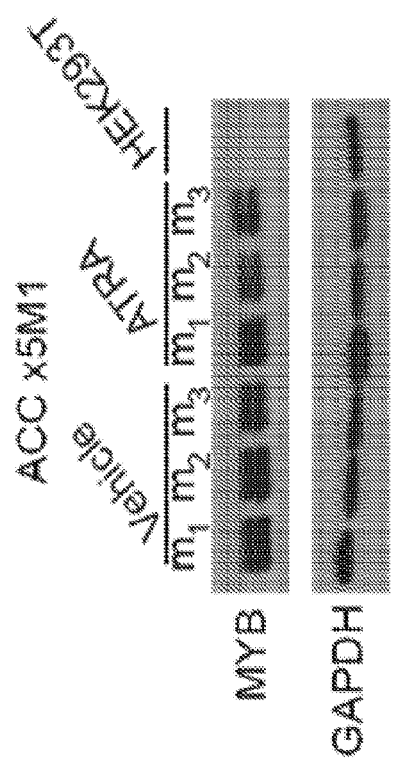

Xenotransplantation studies were performed with ACC x9 and x5M1 (grade 2 primagraft) consisting of three day treatment with vehicle or ATRA to examine short-term kinetic responses. A decrease in MYB protein expression was determined by Western blot analysis, both for the wildtype and fusion proteins in ATRA treated long-term ACC x11 and short-term ACC x5M1 primagrafts (FIGS. 17D, 22A and 22B). RARα protein expression increased in the ATRA treated samples, indicating that the tumors responded to ATRA treatment.

Figure 23:
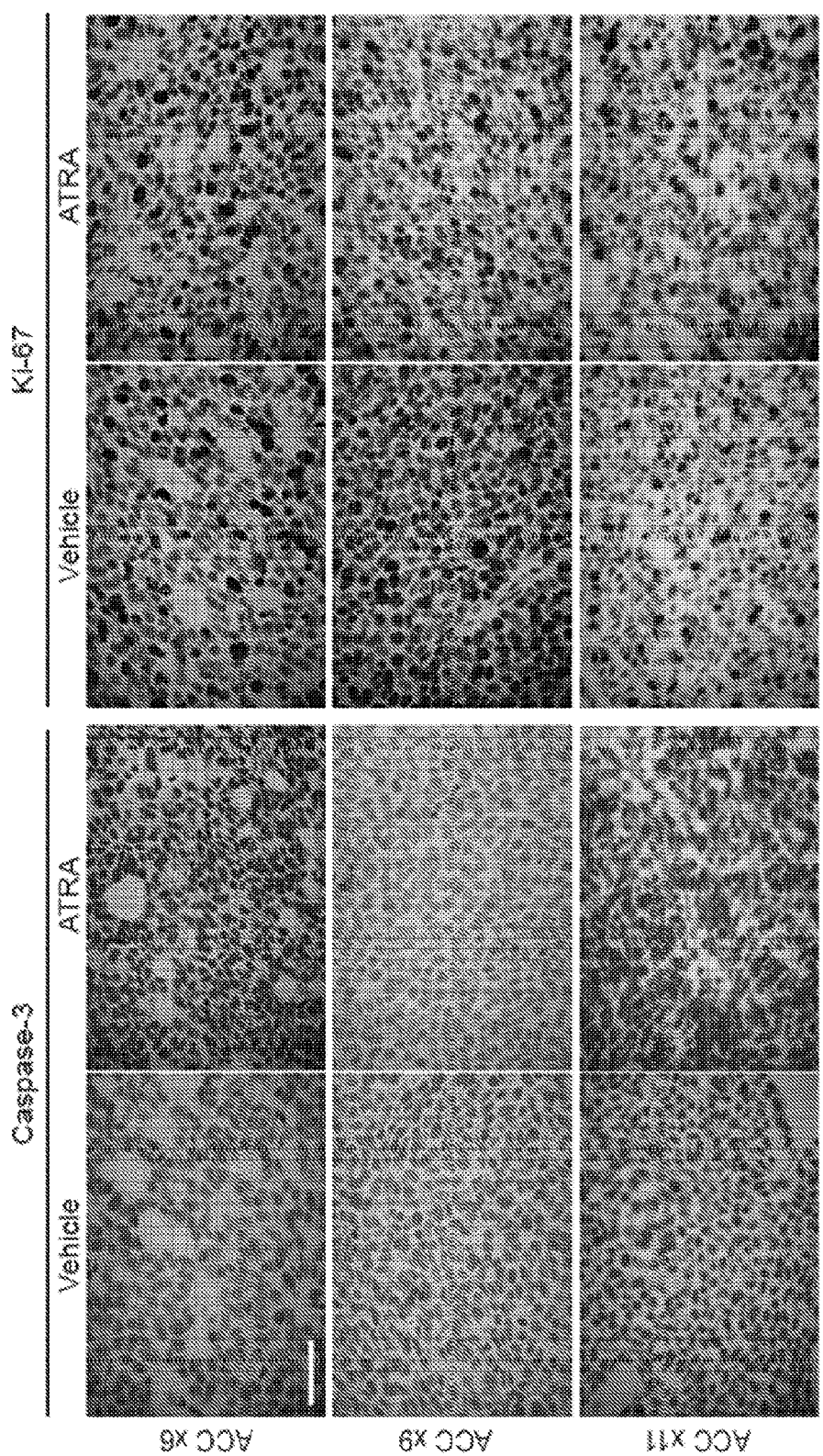
FIG. 23 shows representative images of immunohistochemistry sections for cleaved caspase-3 and Ki-67 in three primagrafts. Scale bar, 40 μm. ATRA induces cell death in ACC.
Figures 24A, 24B, 24C:
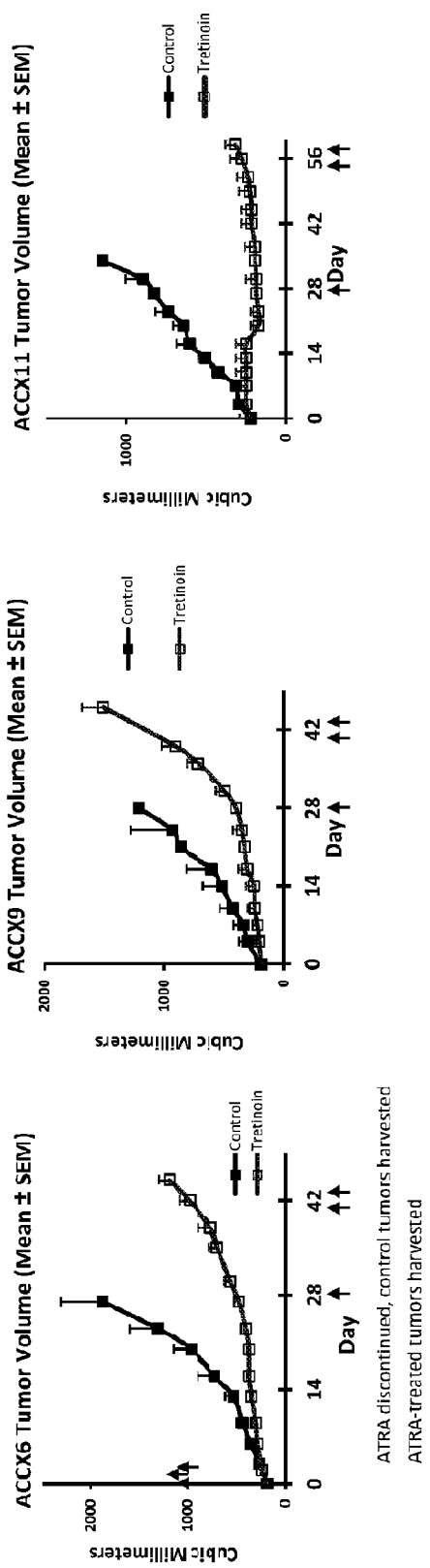
FIGS. 24A-24C are line graphs showing ATRA-induced inhibition of tumor growth in ACC PDX models—ACCx6 (FIG. 24A), ACCx9 (FIG. 24B) and ACCx11 (FIG. 24C).
Figure 24D:
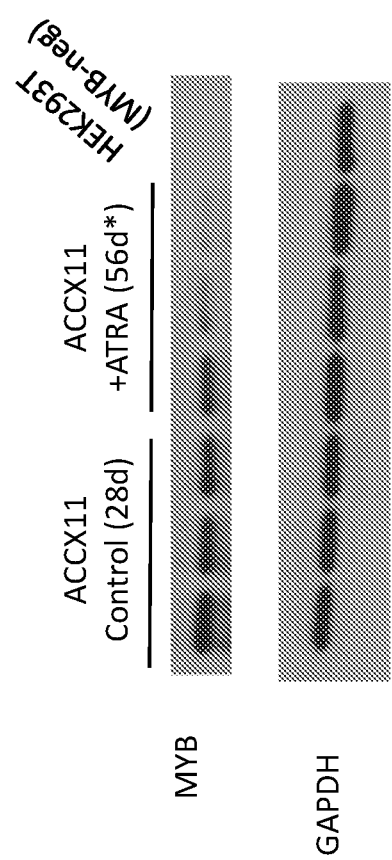
FIG. 24D shows ATRA-induced suppression of myb in ACC PDX models.
Figure 24E:
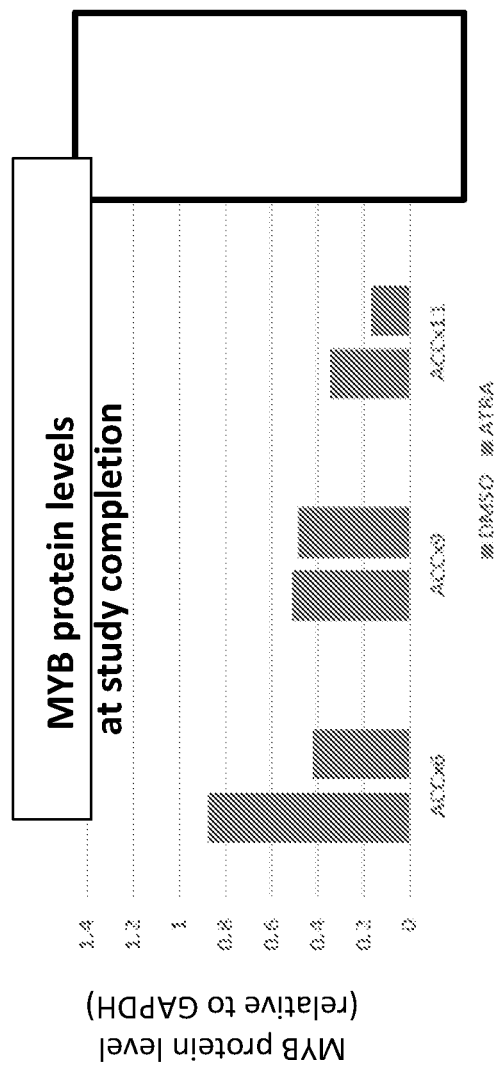
FIG. 24E is a bar graph showing MYB protein levels at completion of the study.
Figure 25A:
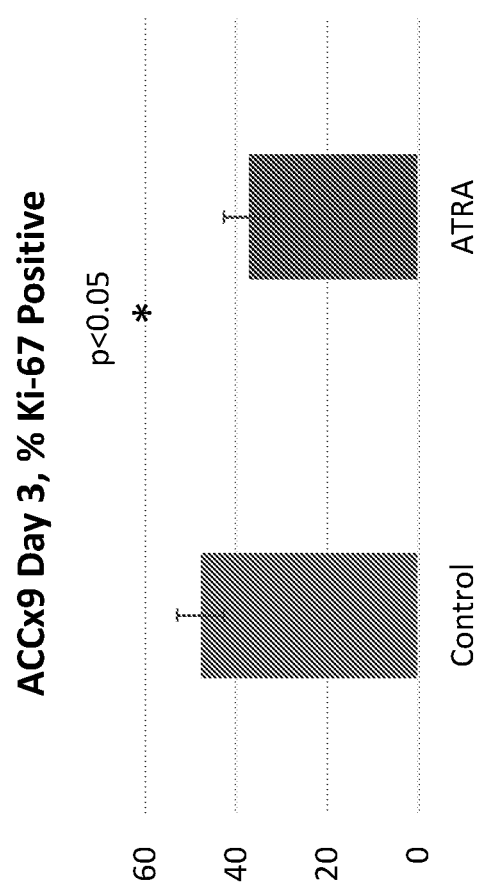
FIGS. 25A and 25B are graphs showing changes in proliferation and myb levels in short-term ATRA in vivo dosing studies.
Figure 25B:
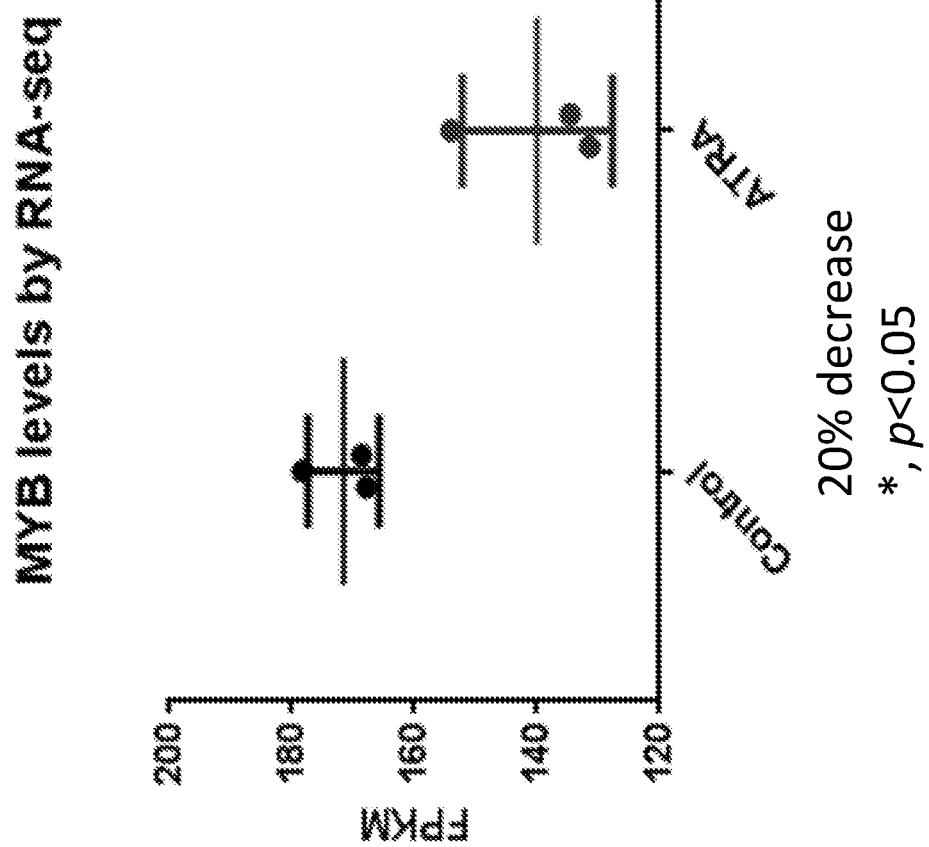
Figure 26:
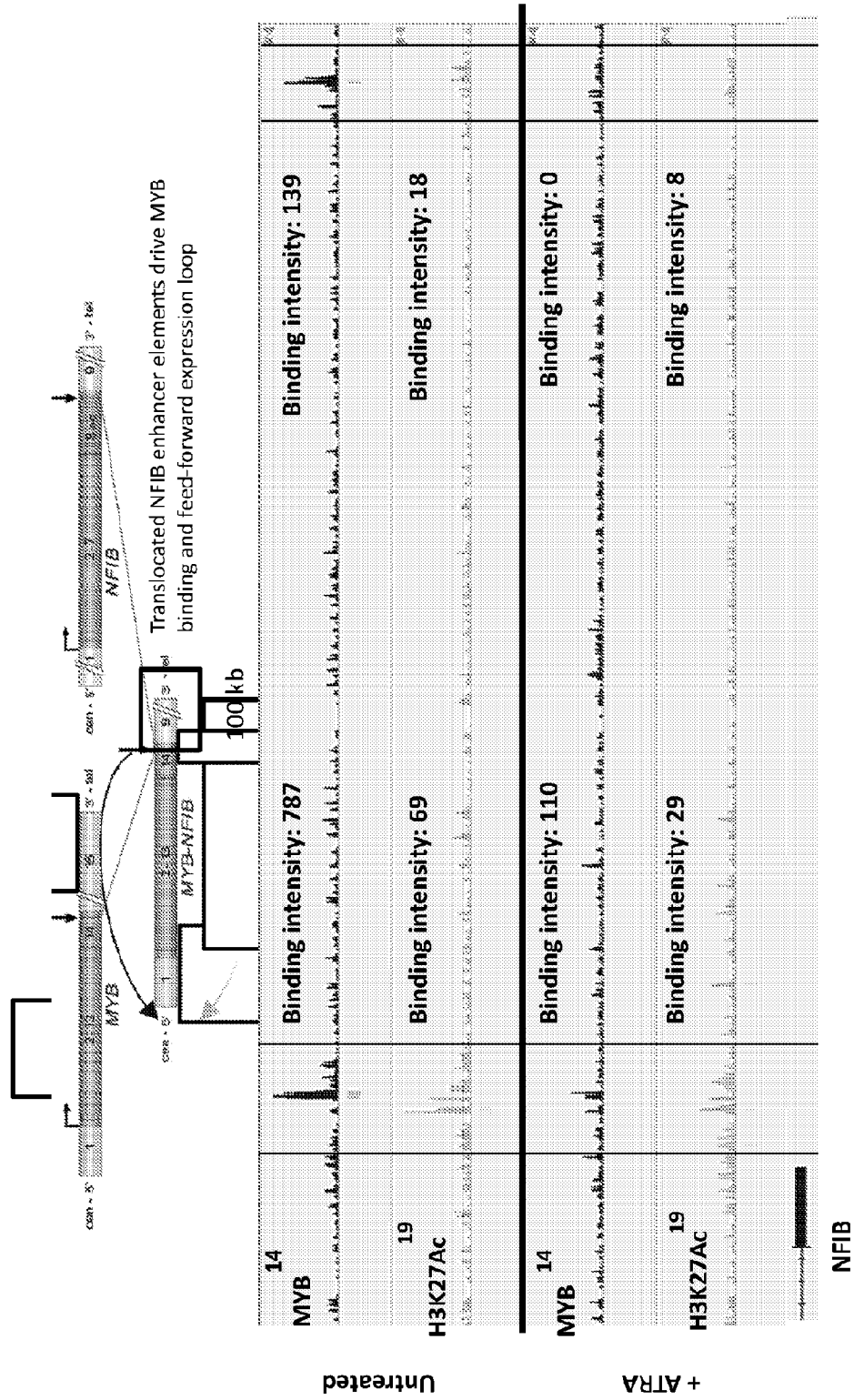
FIG. 26 shows ATRA's proposed mechanism of action at translocated enhancers at myb locus.
Figure 27:
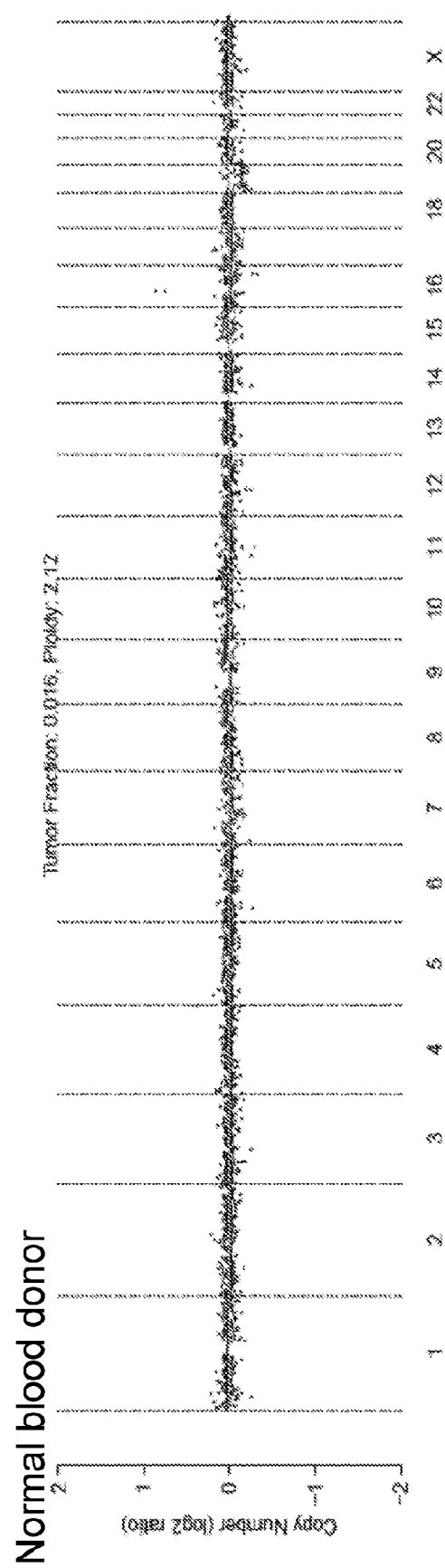
FIG. 27 shows whole genome sequencing of cell-free DNA from blood of normal blood donor.
Figure 28C:
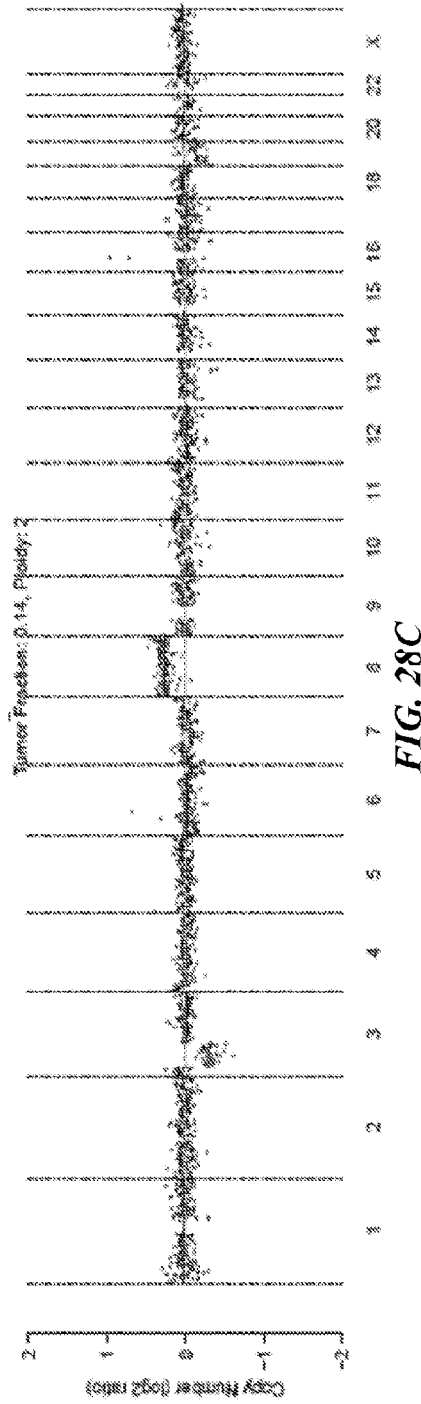
Figure 28D:
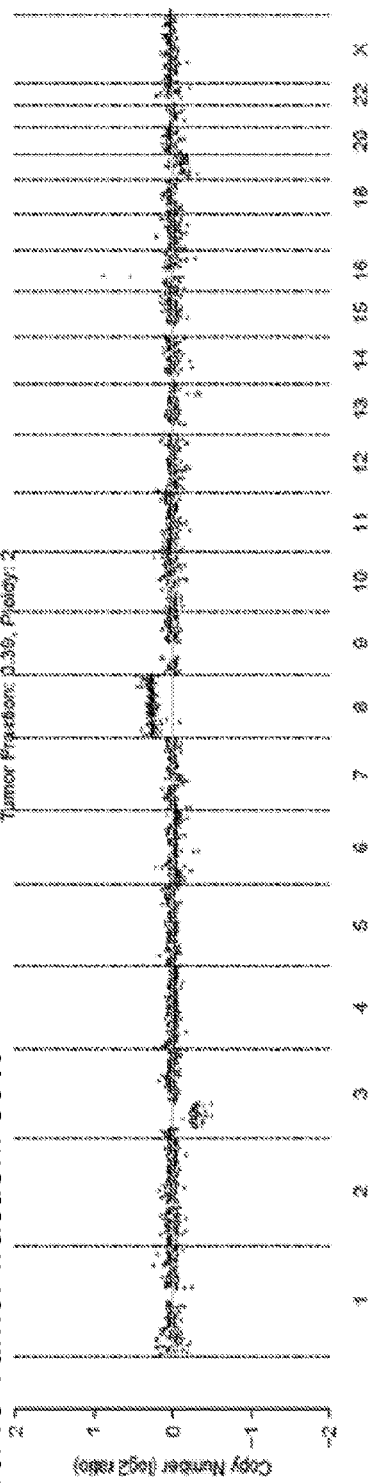
Figure 29:
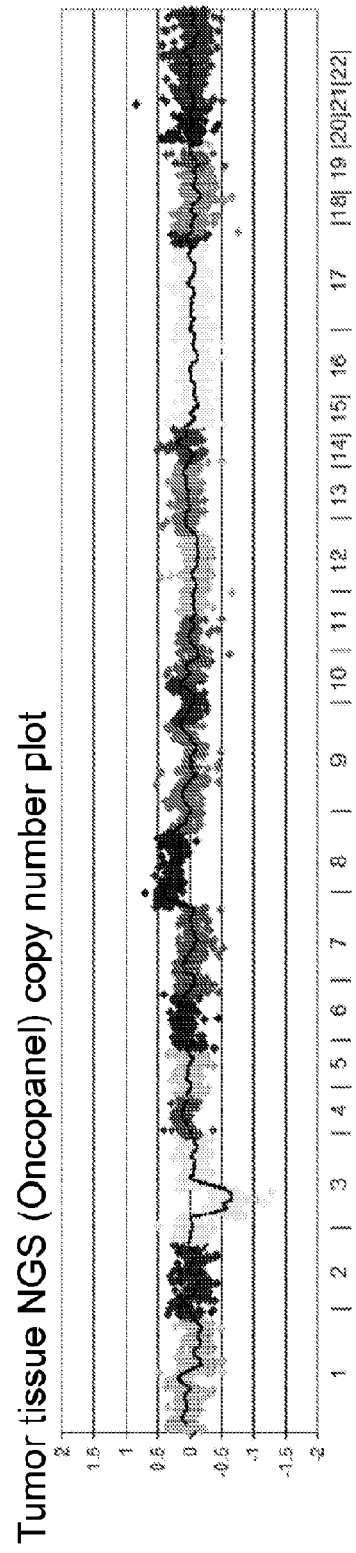
FIG. 29 shows whole genome sequencing of cell-free DNA from ACC patient compared to tumor tissue sequencing. As seen, the arm level copy number detection is highly reproducible and robust across multiple time points in ACC.
Figure 30:
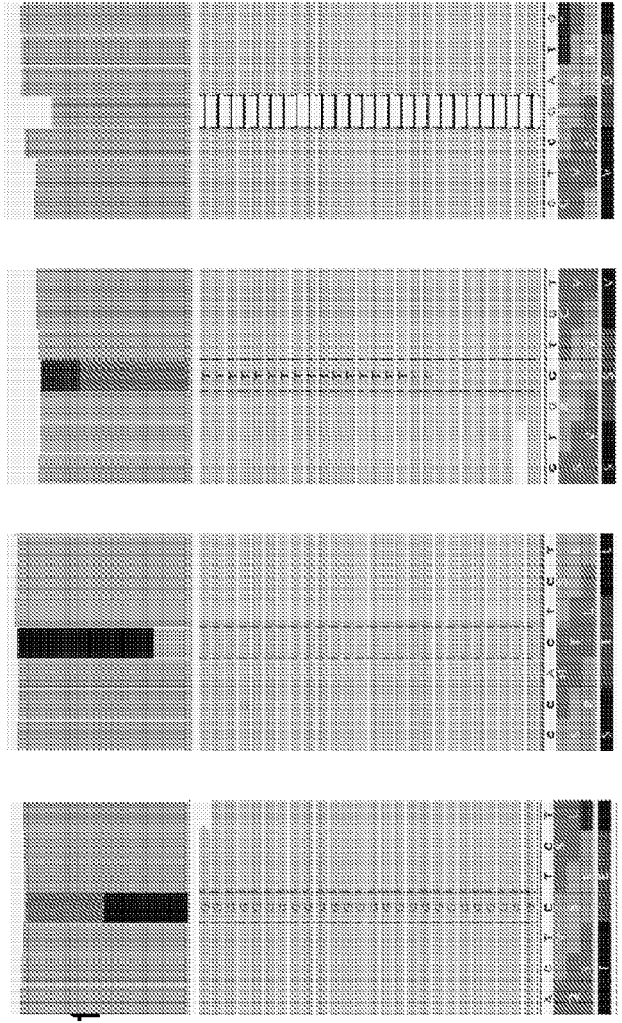
FIG. 30 shows whole exome sequencing of cell-free DNA from ACC patient compared to tumor tissue sequencing. This compares the mutations that were called in OncoPanel and the same loci for which mutations were called in whole exome sequencing from circulating cell-free DNA (cfDNA). These findings support that it is feasible to evaluate ctDNA as a biomarker of disease activity in ACC and response to therapy. The ATRX and CIITA mutations are germline, and CREBBP and EP300 are somatic.

Apoptosis was examined by caspase-3 and proliferation by Ki-67 markers with immunohistochemistry in the ACC x6, x9, and x11 primagrafts at the conclusion of the long-term studies (FIGS. 17E, 17F and 23). At the time points examined, ATRA treatment appeared to cause more cell death, which could account for the marked tumor growth inhibition that was observed during the xenotransplantation trial, but had no significant effect on proliferation.

Translocations involving MYB have been previously described in ACC for bringing strong enhancers into close proximity of the MYB locus, and these enhancers are also bound by MYB protein, resulting in a positive feedback loop that drives MYB overexpression. MYB protein binding in short-term ACC x9 primagrafts were mapped by ChIP-seq and a reduced enrichment among MYB-bound regions genome-wide was discovered due to ATRA treatment (FIG. 17G). A strong decrease in binding was specifically observed due to ATRA treatment in the downstream region of NFIB that is translocated to MYB in ACC x9 (FIG. 17H). There was a concomitant decrease in H3K27ac (marking active enhancers) at these sites. RAR was found to bind physically at the MYB locus. Although it cannot be specifically concluded which RAR subtype is bound at this locus ($\alpha$, $\beta$, or $\gamma$), it was determined by RNA-seq that RARA and RARG gene levels significantly increased ~40% in short-term ACC x9 primagrafts and MYB levels decreased ~20% due to ATRA treatment (n=3, p<0.05). The studies establish that ATRA acts via RAR to directly suppress MYB expression.

Discussion

ACC is a fatal disease without an effective therapy. Translocated enhancers from MYB chromosomal rearrangements in ACC generate positive feedback loops that lead to MYB overexpression and malignant transformation. Here, it is found that retinoic acid causes a reduction in c-myb levels in zebrafish and ACC tumors. Retinoic acid agonists are potent transcriptional suppressors of MYB as RAR is physically bound at the MYB locus. Retinoic acid treatment causes a decrease of H3K27ac and MYB binding at the translocated enhancers, thereby disrupting the oncogenic MYB-driven feedback loops. The effect of this loop disruption is to cause tumor death.

The function studies on the effect of retinoic acid on MYB expression in ACC, taken together with the clinical availability of ATRA and known toxicity profile, provide a strong rationale to treat ACC with ATRA. Acute promyelocytic leukemia due to a translocation resulting in PML-RARA fusion can be treated with an ATRA split dose of 45 mg/m2 daily. ATRA treatment is often combined in these patients with anthracycline chemotherapy or, in low-risk patients (white blood cell count <10,000/µL and platelet count >40,000/µL), with arsenic trioxide. The aberrant protein containing a RARα fusion is sensitive to ATRA and is consequently degraded. Although the mechanism of action of ATRA in acute promyelocytic leukemia is distinct from the MYB transcriptional inhibition as proposed in ACC, the known safety profile of ATRA may guide its use in ACC.

Unlike ACC x9 and x11 tumors, ACC x6 tumors are sensitive to bromodomain inhibitors. ACC x9 tumors are NOTCH dependent and show sensitivity to gamma-secretase inhibitors. In contrast, tumor sensitivity to retinoic acids was observed across ACC x6 (involving MYB-TGFBR3 translocations), and x9 and x11 (both involving MYB-NFIB translocations) primagrafts, which shows that this strategy of targeting MYB can be applied effectively against different ACC mutations in grade 2 and 3 tumors. Furthermore, levels of tumor growth inhibition achieved with retinoic acids surpassed those reported with bromodomain and NOTCH inhibitors. Given the near universal prevalence of MYB activation in ACC tumors, the exploitation of MYB targeting has the potential to offer unprecedented broad therapeutic efficacy compared to other targeted therapies studied to date. Whether ATRA (or other retinoic acid agonists) should serve as a single agent or in combination in ACC therapy remains a subject for future studies.

In this study, a zebrafish chemical genetic screening approach was used that revealed retinoic acid agonists as downregulators of c-myb. The high-throughput screening platform leverages the benefits of zebrafish, including the high fecundity of adults to collect thousands of embryos each week for chemical screening, and the high degree of genetic conservation with mammals for the reliable translation of chemical hits. Thousands of compounds were screened in an automated manner at a fraction of the time that would be needed to analyze whole embryo readouts as in an in situ hybridization based screen. Retinoic acids identified in the zebrafish embryo cell culture strategy showed strong ACC tumor growth inhibition in xenotransplantation models by targeting MYB, which highlights the power of the zebrafish system as a preclinical discovery tool. This study illustrates that disrupting the common core MYB circuitry in ACC with retinoic acid agonists offers a new potential therapy targeting the underlying cause of the disease.

Methods

Culture of dissociated blastomere cells: Stage-matched zebrafish blastomeres were dissociated at 4 hpf and grown in medium composed of 85% LDF medium, 5% FBS, and 10% embryo extract. LDF medium contains 50% Leibowitz's L-15 (Invitrogen), 20% DMEM (Invitrogen), and 30% DMEM/F-12 (Invitrogen), supplemented with 2% B27 (Gibco), 15 mM HEPES (Gibco), 1% L-glutamine (Gibco), 1% N2 (Gibco), 10 nM sodium selenite (Sigma), 100 ug/mL piperacillin (Sigma), 10 ug/mL ciprofloxacin (GenHunter), and 0.018% sodium bicarbonate (Gibco). Embryo extract was made by homogenizing 24 hpf wildtype AB embryos in HBSS (Gibco). All zebrafish experiments and procedures were performed as per protocols approved by the Boston Children's Hospital IACUC and the Harvard University IACUC.

High-throughput screen: To screen each chemical library plate in duplicate, two 384-well plates were coated with 0.1% gelatin. C-myb:GFP embryos were washed with E3 embryo water and dechorionated with pronase. Embryos were washed with E3 embryo water, resuspended in blastomere media, inverted ~15 times to dissociate, and filtered through a 40 µm nylon mesh filter. Single cells obtained were aliquoted 40 µl per well at approximately 2 embryo equivalents per well, and immediately screened with chemicals from NIH (Evotec, 720), Library of Pharmacologically Active Compounds (Sigma, 1,440), ICCB Known Bioactives (Biomol, 480), and Nuclear Hormone Receptor and Kinacore (ChemBridge, 1,200) libraries at 30 µM. Cells were cultured in a 28° C. incubator with 5% CO2 for 2 days. Cells were stained with draq5 (Cell Signaling Technology) and imaged using a Cell Voyager 7000 (Yokogawa).

A 4× image of the nuclear and fluorescent expression from the entire well was then thresholded and percent area was computed using ImageJ/Fiji. Control wells (200 or more per plate) were identified using quartile exclusion of outliers, and using these wells, a standard curve was built with GFP vs. nuclear staining in MatLab. From that standard curve, residuals were calculated for each treated well and divided by the standard deviation in the control wells to obtain the z-score of each chemical treatment.

Dose response studies using c-myb:GFP embryo cultures and follow-up experiments were performed with retinoic acid agonists dissolved in DMSO: AM580 (Tocris), 9-cis retinoic acid (Sigma), retinoic acid p-hydroxyanilide (Sigma), TTNPB (Tocris), AC261066 (Tocris), and ATRA (Sigma).

Confocal imaging: Double transgenic c-myb:GFP; lyz: dsRed or c-myb:GFP; mpeg1:mCherry embryos from the same clutch were treated between 48-72 hpf (n=4 biological replicates per treatment group) with 10 μM ATRA diluted in E3. Live 72 hpf embryos were embedded in 0.8% low-melting point agarose containing 0.04 mg/mL Tricaine and imaged on a Nikon Eclipe Ti microscope with 20× Plan-Apo DIC N.A. 0.75. CHT cells were counted in Z-stack image projections processed on Imaris software (Bitplane). The c-myb:GFP cell counts were combined across the two sets and displayed in the graph.

In situ hybridization: Wildtype AB embryos from the same clutch were treated between 48-72 hpf with 10 μM retinoic acid agonists diluted in E3, fixed at 72 hpf in 4% paraformaldehyde, and processed as previously described. CHT staining in the embryos was blindly scored as high, medium, or low, and summed across 3 independent experiments as done previously. Representative images were acquired on a Nikon ZMS 18 microscope.

Proliferation assays: U937 cells (ATCC) were grown in RPMI 1640 medium (Gibco) supplemented with 10% FBS and 1% Penicillin-Streptomycin (Gibco) and cultured in a 37° C. incubator with 5% CO2. U937 cells are listed in the database of commonly misidentified cell lines maintained by ICLAC, but authentic stocks are available and certified by ATCC based on DNA short-tandem repeat analysis. Hence, U937 cells were suitable for our studies since these cells have been authenticated, are a commonly studied hematopoietic cell line, and express high levels of c-myb. U937 cells were tested every other week for *mycoplasma* contamination using the MycoAlert *Mycoplasma* Detection Kit (Lonza) and consistently confirmed to be negative. Cells were seeded at an initial density of 1,150 cells/well (96 well plate) with chemicals at the concentrations indicated. After 48 hours, cell proliferation rates were determined using CellTiter-Glo (Promega) luminescent cell viability assay as per the manufacturer's instructions.

Zebrafish quantitative PCR analysis: Stage-matched 72 hpf c-myb:GFP transgenic embryos were finely chopped and dissociated using Liberase (Roche). GFP+ cells were collected using a FACS Aria cell sorter (BD Biosciences). Sorted cells were resuspended in zebrafish blastomere media and plated with 1 μM retinoic acid agonists for 6 hours. Cells were then collected and RNA was isolated using the RNeasy Micro Plus Kit (Qiagen) as per the manufacturer's instructions. cDNA was synthesized using the SuperScript III Kit (Life Technologies). Quantitative PCR was performed in triplicate on a BioRad iQ5 real-time PCR machine using Ssofast EvaGreen Supermix (BioRad). Samples were normalized to β-actin gene. Zebrafish primers used (forward and reverse respectively): actin, 5'-CGAGCAGGA-GATGGGAACC-3' (SEQ ID No:3) and 5'-CAACG-GAAACGCTCATTGC -3' (SEQ ID No:4); c-myb, 5'-TGATGCTTCCCAACACAGAG-3' (SEQ ID No:1) and 5'-TTCAGAGGGAATCGTCTGCT-3' (SEQ ID No:2); mpx, 5'-GCTGCTGTTGTGCTCTTTCA-3' (SEQ ID No:11) and 5'-TTGAGTGAGCAGGTTTGTGG-3' (SEQ ID No:12); GFP, 5'-AAGCTGACCCTGAAGTTCATCTGC-3' (SEQ ID No:13) and 5'-CTTGTAGTTGCCGTCGTCCTT-GAA-3' (SEQ ID No:14).

U937 time course quantitative PCR analysis: U937 cells were plated with 1 μM retinoic acid agonists for the duration indicated. Cells were then collected and RNA was isolated using the RNeasy Plus Mini Kit (Qiagen) as per the manufacturer's instructions. Further processing was done as described in the section above. Samples were normalized to β-actin gene. Human primers used (forward and reverse respectively): actin, 5'-AGTGGGGTGGCTTTTAGGAT-3' (SEQ ID No:9) and 5'-CCGAGGACTTTGATTGCACA-3' (SEQ ID No:10); c-myb, 5'-GGCAGAAATCGCAAAGC-TAC-3' (SEQ ID No:5) and 5'-ACCTTCCTGTTCGACCT-TCC-3' (SEQ ID No:6).

Primagraft experiments: For in vivo drug testing, ACC tumor fragments from host animals were implanted subcutaneously into the flank of nude mice (CRL: ATH/NU). Once tumors reached 125-250 mm3, mice were randomized to receive vehicle or drug diluted in 10:90 DMSO:10% hydroxypropyl-beta-cyclodextrin orally until controls reached a tumor volume endpoint of 1-2 cm3 (4-9 mice per group: x5M1 and x6, 4 treated vs. 9 vehicle controls; x9, 4 treated vs. 5 vehicle controls; x11, 5 treated vs. 8 vehicle controls). Mice were treated with ATRA (ACC x6 and x11: 4 mg/mL, 0.2 mL flat dose; ACC×9: 3 mg/mL, 0.2 mL flat dose) or isotretinoin (30 mg/mL, 0.2 mL flat dose). Tumor growth was monitored and mice weighed twice weekly and studies ended when final group reached tumor volume endpoint. No statistical methods were employed to determine the sample size, and no blinding of investigators was performed. After long-term tumor growth inhibition studies were completed, the ATRA treated mice stopped receiving treatment and were maintained longer as indicated to monitor tumor maintenance after treatment cessation. For long-term tumor growth inhibition studies, ACC x6, x9, and x11 models were used and primagrafts collected at the completion of the study. Short-term kinetics studies were also undertaken with ACC x9 and x5M1 primagrafts involving 3 day ATRA treatments. All animal procedures used in this study were approved by the IACUC at START, San Antonio, Tex.

Western blots: ACC x11 (from long-term tumor growth inhibition studies) and ACC x5M1 (from short-term kinetics studies) primagrafts were mechanically homogenized in RIPA lysis buffer (Thermo Scientific) supplemented by addition of complete protease inhibitor cocktail (Roche). Protein concentrations were determined by DC protein assay (BioRad). Samples were denatured by adding Laemmli sample buffer (BioRad) with β-mercaptoethanol (Sigma) and boiled at 95° C. for 5 minutes. 10 μg of protein was resolved by electrophoresis through 4-20% mini-PROTEAN TGX (BioRad) precast gels. Proteins were transferred onto a nitrocellulose membrane using the iBlot dry blotting system (Invitrogen). Membranes were incubated overnight with primary antibodies: anti-Myb (Abcam, ab45150), anti-RARa (Chemicon, MAB5346), and anti-GAPDH (Cell Signaling Technology, 2118s) as loading control. Protein bands were detected using horse anti-mouse HRP (Cell Signaling Technology, 7076S) or goat anti-rabbit HRP (Cell Signaling Technology, 7074S). 3 biological replicates (individual primagrafts from different mice) for each treatment group were analyzed for protein expression. HEK293T cell lysate, which lacks MYB expression, was processed similarly and used as a negative control on the same blots.

Immunohistochemistry: Sectioning and staining was carried out by the Dana-Farber/Harvard Cancer Center Specialized Histopathology Core using standard procedures on ACC x6, x9, and x11 samples (from long-term tumor growth inhibition studies). Slides were baked for 60 minutes in an oven set to 60° C. and loaded into the Bond III staining platform with appropriate labels. Slides were either antigen retrieved in Bond Epitope Retrieval 2 for 20 minutes and incubated with Ki-67 (SP6) (Biocare, CRM325) at 1:200 for 30 minutes at room temperature, or antigen retrieved in Bond Epitope Retrieval 1 for 30 minutes and incubated with cleaved caspase-3 (5A1E) (Cell Signaling Technologies, 9664) at 1:150 for 30 minutes at room temperature. Primary antibody was detected using Bond Polymer Refine Detection kit. Slides were developed in DAB, dehydrated, and coverslipped. Transmitted light images were acquired on a Nikon Eclipse E600 microscope at 40×. Images (>200 nuclei each) from three different individual primagrafts were blindly quantitated.

RNA-sequencing and bioinformatics: RNA-seq was performed on 3 biological replicates of ACC x9 primagrafts (from short-term kinetics studies) treated with vehicle or ATRA for 3 days (individual primagrafts from different mice). Frozen primagrafts were lysed and RNA was isolated using the RNeasy Mini Plus Kit (Qiagen) as per the manufacturer's instructions. Ribosomal RNA was then depleted using the Ribo-Zero Gold Kit (Epicentre) as per the manufacturer's instructions. Sequencing libraries were constructed from ribosome-depleted RNA samples using the NEBNext Ultra Kit (New England Biolabs) and sequenced on a Hi-Seq 2500 instrument (Illumina).

Quality control of RNA-Seq datasets was performed by FastQC and Cutadapt to remove adaptor sequences and low quality regions. The high-quality reads were aligned to UCSC build hg19 of human genome using Tophat 2.0.11 without novel splicing form calls. Transcript abundance and differential expression were calculated with Cufflinks 2.2.1. FPKM values were used to normalize and quantify each transcript; the resulting list of differential expressed genes are filtered by log fold change >2 and q-value <0.05. Data sets are deposited in GEO Gene Expression Omnibus, accession number GSE98008 (https://www.ncbi.nlm.nih.gov/geo/query/acc.cgi?token=adqtysicxlulvgt&acc=GSE98008).

ChIP-sequencing and bioinformatics: ChIP-seq was performed on ACC x9 primagrafts (from short-term kinetics studies) treated with vehicle or ATRA for 3 days. Frozen primagrafts were mechanically dissociated, formaldehyde cross-linked, and collected. ChIP was performed as described previously with 10 µg antibodies against c-myb (Bethyl, A304-136A), pan-RAR (Santa Cruz, sc-773X)41, and H3K27ac (Abcam, ab4729). Sequencing libraries were constructed using the NEBNext Multiplex Oligos Kit (New England Biolabs) and sequenced on a Hi-Seq 2500 instrument (Illumina).

All ChIP-Seq datasets were aligned to UCSC build version hg19 of the human genome using Bowtie2 (version 2.2.1) with the following parameters: -end-to-end, —NO, -L20. MACS2 version 2.1.0 peak finding algorithm was used to identify regions of ChIP-Seq peaks, with a 0.05 q-value threshold of enrichment for all datasets. ChIP-seq enrichment was determined as described previously in a 5 kb region (as counts per million) centered on the enriched peak regions (n=1,868) of the given MYB datasets. Data sets are deposited in GEO Gene Expression Omnibus, accession number GSE98008, which can be accessed on the web at (www.ncbi.nlm.nih.gov/geo/query/acc.cgi?token=adqtysicxlulvgt&acc=GSE98008).

Statistics: As previously described, in situ hybridization experiments were analyzed by Chi-square or one-tailed Fisher's Exact Test if sample sizes were small. All other p-values were determined by unpaired one-tailed t-test by comparing treated samples to untreated controls. Significance of dose response curves and proliferation assays was determined at 1 µM concentration. Significance of ATRA or isotretinoin treatment in the long-term primagraft experiments was determined by comparing the change in tumor growth in the control and treated groups. Statistics were performed using GraphPad Prism software. Graphs show means with s.e.m. as indicated.

References

1 Coca-Pelaz, A. et al. Adenoid cystic carcinoma of the head and neck—An update. *Oral oncology* 51, 652-661, doi: 10.1016/j.oraloncology.2015.04.005 (2015).

2 Persson, M. et al. Recurrent fusion of MYB and NFIB transcription factor genes in carcinomas of the breast and head and neck. *Proc Natl Acad Sci USA* 106, 18740-18744, doi:10.1073/pnas.0909114106 (2009).

3 Mitani, Y. et al. Novel MYBL1 Gene Rearrangements with Recurrent MYBL1-NFIB Fusions in Salivary Adenoid Cystic Carcinomas Lacking t(6; 9) Translocations. *Clinical cancer research: an official journal of the American Association for Cancer Research* 22, 725-733, doi: 10.1158/1078-0432.CCR-15-2867-T (2016).

4 Ho, A. S. et al. The mutational landscape of adenoid cystic carcinoma. *Nat Genet* 45, 791-798, doi:10.1038/ng.2643 (2013).

5 Oh, I. H. & Reddy, E. P. The myb gene family in cell growth, differentiation and apoptosis. *Oncogene* 18, 3017-3033, doi: 10.1038/sj.onc. 1202839 (1999).

6 Ramsay, R. G. & Gonda, T. J. MYB function in normal and cancer cells. *Nat Rev Cancer* 8, 523-534, doi:10.1038/nrc2439 (2008).

7 Mikse, O. R. et al. The impact of the MYB-NFIB fusion proto-oncogene in vivo. *Oncotarget* 7, 31681-31688, doi: 10.18632/oncotarget.9426 (2016).

8 Bradley, P. J. Adenoid cystic carcinoma of the head and neck: a review. *Current opinion in otolaryngology & head and neck surgery* 12, 127-132 (2004).

9 Conley, J. & Dingman, D. L. Adenoid cystic carcinoma in the head and neck (cylindroma). *Archives of otolaryngology* 100, 81-90 (1974).

10 Spiro, R. H. Distant metastasis in adenoid cystic carcinoma of salivary origin. *American journal of surgery* 174, 495-498 (1997).

11 Bobbio, A. et al. Lung metastasis resection of adenoid cystic carcinoma of salivary glands. *European journal of cardio-thoracic surgery: official journal of the European Association for Cardio-thoracic Surgery* 33, 790-793, doi:10.1016/j.ejcts.2007.12.057 (2008).

12 Hickman, R. E., Cawson, R. A. & Duffy, S. W. The prognosis of specific types of salivary gland tumors. *Cancer* 54, 1620-1624 (1984).

13 Stephens, P. J. et al. Whole exome sequencing of adenoid cystic carcinoma. *J Clin Invest* 123, 2965-2968, doi: 10.1172/JCI67201 (2013).

14 Ross, J. S. et al. Comprehensive genomic profiling of relapsed and metastatic adenoid cystic carcinomas by next-generation sequencing reveals potential new routes to targeted therapies. *The American journal of surgical pathology* 38, 235-238, doi:10.1097/PAS.0000000000000102 (2014).

15 Yarbrough, W. G., Panaccione, A., Chang, M. T. & Ivanov, S. V. Clinical and molecular insights into adenoid cystic carcinoma: Neural crest-like stemness as a target. *Laryngoscope Investigative Otolaryngology* 1, 60-77, doi: 10.1002/lio2.22 (2016).

16 Ferrarotto, R. et al. Activating NOTCH1 Mutations Define a Distinct Subgroup of Patients With Adenoid Cystic Carcinoma Who Have Poor Prognosis, Propensity to Bone and Liver Metastasis, and Potential Responsiveness to Notch1 Inhibitors. *J Clin Oncol* 35, 352-360, doi:10.1200/JCO.2016.67.5264 (2017).

17 Xu, C. et al. A zebrafish embryo culture system defines factors that promote vertebrate myogenesis across species. *Cell* 155, 909-921, doi:10.1016/j.cell.2013.10.023 (2013).

18 North, T. E. et al. Prostaglandin E2 regulates vertebrate haematopoietic stem cell homeostasis. *Nature* 447, 1007-1011, doi:10.1038/nature05883 (2007).

19 Orkin, S. H. & Zon, L. I. Hematopoiesis: an evolving paradigm for stem cell biology. *Cell* 132, 631-644, doi: 10.1016/j.cell.2008.01.025 (2008).

20 Graf, T. Myb: a transcriptional activator linking proliferation and differentiation in hematopoietic cells. *Curr Opin Genet Dev* 2, 249-255 (1992).

21 Cunningham, T. J. & Duester, G. Mechanisms of retinoic acid signalling and its roles in organ and limb development. *Nat Rev Mol Cell Biol* 16, 110-123, doi:10.1038/nrm3932 (2015).

22 Allenby, G. et al. Retinoic acid receptors and retinoid X receptors: interactions with endogenous retinoic acids. *Proc Natl Acad Sci USA* 90, 30-34 (1993).

23 Das, B. C. et al. Retinoic acid signaling pathways in development and diseases. *Bioorganic & medicinal chemistry* 22, 673-683, doi:10.1016/j.bmc.2013.11.025 (2014).

24 Wysocki, P. T. et al. Adenoid cystic carcinoma: emerging role of translocations and gene fusions. *Oncotarget* 7, 66239-66254, doi: 10. 18632/oncotarget. 11288 (2016).

25 Evans, R. M. & Mangelsdorf, D. J. Nuclear Receptors, RXR, and the Big Bang. *Cell* 157, 255-266, doi:10.1016/j.cell.2014.03.012 (2014).

26 Ruggeri, B. A., Camp, F. & Miknyoczki, S. Animal models of disease: pre-clinical animal models of cancer and their applications and utility in drug discovery. *Biochemical pharmacology* 87, 150-161, doi:10.1016/j.bcp.2013.06.020 (2014).

27 Seethala, R. R. An update on grading of salivary gland carcinomas. *Head and neck pathology* 3, 69-77, doi: 10.1007/s12105-009-0102-9 (2009).

28 Moskaluk, C. A. et al. Development and characterization of xenograft model systems for adenoid cystic carcinoma. *Laboratory investigation; a journal of technical methods and pathology* 91, 1480-1490, doi:10.1038/labinvest.2011.105 (2011).

29 Drier, Y. et al. An oncogenic MYB feedback loop drives alternate cell fates in adenoid cystic carcinoma. *Nat Genet* 48, 265-272, doi:10.1038/ng.3502 (2016).

30 Rivera, C. M. & Ren, B. Mapping human epigenomes. *Cell* 155, 39-55, doi:10.1016/j.cell.2013.09.011 (2013).

31 Degos, L. & Wang, Z. Y. All trans retinoic acid in acute promyelocytic leukemia. *Oncogene* 20, 7140-7145, doi: 10.1038/sj.onc. 1204763 (2001).

32 Lo-Coco, F. et al. Targeted Therapy Alone for Acute Promyelocytic Leukemia. *N Engl J Med* 374, 1197-1198, doi:10.1056/NEJMc1513710 (2016).

33 Stoeck, A. et al. Discovery of biomarkers predictive of GSI response in triple-negative breast cancer and adenoid cystic carcinoma. *Cancer discovery* 4, 1154-1167, doi: 10.1158/2159-8290. CD-13-0830 (2014).

34 Hall, C., Flores, M. V., Storm, T., Crosier, K. & Crosier, P. The zebrafish lysozyme C promoter drives myeloid-specific expression in transgenic fish. *BMC developmental biology* 7, 42, doi:10.1186/1471-213X-7-42 (2007).

35 Ellett, F., Pase, L., Hayman, J. W., Andrianopoulos, A. & Lieschke, G. J. mpeg1 promoter transgenes direct macrophage-lineage expression in zebrafish. *Blood* 117, e49-56, doi:10.1182/blood-2010-10-314120 (2011).

36 Thisse, C. & Thisse, B. High-resolution in situ hybridization to whole-mount zebrafish embryos. *Nature protocols* 3, 59-69, doi:10.1038/nprot.2007.514 (2008).

37 Li, P. et al. Epoxyeicosatrienoic acids enhance embryonic haematopoiesis and adult marrow engraftment. *Nature* 523, 468-471, doi:10.1038/nature14569 (2015).

38 Poon, M. M. & Chen, L. Retinoic acid-gated sequence-specific translational control by RARalpha. *Proc Natl Acad Sci USA* 105, 20303-20308, doi:10.1073/pnas.0807740105 (2008).

39 Luk, C. T. et al. FAK signalling controls insulin sensitivity through regulation of adipocyte survival. *Nature communications* 8, 14360, doi:10.1038/ncomms14360 (2017).

40 Lee, T. I., Johnstone, S. E. & Young, R. A. Chromatin immunoprecipitation and microarray-based analysis of protein location. *Nature protocols* 1, 729-748, doi: 10.1038/nprot.2006.98 (2006).

41 Mazzoni, E. O. et al. Saltatory remodeling of Hox chromatin in response to rostrocaudal patterning signals. *Nat Neurosci* 16, 1191-1198, doi:10. 1038/nn.3490 (2013).

42 Kaufman, C. K. et al. A zebrafish melanoma model reveals emergence of neural crest identity during melanoma initiation. *Science* 351, aad2197, doi:10.1126/science.aad2197 (2016).

43 Langmead, B. & Salzberg, S. L. Fast gapped-read alignment with Bowtie 2. *Nature methods* 9, 357-359, doi: 10.1038/nmeth. 1923 (2012).

44 Zhang, Y. et al. Model-based analysis of ChIP-Seq (MACS). *Genome biology* 9, R137, doi:10.1186/gb-2008-9-9-r137 (2008).

45 Trompouki, E. et al. Lineage regulators direct BMP and Wnt pathways to cell-specific programs during differentiation and regeneration. *Cell* 147, 577-589, doi:10.1016/j.cell.2011.09.044 (2011).

Example 3: ATRA Comparison Studies in ACC PDX Models

Figure 31A:
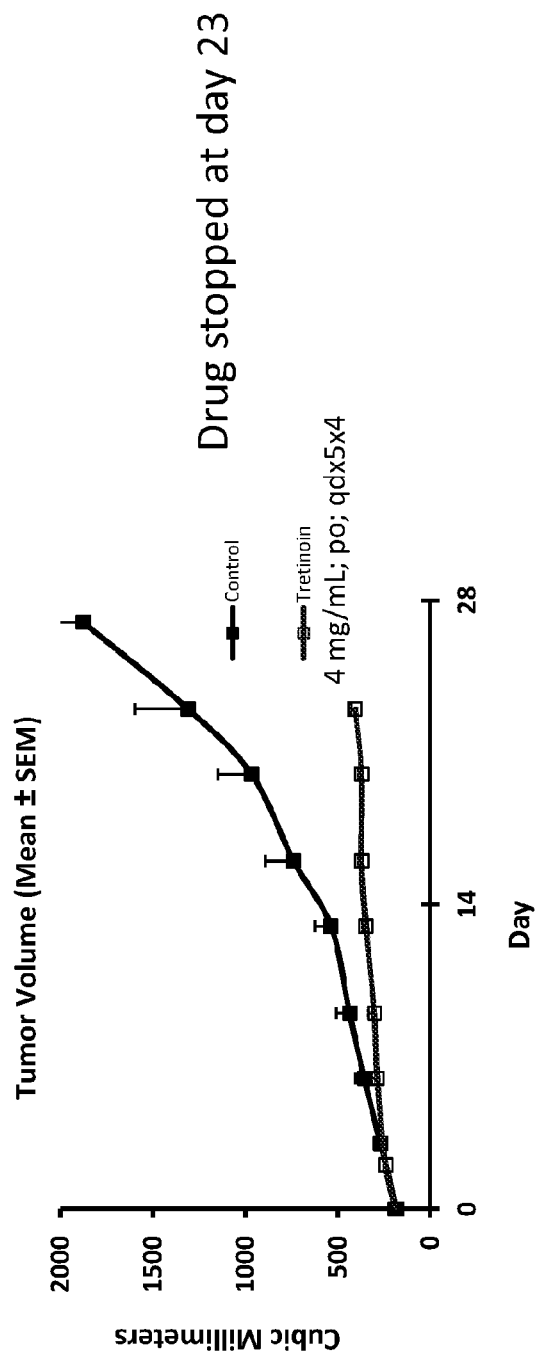
Figure 31B:
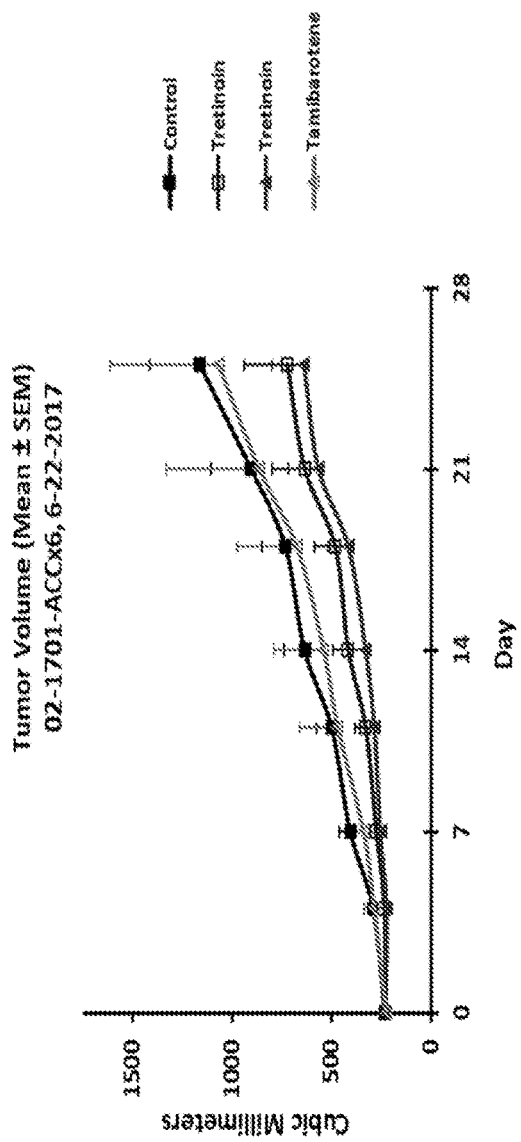
Figure 31C:
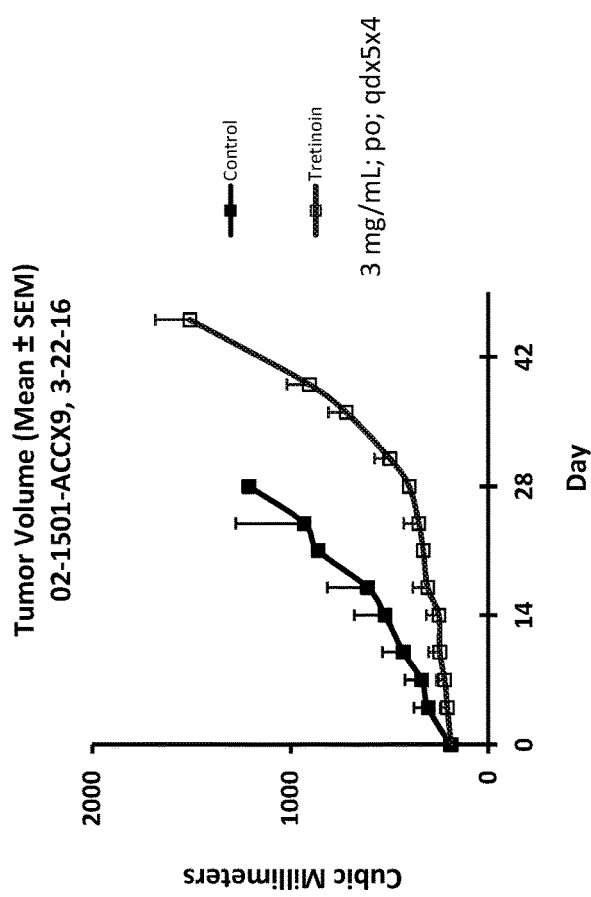
Figure 31D:
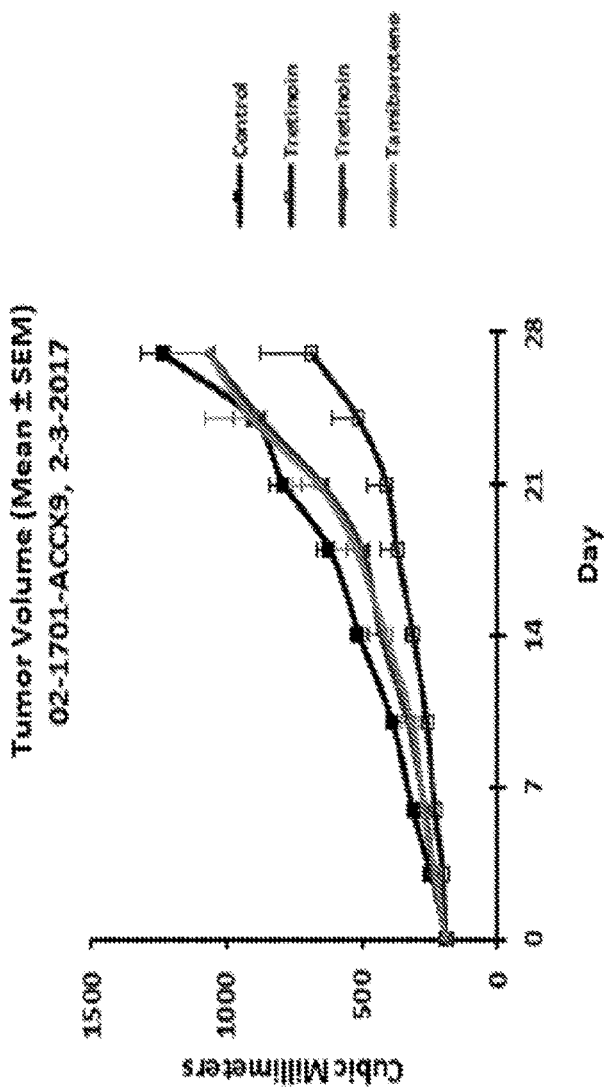
Figure 31E:
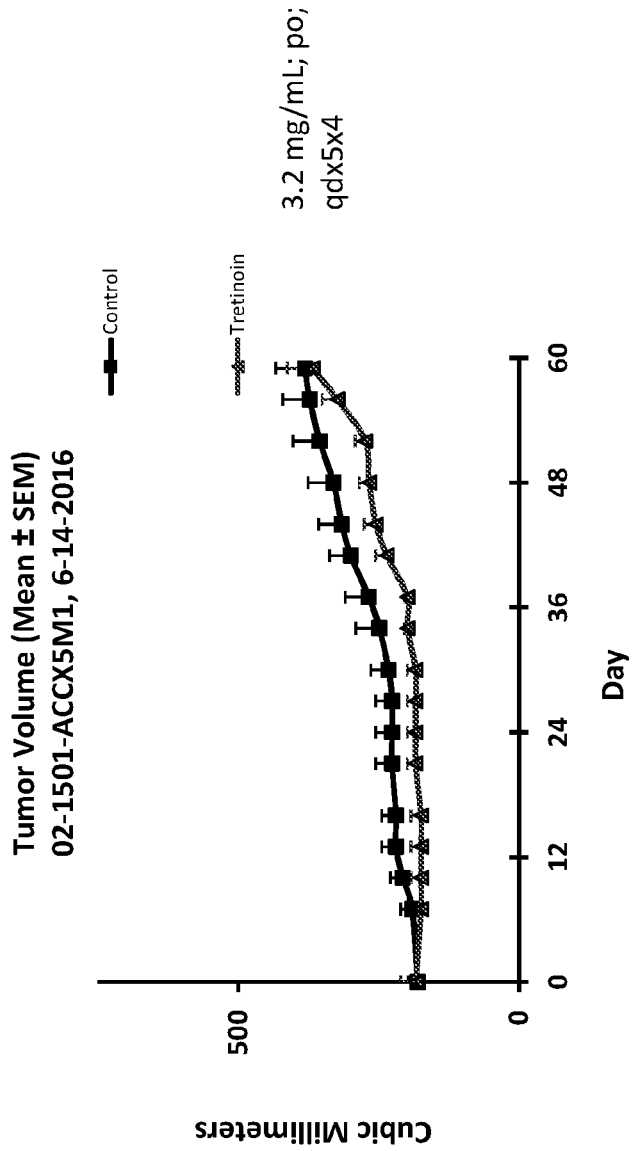
Figure 31D:
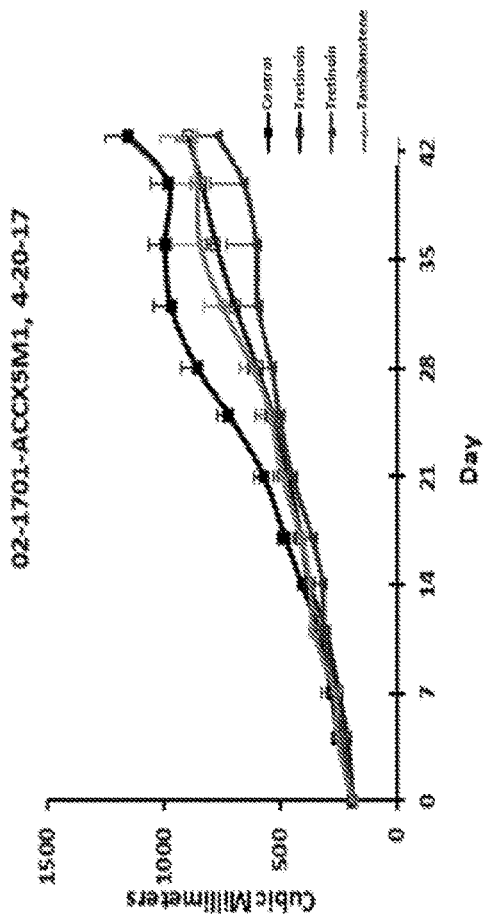
Figure 31G:
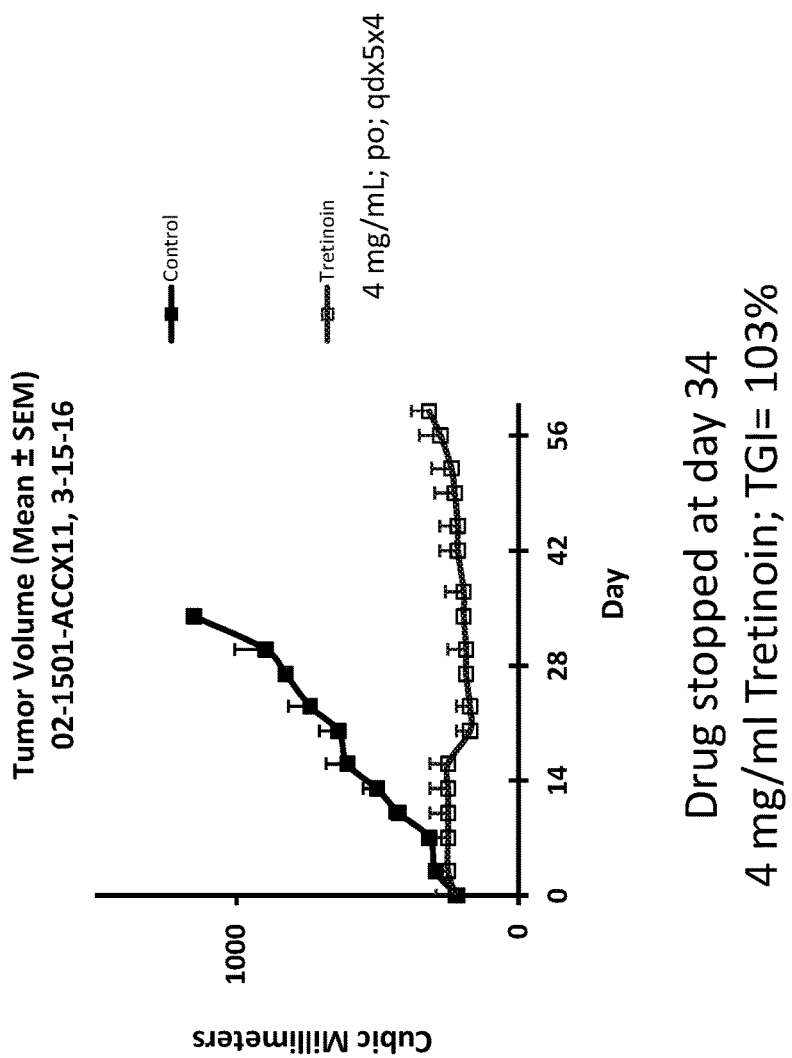

The TGI studies in ACC PDX models were repeated in order to compare the original ATRA dose (3 or 4 mg/ml) against a more physiologically relevant dose of ATRA (8 mg/kg) and an alternative retinoid Tamibarotene (originally developed for ATRA-resistant cancer settings, approved in Japan and currently in development at Syros Pharmaceuticals). Results are shown in FIGS. 31-31G.

All patents and other publications identified in the specification and examples are expressly incorporated herein by reference for all purposes. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated can be further modified to incorporate features shown in any of the other embodiments disclosed herein.

The invention claimed is:

1. A method for treatment of adenoid cystic carcinoma (ACC) comprising: selecting a subject in need of treatment for ACC and administering a therapeutically effective amount of a retinoic acid receptor agonist to the subject, wherein the retinoic acid receptor agonist is selected from the group consisting of all-trans retinoic acid (ATRA), 13-cis-retinoic acid (isotretinoin), 4-[(5,6,7,8-Tetrahydro-5,5,8,8-tetramethyl-2-naphthalenyl)carboxamido] benzoic acid (AM-580), Tamibarotene, 9-cis-retinoic acid, retinoic acid p-hydroxyanilide (Fenretinide), 4-[(E)-2-(5,6,7,8-Tetrahydro-5,5,8,8-tetramethyl-2-naphthalenyl)-1-propenyl]-benzoic acid (TTNPB), and 4-[4-(2-Butoxyethoxy-)-5-methyl-2-thiazolyl]-2-fluorobenzoic acid (AC 261066).

2. The method of claim 1, wherein the subject does not require or is not undergoing treatment for acute promyelocytic leukemia (APL).

3. The method of claim 1, wherein the subject has a gene translocation in oncogenic transcription factor MYB.

4. The method of claim 3, wherein said gene translocation is MYB-NFIB fusion (MYB-NFIB translocation).

5. The method of claim 1, wherein the retinoic acid receptor agonist is selected from the group consisting of all-trans retinoic acid (ATRA), 13-cis-retinoic acid (isotretinoin), 4-[(5,6,7,8-Tetrahydro-5,5,8,8-tetramethyl-2-naphthalenyl)carboxamido] benzoic acid (AM-580), Tamibarotene, 9-cis retinoic acid, retinoic acid p-hydroxyanilide (Fenretinide), and 4-[(E)-2-(5,6,7,8-Tetrahydro-5,5,8,8-tetramethyl-2-naphthalenyl)-1-propenyl]benzoic acid (TTNPB).

6. The method of claim 5, wherein the retinoic acid receptor agonist is all-trans retinoic acid.

7. The method of claim 1, wherein the agonist is administered in amount from about 1 µg/kg to about 150 mg/kg per day.

8. The method of claim 7, wherein the agonist is administered in amount from about 10 mg/kg to about 40 mg/kg per day.

9. The method of claim 7, wherein said administration is in a single dosage.

10. The method of claim 7, wherein said administration is in two or more dosages.

11. The method of claim 1, wherein the agonist is administered orally.

12. The method of claim 1, further comprising administering an anticancer therapy.

13. The method of claim 1, further comprising administering a chemotherapy agent or an immunotherapy agent.

14. The method of claim 13, wherein the chemotherapy agent or the immunotherapy agent is not a cyclooxygenase-2-inhibitor.

15. The method of claim 13, wherein the chemotherapy agent or the immunotherapy agent is not sulindac.

* * * * *

SEQUENCE LISTING

```
<160> NUMBER OF SEQ ID NOS: 14

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tgatgcttcc caacacagag                                                 20

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ttcagaggga atcgtctgct                                                 20

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cgagcaggag atgggaacc                                                  19

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
caacggaaac gctcattgc                                                  19

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ggcagaaatc gcaaagctac                                                 20

<210> SEQ ID NO 6
<211> LENGTH: 20
<212> TYPE: DNA
```

<213> ORGANISM: Artificial Sequence
<220> FEATURE:
<223> OTHER INFORMATION: Description of Artificial Sequence: Synthetic primer

<400> SEQUENCE: 6
accttcctgt tcgaccttcc        20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 7
ctgacttcaa cagcgacacc        20

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 8
tgctgtagcc aaattcgttg t        21

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 9
agtggggtgg cttttaggat        20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 10
ccgaggactt tgattgcaca        20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 11
gctgctgttg tgctctttca        20

<210> SEQ ID NO 12
<211> LENGTH: 20
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 12
ttgagtgagc aggtttgtgg                                                  20

<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
aagctgaccc tgaagttcat ctgc                                             24

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cttgtagttg ccgtcgtcct tgaa                                             24
```